US006759047B1

(12) United States Patent
Kalluri

(10) Patent No.: US 6,759,047 B1
(45) Date of Patent: Jul. 6, 2004

(54) ANTI-ANGIOGENIC PROTEINS AND METHODS OF USE THEREOF

(75) Inventor: Raghuram Kalluri, Boston, MA (US)

(73) Assignee: Beth Israel Deaconess Hospital Corp., Boston, MA (US)

(*) Notice: Subject to any disclaimer, the term of this patent is extended or adjusted under 35 U.S.C. 154(b) by 0 days.

(21) Appl. No.: 09/335,224

(22) Filed: Jun. 17, 1999

Related U.S. Application Data

(60) Provisional application No. 60/089,689, filed on Jun. 17, 1998, and provisional application No. 60/126,175, filed on Mar. 25, 1999.

(51) Int. Cl.[7] .................. A61K 38/16; A61K 38/17; A61K 39/00
(52) U.S. Cl. .................... 424/185.1; 530/324; 530/356; 514/12
(58) Field of Search .................. 514/12, 2; 530/350, 530/356, 353, 324; 424/185.1

(56) References Cited

U.S. PATENT DOCUMENTS

| | | |
|---|---|---|
| 5,114,840 A | 5/1992 | Tryggvason et al. |
| 5,424,408 A | 6/1995 | Reeders et al. |
| 5,567,609 A | 10/1996 | Sarras, Jr. et al. |
| 5,593,900 A | 1/1997 | Tryggvason et al. |
| 5,691,182 A | 11/1997 | Sarras, Jr. et al. |
| 5,731,192 A | 3/1998 | Reeders et al. |
| 5,753,230 A | 5/1998 | Brooks et al. |
| 5,766,591 A | 6/1998 | Brooks et al. |
| 5,856,184 A | 1/1999 | Sarras, Jr. et al. |
| 5,973,120 A | 10/1999 | Reeders et al. |
| 6,007,980 A | 12/1999 | Reeders et al. |
| 6,017,926 A | 1/2000 | Askew et al. |

FOREIGN PATENT DOCUMENTS

| | | | |
|---|---|---|---|
| WO | WO 89/03392 | * | 4/1989 |
| WO | WO 91/08755 | | 6/1991 |
| WO | WO 91/09113 | | 6/1991 |
| WO | WO 96/00582 | | 1/1996 |
| WO | WO 97/06791 | | 2/1997 |
| WO | WO 97/45137 | | 12/1997 |
| WO | WO 99/02551 | | 1/1999 |
| WO | WO 99/16465 | | 4/1999 |
| WO | WO 99/49885 | | 10/1999 |
| WO | WO 99/65940 | | 12/1999 |
| WO | WO 00/11475 | | 3/2000 |
| WO | WO 00/31248 | | 6/2000 |
| WO | WO 00/59532 | | 10/2000 |

OTHER PUBLICATIONS

Battegay, E.J., Angiogenesis: mechanistic insights, neovascular diseases, and therapeutic prospects, J. Mol. Med. 73:333–346, 1995.*
Bergers et al., Effects of Angiogenesis Inhibitors on Multistage Carcinogenesis in Mice, Science 284:808–812, Apr., 1999.*
Attwood TK. Genomics. The Babel of bioinformatics. Science. 290(5491):471–473, 2000.*
Skolnick et al. From genes to protein structure and function: novel applications of computational approaches in the genomic era. Trends Biotechnol. 18(1):34–9, 2000.*
Ngo J.T, Marks J., Karplus M., Computational complexity, protein structure prediction, and the Levinthal paradox in The Protein Folding Problem, ch.14, pp. 435–508, Birkhauser, 1994.*
Tai–Ping et al., Trends in Pharm. Sci. 16(2):57–66, Feb. 1995.*
Skolnick et al., Trends in Biotech., 18(1):34–39, Jan. 2000.*
Wallace, R., Drug Discovery Today, 3(10):433–434, Oct., 1998.*
Sasaki et al., J. Mol. Biol. 301:1179–1190, 2000.*
Prestayko, A.W., et al., "Type IV collagen domains inhibit adhesion and migration of tumor cells and block angiogenesis," *Proceedings of the American Association for Cancer Research,* 39:45 (Mar. 1998).
Sado, Y., et al., "Induction of anti–GBM nephritis in rats by recombinant α3(IV)NC1 and α4(IV)NC1 of type IV collagen," *Kidney International,* 53:664–671 (1998).
Brinker, J.M., et al., GenBank Acc. No. M11315, Nov. 1, 1994.
Killen, P.D., et al., GenBank Acc. No. M24766, Nov. 1, 1994.
Quinones, S., et al., GenBank Acc. No. M92993, Sep. 23, 1994.
Turner, N., et al., GenBank Acc. No. M81379, Oct. 30, 1994.
Mariyama, M., et al., GenBank Acc No. X80031, Oct. 5, 1998.
Han, J., et al., "A Cell Binding Domain from the α3 Chain of Type IV Collagen Inhibits Proliferation of Melanoma Cells," *The Journal of Biological Chemistry,* 272(33):20395–20401 (1997).
Shahan, T.A., et al., "Identification of CD47/Integrin–associated Protein and αvβ3 as Two Receptors for the α3(IV) Chain of Type IV Collagen on Tumor Cells," *Cancer Research,* 59:4584–4590 (1999).
Butkowski, R.J., et al., "Properties of the Globular Domain of Type IV Collagen and Its Relationship to the Goodpasture Antigen," *The Journal of Biological Chemistry,* 260(6):3739–3747 (Mar. 25, 1985).
Gunwar, S., et al., "Properties of the Collagenous Domain of the α3(IV) Chain, The Goodpasture Antigen, of Lens Basement Membrane Collagen," *The Journal of Biological Chemistry,* 266(21):14088–14094 (Jul 25, 1991).

(List continued on next page.)

*Primary Examiner*—Christina Chan
*Assistant Examiner*—Maher M. Haddad
(74) *Attorney, Agent, or Firm*—Palmer & Dodge LLP; Kathleen M. Williams; Barbara A. Gyure

(57) ABSTRACT

Proteins with anti-angiogenic properties are disclosed, and methods of using those proteins to inhibit angiogenesis.

12 Claims, 25 Drawing Sheets

OTHER PUBLICATIONS

Gunwar, S., et al., "Glomerular Basement Membrane," *The Journal of Biological Chemistry*, 273(15):8767–8775 (Apr. 10, 1998).

Hostikka, S.L. and Tryggvason, K., "The Complete Primary Structure of the α2 Chain of Human Type IV Collagen and Comparison with the α1(IV) Chain," *The Journal of Biological Chemistry*, 263(36):19488–19493 (Dec. 25, 1998).

Kalluri, R., et al., "The α3 chain of type IV collagen induces autoimmune Goodpasture syndrome," *Proc. Natl. Acad. Sci. USA*, 91:6201–6205 (Jun. 1994).

Kalluri, R. et al., "The Goodpasture Autoantigen," *The Journal of Biological Chemistry*, 271(15):9062–9068 (Apr. 12, 1996).

Kalluri, R., et al., "Isoform Switching of Type IV Collagen is Developmentally Arrested in X–Linked Alport Syndrome Leading to Increased Susceptibility of Renal Basement Membranes to Endoproteolysis," *J. Clin. Invest.*, 99(10):2470–2478 (May 1997).

Langeveld, J.P.M., et al., "Structural Heterogeneity of the Noncollagenous Domain of Basement Membrane Collagen," *The Journal of Biological Chemistry*, 263(21):10481–10488 (Jul. 25, 1988).

Liotta, L.A., "Cancer Cell Invasion and Metastasis," *Scientific American*, 54–64 (Feb. 1992).

Maragoudakis, M.E., et al., "Basement membrane biosynthesis as a target for developing inhibitors of angiogenesis with anti–tumor properties," *Kidney International*, 43:147–150 (1993).

Mariyama, M., et al., "The α4(IV) Chain of Basement Membrane Collagen," *The Journal of Biological Chemistry*, 267(2):1253–1258 (Jan. 15, 1992).

Mariyama, M., et al., "Colocalization of the Genes for the α3(IV) and α4(IV) Chains of Type V Collagen to Chromosome 2 Bands q35–q37," *Genomics*, 13:809–813 (1992).

Monboisse, J.C., et al., "The α3 Chain of Type IV Collagen Prevents Activation of Human Polymorphonuclear Leukocytes," *The Journal of Biological Chemistry*, 269(41):25475–25482 (Oct. 14, 1994).

Morrison, K.E., et al., "Sequence and Localization of a Partial cDNA Encoding the Human α3 Chain of Type IV Collagen," *Am. J. Hum. Genet.*, 49:545–554 (1991).

Neilson, E.G., et al., "Specificity of Goodpasture Autoantibodies for the Recombinant Noncollagenous Domains of Human Type IV Collagen," *The Journal of Biological Chemistry*, 268(12):8402–8405 (Apr. 25, 1993).

Prockop, D.J. and Kivirikko, K.I., "Collagens: Molecular Biology, Diseases, and Potentials for Therapy," *Annu. Rev. Biochem.*, 64:403–34 (1995).

Sarras Jr., M.P., et al., "Extracellular Matrix (Mesoglea) of *Hydra vulgaris*," *Developmental Biology*, 148:481–494 (1991).

Saus, J., et al., "Identification of the Goodpasture Antigen as the α3(IV) Chain of Collagen IV," *The Journal of Biological Chemistry*, 283(26):13374–13380 (Sep. 1988).

Timpl, R., et al., "A Network Model for the Organization of Type IV Collagen Molecules in Basement Membranes," *Eur. J. Biochem.*, 120:203–211 (1981).

Vuorio, E. and de Crombrugghe, B., "The Family of Collagen Genes," *Annu. Rev. Biochem.*, 59:837–72 (1990).

Zhou, J., et al., "Deletion of the Paired α5(IV) and α6(IV) Collagen Genes in Inherited Smooth Muscle Tumors," *Science*, 261:1167–1169 (Aug. 27, 1993).

Senger, D.R. et al., "Angiogenesis promoted by vascular endothelial growth factor: Regulation through $\alpha_1\beta_1$ and $\alpha_2\beta_1$ integrins," *Proc. Natl. Acad. Sci. USA* 94:13612–13617 (1997).

Colorado, P.C. et al., 1999, "Arresten: Angiogenesis and Renal Cell Carcinoma Tumor Inhibiting Matrix Protein", *J. Amer. Soc. Nephrol.* 10:489A.

Colorado, P.C. et al., 2000, "Anti–Angiogenic Cues From Vascular Basement Membrane Collagen", *Cancer Res.* 60:2520–2526.

Kamphaus, G.D. et al., 1999, "Canstatin: A Novel Matrix Derived Inhibitor of Angiogenesis and Renal Cell Carcinoma Tumor Growth", *J. Amer. Soc. Nephrol.* 10:495A.

Kefalides, N.A. et al., 1999, "Suppression of Tumor Cell Growth By Type IV Collagen and a Peptide From the NC1 Domain of the α3(IV) Chain", *Medicina* 59:553.

Maeshima, Y. et al., 2000, "Two RGD–Independent $\alpha_v\beta_3$ Integrin Binding Sites on Tumstatin Regulate Distinct Anti–Tumor Properties", *J. Biol. Chem.* 275:23745–23750.

Nickols, A. et al., 1997, "Antiangiogenic and anticancer Activities of Antagonists if Integrin $\alpha_v\beta_3$", *Proc. Ann. Mtg. Amer. Assoc. Cancer Res.* 38:206.

Varner, J.A., 1997, "The Role of Vascular Cell Integrins $\alpha_v\beta_3$ and $\alpha_v\beta_5$ in Angiogenesis", *Regulation of Angiogenesis*, Biurkhauser Verlag, Basel, Switzerland, pp. 361–390.

Boudreau, N. et al., "Suppression of ICE and Apoptosis in Mammary Epithelial Cells by Extracellular Matrix," *Science* 267:891–893 (1995).

Briesewitz, R. et al., "Expression of Native and Truncated Forms of the Human Integrin $\alpha_1$ Subunit," *J. Biol. Chem.* 268:2989–2996 (1993).

Brooks, P.C. et al., "Requirement of Vascular Integrin $\alpha_v\beta_3$ for Angiogenesis," *Science* 264: 569–571 (1994).

Chan, B.M.C. et al., "In Vitro and In Vivo Consequences of VLA–2 Expression on Rhabdomyosarcoma Cells," *Science* 251:1600–1602 (1991).

Dickeson, S.K. et al., "Determinants of Ligand Binding Specificity of the $\alpha_1$ and $\beta_1$ Integrins," *J. Biol. Chem.* 274:32182–32191 (1999).

Fleischmajer, R. et al., "There is Binding of Collagen IV to β1 Integrin During Early Skin Basement Membrane Assembly," *Ann. N.Y. Acad. Sci.* 857:212–227 (1998).

Gehlsen, K.R. et al., "Subunit Structure of a Laminin–Binding Integrin and Localization of its Binding Site on Laminin," *J. Biol. Chem.* 264:19034–19038 (1989).

Hynes, R.O., "Integrins: Versatility, Modulation, and Signaling in Cell Adhesion," *Cell* 69:11–25 (1992).

Ivaska, J. et al., "A peptide Inhibiting the Collagen Binding Function of Integrin $\alpha_1 I$ Domain," *J . Biol. Chem.* 274:3513–3521 (1999).

Kalluri, R. and D. Cosgrove, "Assembly of Type IV Collagen," *J. Biol. Chem.* 275: 12719–12724 (2000).

Kalluri, R. and V.P. Sukhatme, "Fibrosis and Angiogenesis," *Curr. Opin. Nephrol. Hypert.* 9:413–418 (2000).

Kalluri, R. et al., "Reactive Oxygen Species Expose Cryptic Epitopes Associated with Autoimmune Goodpasture Syndrome," *J. Biol. Chem* 275: 20027–20032 (2000).

Kamphaus, G. D., et al., "Canstatin, a Novel Matrix–derived Inhibitor of Angiogenesis and Tumor Growth," *J. Biol Chem.* 275:1209–1215 (2000).

Kern, A. et al., "The Role of the I Domain in Ligand Binding of the Human Integrin $\alpha 1\beta 1$," *J. Biol. Chem.* 269:22811–22816 (1994).

Kramer, R.H. and Marks, N., "Identification of Integrin Collagen Receptors on Human Melanoma Cells," *J. Biol. Chem.* 264:4684–4688 (1989).

Lochter, A. et al., "α1 and α2 Integrins Mediate Invasive Activity of Mouse Mammary Carcinoma Cells through Regulation of Stromelysin–1 Expression," *Mol. Biol. Cell* 10:271–282 (1999).

Maeshima, Y et al., "Distinct Antitumor Properties of a Type IV Collagen Domain Derived from Basement Membrane", *J. Biol. Chem.* 275:21340–21348 (2000).

Maeshima, Y. et al., "Tumstatin, an Endothelial Cell–Specific Inhibitor of Protein Synthesis," *Science* 295: 140–143 (2002).

Miles, A.J. et al., "Promotion of Cell Adhesion by Single–stranded and Triple–helical Peptide Models of Basement Membrane Collagen α1(IV) 531–543," *J. Biol. Chem.* 269:30939–30945 (1994).

Miles, A.J. et al., "A Peptide Model of Basement membrane Collagen α1(IV) 531–543 Binds the $\alpha_3\beta_1$ Integrin," *J. Biol. Chem.* 270:29047–29050 (1995).

Mooney, A. et al., "Type IV Collagen and Laminin Regulate Glomerular Mesangial Cell Susceptibility to Apoptosis Via $\beta_1$ Integrin–Mediated Survival Signals," *Amer. J. Pathol.* 155:599–606 (1999).

Petitclerc, E. et al., "New Functions for Non–collagenous Domains of Human Collagen Type IV," *J. Bio. Chem.* 275:8051–8061 (2000).

Varner, J.A. et al., "Review: The Integrin $\alpha_v\beta_3$: Angiogenesis and Apoptosis." In: *Cell Adhesion & Communication,* C.A. Buck and J.P. Thiery (eds.) Harwood Academic Publishers, (1995).

Witkowski, C.M. and Kramer, J.M. "Site–Directed Mutations of Evolutionarily Conserved Sites on Type IV Collagen In *C. elegans*," Early 1997 International Worm Meeting Abstract 650 (1997).

* cited by examiner

FIG. 1A pET22b(+) forward primer:
　　5'-CGGGATCCT TCT GTT GAT CAC GGC TTC-3'　(SEQ ID NO:3)
pET22b(+) reverse primer:
　　5'-CCCAAGCTT TGT TCT TCT CAT ACA GAC-3'　(SEQ ID NO:4)
pPICZαA forward primer:
　　5'-TTCGGAATTC TCT GTT GAT CAC GGC TTC-3'　(SEQ ID NO:15)
pPICZαA reverse primer:
　　5'-TGCTCTAGAGG TGT TCT TCT CAT ACA GAC TTG GCA-3'　(SEQ ID NO:16)

```
         5      10      15      20      25      30      35      40      45
       tct gtt gat cac ggc ttc ctt gtg acc agg cat agt caa aca ata
        50      55      60      65      70      75      80      85      90
       gat gac cca cag tgt cct tct ggg acc aaa att ctt tac cac ggg
        95     100     105     110     115     120     125     130     135
       tac tct ttg ctc tac gtg caa ggc aat gaa cgg gcc cat gga cag
       140     145     150     155     160     165     170     175     180
       gac ttg ggc acg gcc ggc agc tgc ctg cgc aag ttc agc aca atg
       185     190     195     200     205     210     215     220     225
       ccc ttc ctg ttc tgc aat att aac aac gtg tgc aac ttt gca tca
       230     235     240     245     250     255     260     265     270
       cga aat gac tac tcg tac tgg ctg tcc acc cct gag ccc atg ccc
       275     280     285     290     295     300     305     310     315
       atg tca atg gca ccc atc acg ggg gaa aac ata aga cca ttt att
       320     325     330     335     340     345     350     355     360
       agt agg tgt gct gtg tgt gag gcg cct gcc atg gtg atg gcc gtg
       365     370     375     380     385     390     395     400     405
       cac agc cag acc att cag atc cca ccg tgc ccc agc ggg tgg tcc
       410     415     420     425     430     435     440     445     450
       tcg ctg tgg atc ggc tac tct ttt gtg atg cac acc agc gct ggt
       455     460     465     470     475     480     485     490     495
       gca gaa ggc tct ggc caa gcc ctg gcg tcc ccc ggc tcc tgc ctg
       500     505     510     515     520     525     530     535     540
       gag gag ttt aga agt gcg cca ttc atc gag tgt cac ggc cgt ggg
       545     550     555     560     565     570     575     580     585
       acc tgc aat tac tac gca aac gct tac agc ttt tgg ctc gcc acc
       590     595     600     605     610     615     620     625     630
       ata gag agg agc gag atg ttc aag aag cct acg ccg tcc acc ttg
       635     640     645     650     655     660     665     670     675
       aag gca ggg gag ctg cgc acg cac gtc agc cgc tgc caa gtc tgt
       680     685     690
       atg aga aga aca taa      (SEQ ID NO:1)
```

FIG. 1B

```
      5      10      15      20      25      30      35      40      45
SVD  HGF  LVT  RHS  QTI  DDP  QCP  SGT  KIL  YHG  YSL  LYV  QGN  ERA  HGQ
     50      55      60      65      70      75      80      85      90
DLG  TAG  SCL  RKF  STM  PFL  FCN  INN  VCN  FAS  RND  YSY  WLS  TPE  PMP
     95     100     105     110     115     120     125     130     135
MSM  API  TGE  NIR  PFI  SRC  AVC  EAP  AMV  MAV  HSQ  TIQ  IPP  CPS  GWS
    140     145     150     155     160     165     170     175     180
SLW  IGY  SFV  MHT  SAG  AEG  SGQ  ALA  SPG  SCL  EEF  RSA  PFI  ECH  GRG
    185     190     195     200     205     210     215     220     225
TCN  YYA  NAY  SFW  LAT  IER  SEM  FKK  PTP  STL  KAG  ELR  THV  SRC  QVC
    229
MRR  T         (SEQ ID NO:2)
```

Forward primer: 5'-cgggatccttctgttgatcacggcttc-3'

Reverse primer: 5'-cccaagctttgttcttctcatacagac-3'

Control

Arresten 2 µg/ml

Endostatin 20 µg/ml

FIG. 10A pET22b(+) forward primer:
    5'-CGGGATCCT <u>GTC AGC ATC GGC TAC CTC</u>-3'  (SEQ ID NO:7)
pET22b(+) reverse primer:
    5'-CCCAAGCTT <u>CAG GTT CTT CAT GCA CAC</u>-3'  (SEQ ID NO:8)
pPICZαA forward primer:
    5'-TTCGGAATTC <u>GTC AGC ATC GGC TAC CTC CTG</u>-3'  (SEQ ID NO:17)
pPICZαA reverse primer:
    5'-GGGGTACCCC <u>CAG GTT CTT CAT GCA CAC CTG G</u>-3'  (SEQ ID NO:18)

```
         5      10      15      20      25      30      35      40      45
        gtc    agc    atc    ggc    tac    ctc    ctg    gtg    aag    cac    agc    cag    acg    gac    cag 50     55     60     65     70     75     80     85     90
        gag    ccc    atg    tgc    ccg    gtg    ggc    atg    aac    aaa    ctc    tgg    agt    gga    tac 95     100    105    110    115    120    125    130    135
        agc    ctg    ctg    tac    ttc    gag    ggc    cag    gag    aag    gcg    cac    aac    cag    gac 140    145    150    155    160    165    170    175    180
        ctg    ggg    ctg    gcg    ggc    tcc    tgc    ctg    gcg    cgg    ttc    agc    acc    atg    ccc 185    190    195    200    205    210    215    220    225
        ttc    ctg    tac    tgc    aac    cct    ggt    gat    gtc    tgc    tac    tat    gcc    agc    cgg 230    235    240    245    250    255    260    265    270
        aac    gac    aag    tcc    tac    tgg    ctc    tct    acc    act    gcg    ccg    ctg    ccc    atg 275    280    285    290    295    300    305    310    315
        atg    ccc    gtg    gcc    gag    gac    gag    atc    aag    ccc    tac    atc    agc    cgc    tgt 320    325    330    335    340    345    350    355    360
        tct    gtg    tgt    gag    gcc    ccg    gcc    atc    gcc    atc    gcg    gtc    cac    agt    cag 365    370    375    380    385    390    395    400    405
        gat    gtc    tcc    atc    cca    cac    tgc    cca    gct    ggg    tgg    cgg    agt    ttg    tgg 410    415    420    425    430    435    440    445    450
        atc    gga    tat    tcc    ttc    ctc    atg    cac    acg    gcg    gcg    gga    gac    gaa    ggc 455    460    465    470    475    480    485    490    495
        ggt    ggc    caa    tca    ctg    gtg    tca    ccg    ggc    agc    tgt    cta    gag    gac    ttc 500    505    510    515    520    525    530    535    540
        cgc    gcc    aca    cca    ttc    atc    gaa    tgc    aat    gga    ggc    cgc    ggc    acc    tgc 545    550    555    560    565    570    575    580    585
        cac    tac    tac    gcc    aac    aag    tac    agc    ttc    tgg    ctg    acc    acc    att    ccc 590    595    600    605    610    615    620    625    630
        gag    cag    agc    ttc    cag    ggc    tcg    ccc    tcc    gcc    gac    acg    ctc    aag    gcc 635    640    645    650    655    660    665    670    675
        ggc    ctc    atc    cgc    aca    cac    atc    agc    cgc    tgc    cag    gtg    tgc    atg    aag
        680
        aac    ctg    tga        (SEQ ID NO:5)
```

FIG. 10B

```
      5      10      15      20      25      30      35      40      45
VSI  GYL  LVK  HSQ  TDQ  EPM  CPV  GMN  KLW  SGY  SLL  YFE  GQE  KAH  NQD
     50      55      60      65      70      75      80      85      90
LGL  AGS  CLA  RFS  TMP  FLY  CNP  GDV  CYY  ASR  NDK  SYW  LST  TAP  LPM
     95     100     105     110     115     120     125     130     135
MPV  AED  EIK  PYI  SRC  SVC  EAP  AIA  IAV  HSQ  DVS  IPH  CPA  GWR  SLW
    140     145     150     155     160     165     170     175     180
IGY  SFL  MHT  AAG  DEG  GGQ  SLV  SPG  SCL  EDF  RAT  PFI  ECN  GGR  GTC
    185     190     195     200     205     210     215     220     225
HYY  ANK  YSF  WLT  TIP  EQS  FQG  SPS  ADT  LKA  GLI  RTH  ISR  CQV  CMK
227
NL        (SEQ ID NO:6)
```

Forward primer: 5'-cgggatcctgtcagcatcggctacctc-3'

Reverse primer: 5'-cccaagcttcaggttcttcatgcacac-3'

FIG. 16A pET22b(+) forward primer:
    5'-CGG GAT CCG <u>GGT TTG AAA GGA AAA CGT</u>-3' (SEQ ID NO:11)

pET22b(+) reverse primer:
    5'-CCC AAG CTT <u>TCA GTG TCT TTT CTT CAT</u>-3' (SEQ ID NO:12)

```
        5        10       15       20       25       30       35       40       45
      ggt ttg  aaa gga  aaa cgt  gga gac  agt gga  tca cct  gca acc  tgg
       50       55       60       65       70       75       80       85       90
      aca acg  aga ggc  ttt gtc  ttc acc  cga cac  agt caa  acc aca  gca
       95      100      105      110      115      120      125      130      135
      att cct  tca tgt  cca gag  ggg aca  gtg cca  ctc tac  agt ggg  ttt
      140      145      150      155      160      165      170      175      180
      tct ttt  ctt ttt  gta caa  gga aat  caa cga  gcc cac  gga caa  gac
      185      190      195      200      205      210      215      220      225
      ctt gga  act ctt  ggc agc  tgc ctg  cag cga  ttt acc  aca atg  cca
      230      235      240      245      250      255      260      265      270
      ttc tta  ttc tgc  aat gtc  aat gat  gta tgt  aat ttt  gca tct  cga
      275      280      285      290      295      300      305      310      315
      aat gat  tat tca  tac tgg  ctg tca  aca cca  gct ctg  atg cca  atg
      320      325      330      335      340      345      350      355      360
      aac atg  gct ccc  att act  ggc aga  gcc ctt  gag cct  tat ata  agc
      365      370      375      380      385      390      395      400      405
      aga tgc  act gtt  tgt gaa  ggt cct  gcg atc  gcc ata  gcc gtt  cac
      410      415      420      425      430      435      440      445      450
      agc caa  acc act  gac att  cct cca  tgt cct  cac ggc  tgg att  tct
      455      460      465      470      475      480      485      490      495
      ctc tgg  aaa gga  ttt tca  ttc atc  atg ttc  aca agt  gca ggt  tct
      500      505      510      515      520      525      530      535      540
      gag ggc  acc ggg  caa gca  ctg gcc  tcc cct  ggc tcc  tgc ctg  gaa
      545      550      555      560      565      570      575      580      585
      gaa ttc  cga gcc  agc cca  ttt cta  gaa tgt  cat gga  aga gga  acg
      590      595      600      605      610      615      620      625      630
      tgc aac  tac tat  tca aat  tcc tac  agt ttc  tgg ctg  gct tca  tta
      635      640      645      650      655      660      665      670      675
      aac cca  gaa aga  atg ttc  aga aag  cct att  cca tca  act gtg  aaa
      680      685      690      695      700      705      710      715      720
      gct ggg  gaa tta  gaa aaa  ata ata  agt cgc  tgt cag  gtg tgc  <u>atg</u>
      725      730      735
      <u>aag aaa aga cac tga</u>         (SEQ ID NO:9)
``` pET22b-α3(IV) NC1 = nucleotides 1 through 732
Tumstatin 333 = nucleotides 1 through 372
Tumstatin 334 - nucleotide 373 through 732

FIG. 16B

```
        *
             5          10         15         20         25         30         35         40         45
        GLK GKR GDS GSP ATW TTR GFV FTR HSQ TTA IPS CPE GTV PLY SGF 50          55         60         65         70         75         80         85         90
        SFL FVQ GNQ RAH GQD LGT LGS CLQ RFT TMP FLF CNV NDV CNF ASR
                                                                *+
            95         100        105        110        115        120        125        130        135
        NDY SYW LST PAL MPM NMA PIT GRA LEP YIS RCT VCE GPA IAI AVH 140         145        150        155        160        165        170        175        180
        SQT TDI PPC PHG WIS LWK GFS FIM FTS AGS EGT GQA LAS PGS CLE 185         190        195        200        205        210        215        220        225
        EFR ASP FLE CHG RGT CNY YSN SYS FWL ASL NPE RMF RKP IPS TVK
                                          +
           230         235        240        244
        AGE LEK IIS RCQ VCM KKR H       (SEQ ID NO:10)
``` pET22b α3(IV) NC1 = residues 1 through 244
Tumstatin 333 = residues 1 through 124
Tumstatin 334 = residues 125 through 244

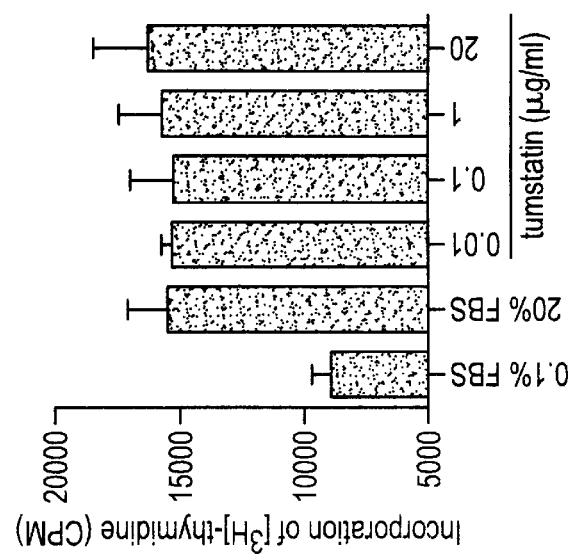
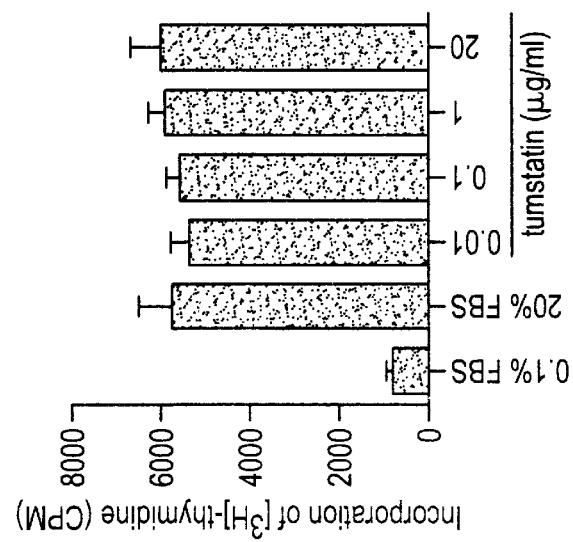
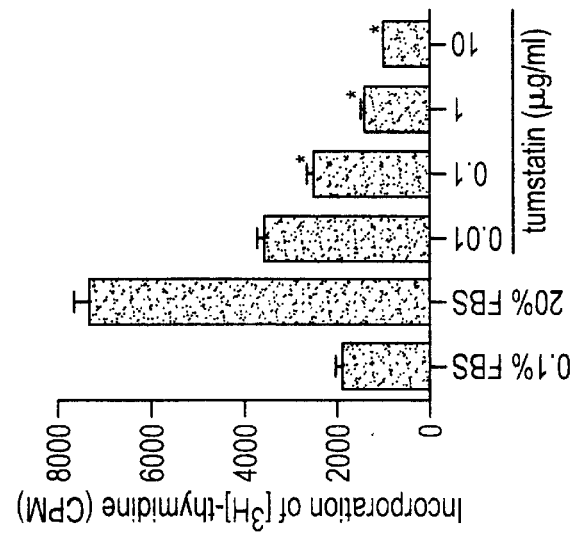

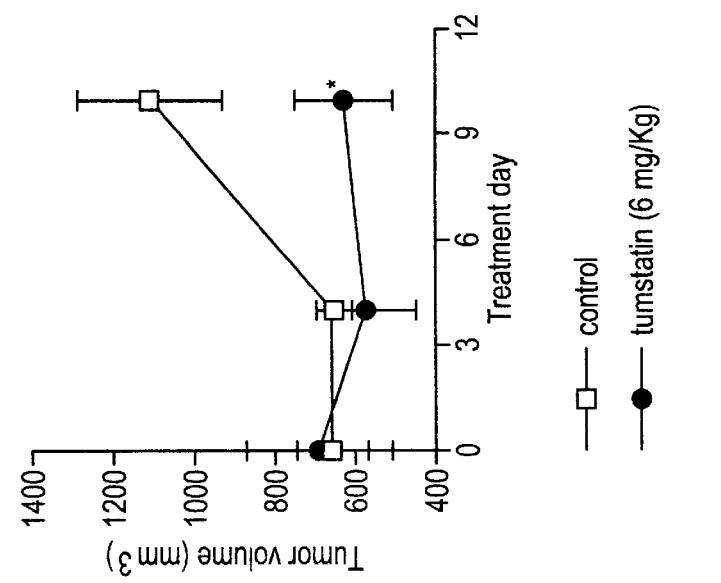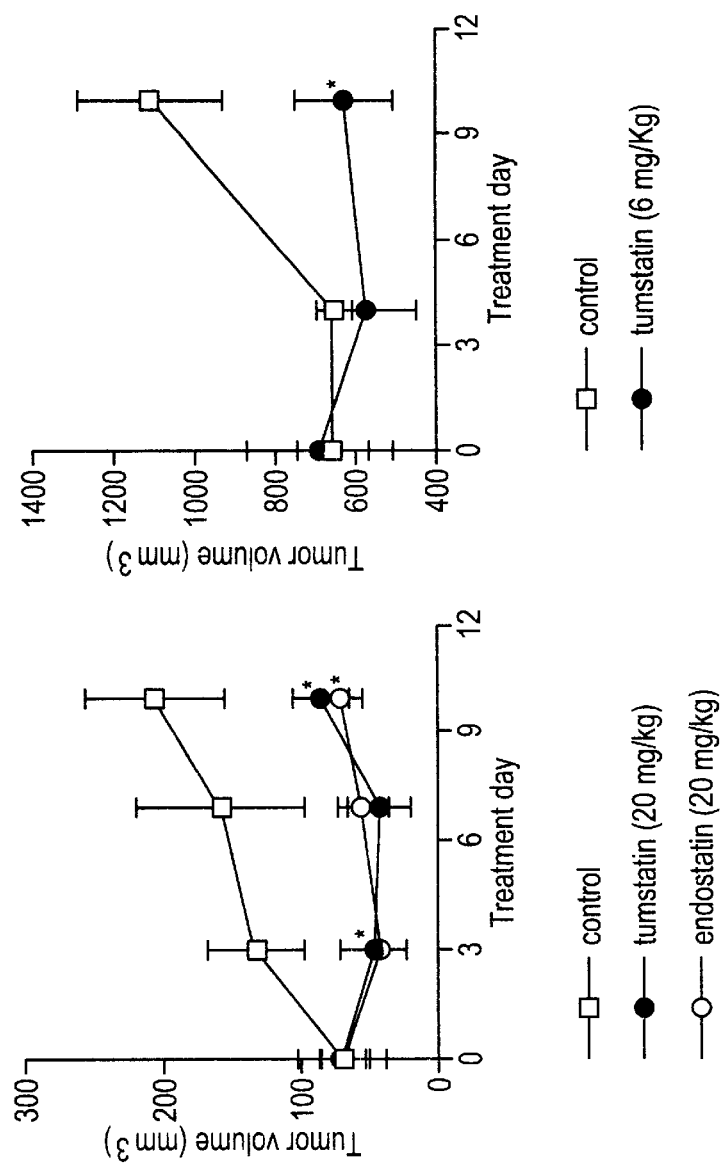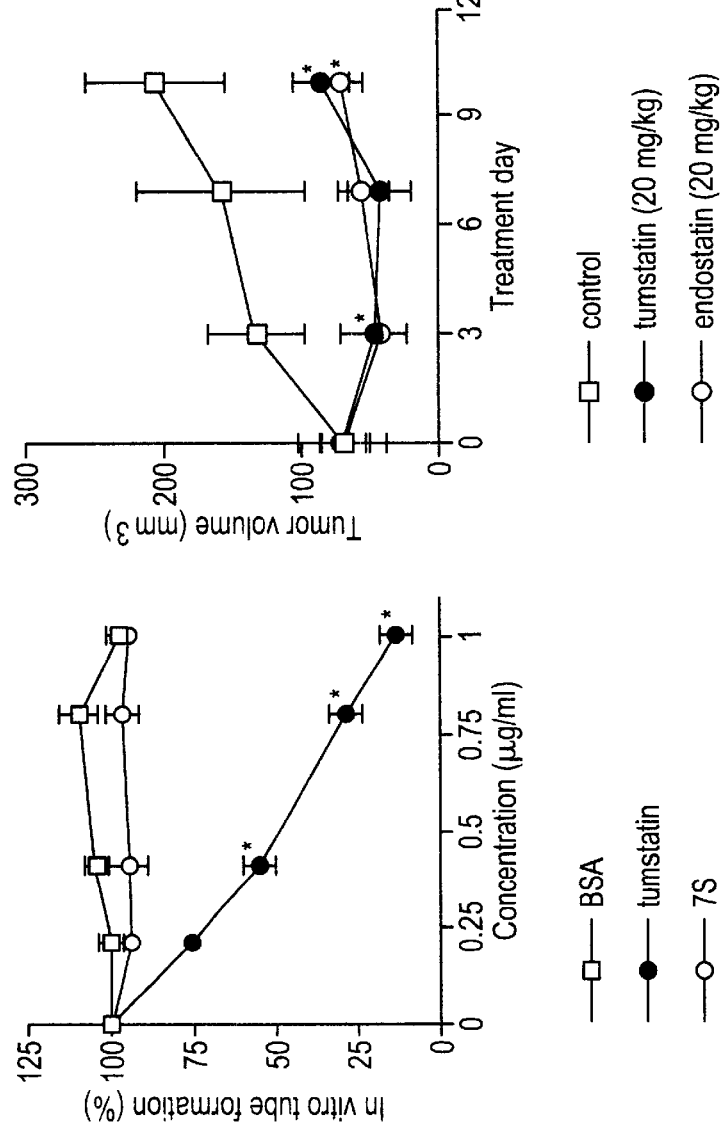
FIG. 20
FIG. 21A
FIG. 21B

ANTI-ANGIOGENIC PROTEINS AND METHODS OF USE THEREOF

RELATED APPLICATION(S)

This application claims the benefit of U.S. provisional application No. 60/089,689, filed Jun. 17, 1998, and also U.S. provisional application No. 60/126,175, filed Mar. 25, 1999, the entire teachings of which are incorporated herein by reference.

GOVERNMENT SUPPORT

The invention was supported, in whole or in part, by grants DK-51711, DK-55001 and R01-CA42596-12, from the National Institutes of Health. The Government has certain rights in the invention.

BACKGROUND OF THE INVENTION

Vascular basement membranes are composed of macromolecules such as collagen, laminin, heparan sulfate proteoglycans, fibronectin and entactin (Timpl, R., 1996, Curr Opin Cell Biol 8:618–24). Functionally, collagen promotes cell adhesion, migration, differentiation and growth (Paulsson, M., 1992, Crit. Rev. Biochem. Mol. Biol. 27:93–127), and via these functions is presumed to play a crucial role in endothelial cell proliferation and behavior during angiogenesis, which is the process of formation of new blood vessels from pre-existing ones (Madri, J. A. et al., 1986, J. Histochem. Cytochem. 34:85–91; Folkman, J., 1972, Ann. Surg. 175:409–16). Angiogenesis is a complex process, and requires sprouting and migration of endothelial cells, proliferation of those cells, and their differentiation into tube-like structures and the production of a basement membrane matrix around the developing blood vessel. Additionally angiogenesis is a process critical for normal physiological events such as wound repair and endometrium remodeling (Folkman, J. et al., 1995, J. Biol. Chem. 267:10931–34). It is now well documented that angiogenesis is required for metastasis and growth of solid tumors beyond a few mm in size (Folkman, J., 1972, Ann. Surg. 175:409–16; Folkman, J., 1995, Nat. Med. 1:27–31). Several studies have shown that inhibitors of collagen metabolism have anti-angiogenic properties, supporting the notion that basement membrane collagen synthesis and deposition is crucial for blood vessel formation and survival (Maragoudakis, M. E. et al., 1994, Kidney Int. 43:147–50; Haralabopoulos, G. C. et al., 1994, Lab. Invest. 71:575–82). However, the precise role of collagen in basement membrane organization and angiogenesis is still not well understood.

SUMMARY OF THE INVENTION

The present invention relates to proteins comprising the NC1 domain of an alpha chain of Type IV collagen having anti-angiogenic properties. In particular, the present invention relates to the novel proteins Arresten, Canstatin and Tumstatin, and to biologically active (e.g., anti-angiogenic) fragments, mutants, analogs, homologs and derivatives thereof, as well as multimers (e.g., dimers) and fusion proteins (also referred to herein as chimeric proteins) thereof. These proteins all comprise the C-terminal fragment of the NC1 (non-collagenous 1) domain of Type IV collagen. More specifically, Arresten, Canstatin and Tumstatin are each a C-terminal fragment of the NC1 domain of the α1 chain, α2 chain and α3 chain, respectively, of Type IV collagen. In particular, Arresten, Canstatin and Tumstatin are monomeric proteins. All three arrest tumor growth in vivo, and also inhibit the formation of capillaries in several in vitro models, including the endothelial tube assay.

The present invention encompasses isolated and recombinantly-produced Arresten, also referred to herein as "Arrestin," which comprises the NC1 domain of the α1 chain of Type IV collagen, having anti-angiogenic activity, anti-angiogenic fragments of the isolated Arresten, multimers of the isolated Arresten and anti-angiogenic fragments, and polynucleotides encoding those anti-angiogenic proteins. Also encompassed are compositions comprising isolated Arresten, its anti-angiogenic fragments, or both, as biologically active components. In another embodiment, the invention features a method of treating a proliferative disease such as cancer, in a mammal where said disease is characterized by angiogenic activity, the method comprising administering to the mammal a composition containing anti-angiogenic Arresten or its fragments. The anti-angiogenic Arresten and its fragments can also be used to prevent cell migration or endothelial cell proliferation. Also featured are antibodies to the isolated anti-angiogenic Arresten and its fragments.

The present invention also encompasses isolated and recombinantly produced Canstatin, which comprises the NC1 domain of the α2 chain of Type IV collagen, having anti-angiogenic activity, anti-angiogenic fragments of the isolated Canstatin, multimers of the isolated Canstatin and anti-angiogenic fragments, and polynucleotides encoding those anti-angiogenic proteins. Also encompassed are compositions comprising isolated Canstatin, its anti-angiogenic fragments, or both, as biologically active ingredients. In another embodiment, the invention features a method of treating a proliferative disease such as cancer, in a mammal, where said disease is characterized by angiogenic activity, the method comprising administering to the mammal a composition containing anti-angiogenic Canstatin or its fragments. The anti-angiogenic Canstatin and its fragments can also be used to prevent cell migration or endothelial cell proliferation. Also featured are antibodies to the isolated anti-angiogenic Canstatin and its fragments.

The invention likewise encompasses isolated and recombinantly-produced Tumstatin, comprising the NC1 domain of the α3 chain of Type IV collagen, having anti-angiogenic activity, anti-angiogenic fragments of the isolated Tumstatin, multimers of the isolated Tumstatin and anti-angiogenic fragments, and polynucleotides encoding those anti-angiogenic proteins. Also encompassed are compositions comprising isolated Tumstatin, its anti-angiogenic fragments, or both, as biologically active ingredients. In another embodiment, the invention features a method of treating a proliferative disease such as cancer in a mammal, where said disease is characterized by angiogenic activity, the method comprising administering to the mammal a composition containing anti-angiogenic Tumstatin or its fragments. The anti-angiogenic Tumstatin and its fragments can also be used to prevent cell migration or endothelial cell proliferation. Also featured are antibodies to the isolated anti-angiogenic Tumstatin and its fragments.

BRIEF DESCRIPTION OF THE DRAWINGS

FIGS. 1A and 1B are diagrams depicting the nucleotide (FIG. 1A, SEQ ID NO:1) and amino acid (FIG. 1B, SEQ ID NO:2) sequences of the α1 chain of human Type IV collagen. The locations of the pET22b(+) forward (SEQ ID NO:3) and reverse (SEQ ID NO:4) primers are indicated by double underlining, and the locations of the pPICZαA forward (SEQ ID NO:15) and reverse (SEQ ID NO:16) primers are indicated by single underlining.

FIGS. 4A, 4B and 4C show the effect of Arresten (0 μg/ml–50 μg/ml (FIGS. 4A and 4B) and 0 μg/ml–10 μg/ml (FIG. 4C)) on 786-O, PC-3, HPEC cells respectively. FIG. 4D shows the effect of 0.1–10 μg/ml endostatin on A-498 cells.

FIG. 5A shows untreated control cells.

FIG. 6 shows the effect of either Arresten (2 μg/ml or 20 μg/ml) and endostatin (2.5 μg/ml and 20 μg/ml) on the migration of ECV-304 endothelial cells.

FIG. 9A is a plot showing the increase in tumor volume from 700 mm$^3$ for 10 mg/kg Arresten-treated (□), BSA-treated (+), and control mice (●). FIG. 9B shows the increase in tumor volume from 100 mm$^3$ for 10 mg/kg Arresten-treated (□) and BSA-treated (+) tumors. FIG. 9C shows the increase in tumor volume from about 100 mm$^3$ for 10 mg/kg Arresten-treated (□), Endostatin-treated (▲), and control mice (●). FIG. 9D shows the increase for 200 mm$^3$ tumors when treated with Arresten (□) versus controls (●).

FIGS. 10A and 10B are diagrams depicting the nucleotide (FIG. 10A, SEQ ID NO:5) and amino acid (FIG. 10B, SEQ ID NO:6) sequences of the α2 chain of human Type IV collagen. The locations of the pET22b(+) forward (SEQ ID NO:7) and reverse (SEQ ID NO:8) primers are indicated by double underlining, and the locations of the pPICZαA forward (SEQ ID NO:17) and reverse (SEQ ID NO:17) primers are indicated by single underlining.

FIGS. 16A and 16B are diagrams depicting the nucleotide (FIG. 16A, SEQ ID NO:9) and amino acid (FIG. 16B, SEQ ID NO:10) sequence of the α3 chain of human Type IV collagen. The locations of the pET22b(+) forward (SEQ ID NO:11) and reverse (SEQ ID NO:12) primers are indicated by double underlining. The beginning and end of the "Tumstatin 333" and "Tumstatin 334" fragments are also indicated ("*"=Tumstatin 333; "+"=Tumstatin 334).

FIGS. 19A, 19B and 19C are a set of three histograms showing $^3$H-thymidine incorporation (y-axis) for C-PAE cells (FIG. 19A), PC-3 cells (FIG. 19B) and 786-O cells (FIG. 19C) when treated with varying concentrations of Tumstatin (x-axis). All groups represent triplicate samples.

FIG. 20 is a line graph showing the effect on endothelial tube formation (y-axis) of varying amounts (x-axis) of Tumstatin (●), BSA (control, □) and 7S domain (control, ○).

FIGS. 21A and 21B are a pair of line graphs showing the effects on tumor volume (mm$^3$, y-axis) against days of treatment (x-axis) of Tumstatin (●) and endostatin (○) versus controls (□). Data points marked with an asterisk are significant, with $P<0.05$ by one-tailed Student's test.

DETAILED DESCRIPTION OF THE INVENTION

Figure 2:
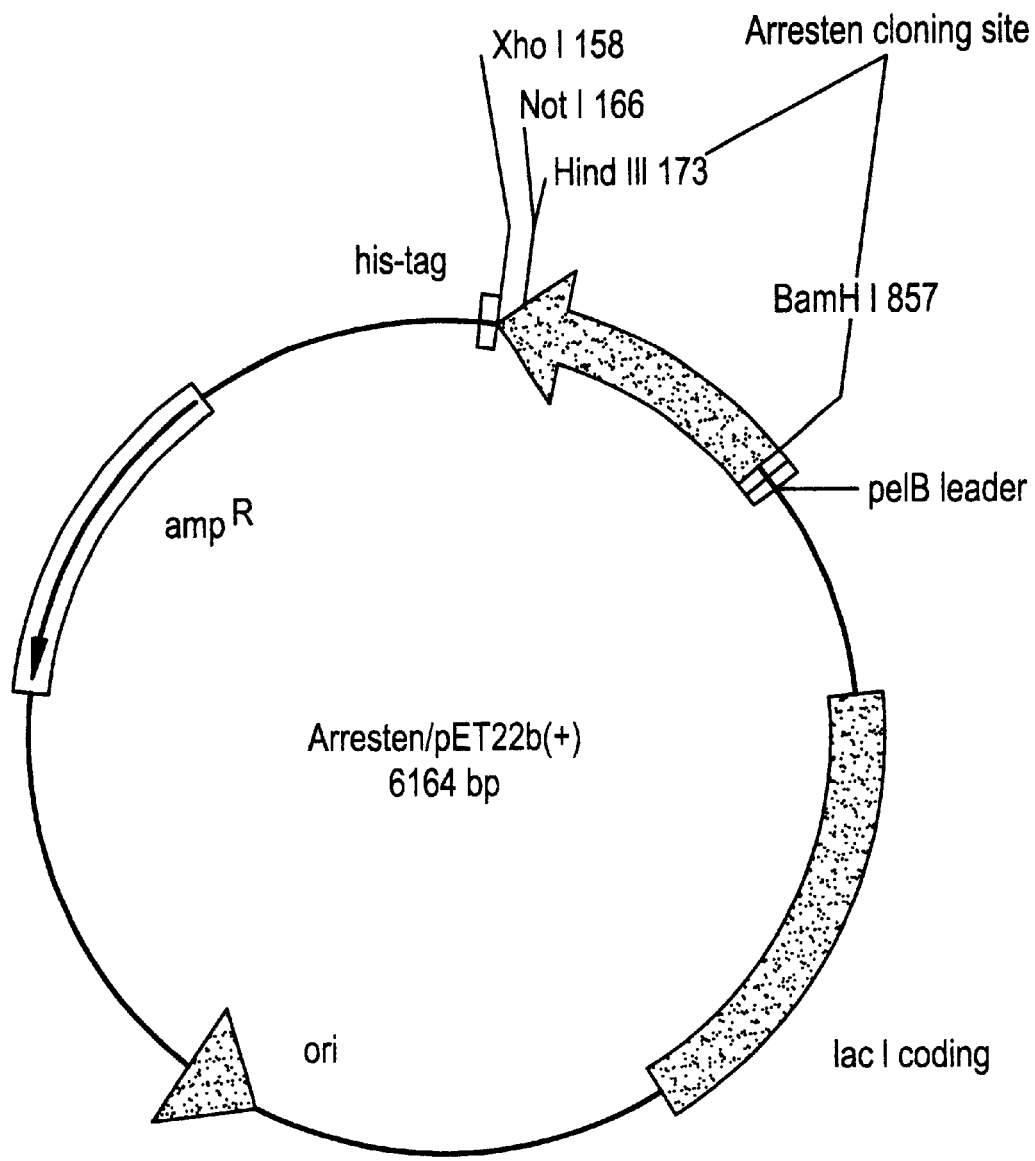
FIG. 2 is a schematic diagram representing the Arresten cloning vector pET22b(+). Forward (SEQ ID NO:3) and reverse (SEQ ID NO:4) primers and site into which Arresten was cloned are indicated.

A wide variety of diseases are the result of undesirable angiogenesis. Put another way, many diseases and undesirable conditions could be prevented or alleviated if it were possible to stop the growth and extension of capillary blood vessels under some conditions, at certain times, or in particular tissues. Basement membrane organization is dependent on the assembly of a type IV collagen network which is speculated to occur via the C-terminal globular non-collagenous (NC1) domain of type IV collagen (Timpl, R., 1996, Curr Opin Cell Biol 8:618–24; Timpl, R. et al., 1981, Eur. J. Biochem. 120:203–211). Type IV collagen is composed of six distinct gene products, namely, $\alpha 1$ through $\alpha 6$ (Prockop, D. J. et al., 1995, Annu. Rev. Biochem. 64:403–34). The $\alpha 1$ and $\alpha 2$ isoforms are ubiquitously present in human basement membranes (Paulsson, M., 1992, Crit. Rev. Biochem. Mol. Biol. 27:93–127), while the other four isoforms exhibit restricted distributions (Kalluri, R. et al., 1997, J. Clin. Invest. 99:2470–8).

The formation of new capillaries from pre-existing vessels, angiogenesis, is essential for the process of tumor growth and metastasis (Folkman, J. et al., 1992, J. Biol. Chem. 267:10931–4; Folkman, J. 1995, Nat. Med. 1:27–31; Hanahan, D. et al., 1996, Cell 86:353–64). Human and animal tumors are not vascularized at the beginning, however for a tumor to grow beyond few $mm^3$, it might vascularize (Folkman, J. 1995, Nat. Med. 1:27–31; Hanahan, D. et al., 1996, Cell 86:353–64). The switch to an angiogenic phenotype requires both upregulation of angiogenic stimulators and downregulation of angiogenesis inhibitors (Folkman, J. 1995, Nat. Med. 1:27–31). Vascular endothelial growth factor (VEGF) and basic fibroblast growth factor (bFGF) are the most commonly expressed angiogenic factors in tumors. Vascularized tumors may overexpress one or more of these angiogenic factors which can synergistically promote tumor growth. Inhibition of a single angiogenic factor such as VEGF with a receptor antagonist is not enough to arrest tumor growth. A number of angiogenesis inhibitors have been recently identified, and certain factors such as IFN-a, platelet-factor-4 (Maione, T. E. et al., 1990, Science 247:77–9) and PEX (Brooks, P. C. et al., 1998, Cell 92:391–400) are not endogenously associated with tumor cells, whereas angiostatin (O'Reilly, M. S. et al., 1994, Cell 79:315–28) and endostatin (O'Reilly, M. S. et al., 1997, Cell 88:277–85) are tumor associated angiogenesis inhibitors generated by tumor tissue itself. Although treatment of tumor growth and metastasis with these endogenous angiogenesis inhibitors is very effective and an attractive idea, some potential problems associated with anti-angiogenic therapies must be considered. Delayed toxicity induced by chronic anti-angiogenic therapy as well as the possibility of impaired wound healing and reproductive angiogenesis occurring during treatment are to be considered seriously.

In the present invention, proteins, and fragments, analogs, derivatives, homologs and mutants thereof with anti-angiogenic properties are described, along with methods of use of these proteins, analogs, derivatives, homologs and mutants to inhibit angiogenesis-mediated proliferative diseases. The proteins comprise the NC1 domain of the $\alpha$ chain of Type IV collagen, or portions of the domain, and specifically comprise monomers of the NC1 domain of the $\alpha 1$, $\alpha 2$ and $\alpha 3$ chains of Type IV collagen. These proteins, especially when in monomeric form, arrest tumor growth in in vivo models of cancer, and also inhibit the formation of capillaries in several in vitro models, including the endothelial tube assay.

These proteins may also include the junction region of the NC1 domain. The $\alpha 1$, $\alpha 2$, or $\alpha 3$ chains are preferred, as evidence suggests that the $\alpha 4$, $\alpha 5$, and $\alpha 6$ chains have reduced or non-detectable anti-angiogenic activity. In general, monomeric forms of the proteins are preferred, as evidence suggests that the hexameric forms also have little or reduced activity.

More particularly, the present invention describes a protein designated "Arresten," which is a protein of about 230 amino acids long, corresponding to the amino acids at the N-terminus of the $\alpha 1$ chain of the NC1 domain of human Type IV collagen (Hostikka, S. L. et al., 1988, J. Biol. Chem. 263:19488–93).

As disclosed herein, human Arresten can be produced in *E. coli* using a bacterial expression plasmid, such as pET22b, which is capable of periplasmic transport, thus resulting in soluble protein. The protein is expressed as a 29 kDa fusion protein with a C-terminal six-histidine tag. The additional 3 kDa (beyond 26 kDa) arises from polylinker and histidine tag sequences. Arresten was also produced as a secreted soluble protein in 293 kidney cells using the pcDNA 3.1 eukaryotic vector. This 293-produced protein has no purification or detection tags.

*E. coli*-produced Arresten inhibits proliferation of bFGF-stimulated endothelial cells in a dose-dependent manner, with an $ED_{50}$ of 0.25 µg/ml. No significant effect was observed on proliferation of renal carcinoma cells (786-O), prostate cancer cells (PC-3), or human prostate epithelial cells (HPEC). Endostatin inhibited proliferation of C-PAE cells at an $ED_{50}$ of 0.75 µg/ml, 3-fold higher than Arresten, and did not inhibit A-498 cancer cells.

The specific inhibition of endothelial cell proliferation and migration, as described herein, indicates that Arresten may function via a cell surface protein or receptor. Inhibition of matrix metalloproteinase, or MMP, suggests a direct role of Arresten in tumor growth and metastases, similar to batimastat (BB-94) and marimastat (BB-2516).

In the present invention, Canstatin, the NC1 domain of the $\alpha 2$ chain of Type IV collagen was used to inhibit angiogenesis, as assayed by inhibition of the proliferation and migration of endothelial cells, and by inhibition of endothelial tube formation. The specific inhibition of endothelial cell proliferation and migration by Canstatin also demonstrate its anti-angiogenic activity, and that it may function via a cell surface protein/receptor. Integrins are potential candidate molecules based on their extracellular matrix binding capacity and ability to modulate cell behavior such as migration and proliferation. In particular, avb3 integrin is a possible canstatin receptor, due to its induction during angiogenesis, and its promiscuous binding capacity.

In the present invention, Tumstatin, the NC1 domain of the $\alpha 3$ chain of type IV collagen (Timpl, R. et al., 1981, Eur. J. Biochem. 120:203–11; Turner, N. et al., 1992, J. Clin. Invest. 89:592–601), was used to modulate the proliferation of vascular endothelial cells and blood vessel formation using in vitro and in vivo models of angiogenesis and tumor growth. The distribution of the $\alpha 3$ (IV) chain is limited to certain basement membranes, such as GBM, several basement membranes of the cochlea, ocular basement membrane such as anterior lens capsule, Descemet's membrane, ovarian and testicular basement membrane (Frojdman, K. et al., 1998, Differentiation 83:125–30) and alveolar capillary basement membrane (Kashtan, C. E., 1998, J. Am. Soc. Nephrol. (9:1736–50). However, this chain is absent from kidney mesangium, vascular basement membranes and epidermal basement membranes of the skin, and vascular basement membrane of liver (Kashtan, C. E., supra). In the process of wound healing, α-chains of type IV collagen other than the α3 and α4 chains will assemble and form new capillaries, because those two chains are not the component of the basement membrane of 'pre-existing', namely dermal vasculatures. Since α3 (IV) chain is not the original component in the skin of normal humans, the process of collagen assembly and angiogenesis in the lesion of wound healing may not be altered by the treatment using tumstatin.

The α3 (IV) chain is expressed in human kidney vascular basement membrane as well as GBM (Kalluri, R. et al., 1997, J. Clin. Invest. 99:2470–8). These 'pre-existing' vessels are speculated to be involved in the progression of primary renal tumors such as renal cell carcinoma. Tumstatin can be effective in the treatment of primary renal tumors by disrupting neovascularization mediated by the assembly of the α3 (IV) chain with the other α-chains. The number of patients diagnosed for renal cell carcinoma was about thirty thousand in the United States in 1996 (Mulders, P. et al., 1997, Cancer Res. 57:5189–95), and the prognosis for metastatic cases is highly unfavorable. Despite advances in radiation therapy and chemotherapy, the long term survival of treated patients has not been remarkably improved yet (Mulders, P., supra). The lack of significant treatment options for renal cell carcinoma emphasizes the importance of developing novel therapeutic strategies. Considering this fact, targeting neovascularization of solid tumors has recently demonstrated promising results in several animal models (Baillie, C. T. et al., 1995, Br. J. Cancer 72:257–67; Burrows, F. J. et al., 1994, Pharmacol. Ther. 64:155–74; Thorpe, P. E. et al., 1995, Breast Cancer Res. Treat. 36:237–51). The effect of tumstatin in inhibiting renal cell carcinoma growth in vivo demonstrates this molecule's potential as an effective anti-angiogenic therapy against this tumor type.

In the present invention, Tumstatin specifically inhibited endothelial cell proliferation and had no effect on the proliferation of tumor cell lines PC-3, and 786-O in vitro. Although tumstatin did not inhibit endothelial cell migration, it significantly suppressed endothelial tube formation in vitro. Collectively, these results show that tumstatin suppresses the formation of new blood vessels by inhibiting various steps in the angiogenic process.

In in vivo studies, tumstatin inhibited angiogenesis in the matrigel plug assay and suppressed the growth of PC-3 tumor and 786-O tumors in mouse xenograft model. The fact that tumstatin inhibited the growth of large tumors is encouraging, especially considering the treatment of tumors in the clinical setting.

Since tumstatin possesses the pathogenic epitope for Goodpasture syndrome, an autoimmune disease characterized by pulmonary hemorrhage and rapidly progressive glomerulonephritis (Butkowski, R. J. et al. 1987, J. Biol. Chem. 262:7874–77; Saus, J. et al., 1988, J. Biol. Chem. 263:13374–80; Kalluri, R. et al., 1991, J. Biol. Chem. 266:24018–24), it is possible that acute or chronic administration of tumstatin may induce this auto-immune disease. Several groups have tried to map or predict the location of the Goodpasture auto-epitope on α3 (IV) NC1, and the N-terminal portion, middle portion, and C-terminal portion were reported to possess the epitope (Kalluri, R. et al., 1995, J. Am. Soc. Nephrol. 6:1178–85; (Kalluri, R. et al., 1996, J. Biol. Chem. 271:9062–8; Levy, J. B. et al., 1997, J. Am. Soc. Nephrol. 8:1698–1705; Quinones, S. et al., 1992, J. Biol. Chem. 267:19780–4; Kefalides, N. A. et al., 1993, Kidney Int. 43:94–100; Netzer, K. O. et al., 1999, J. Biol. Chem. 274:11267–74). Recently it was reported that reactivity of the autoantibody only to the N-terminus of the α3 (IV) NC1 correlated with the renal survival rate by using recombinant chimeric constructs (Hellmark, T. et al., 1999, Kidney Int. 55:936–44). The disease associated epitope to the first 40 amino acids of the N-terminal portion was also identified. Truncated tumstatin was synthesized, lacking the N-terminal 53 amino acid residues in order to remove the epitope for Goodpasture syndrome, and this molecule exhibit inhibitory effect on 786-O tumor growth in mouse xenograft model. Additionally, this molecule did not bind autoantibodies from severe patients with Goodpasture syndrome. These results show that the anti-angiogenic region of tumstatin is conserved even when the N-terminal 53 amino acids are removed.

The specific inhibition of endothelial cell proliferation by tumstatin strongly suggests that it may function via a cell surface protein/receptor. Angiogenesis also depends on specific endothelial cell adhesive events mediated by integrin avb3 (Brooks, P. C. et al., 1994, Cell 79:1157–64). Tumstatin may disrupt the interaction of proliferating endothelial cells to the matrix component, and thus drive endothelial cells to undergo apoptosis (Re, F. et al., 1994, J. Cell. Biol. 127:537–46). Matrix Metalloproteinases (MMP's) have been implicated as key enzymes that regulate the formation of new blood vessels in tumors (Ray, J. M. et al., 1994, Eur. Respir. J. 7:2062–72). Recently, it was demonstrated that an inhibitor of MMP-2 (PEX) can suppress tumor growth by inhibiting angiogenesis (Brooks, P. C. et al., Cell 92:391–400). Tumstatin may function through inhibiting the activity of MMPs.

Tumstatin inhibits angiogenesis in vitro and in vivo, resulting in the suppression of tumor progression. In order to apply this strategy to patients, its potential toxicity or side effects by systemic administration must also be considered. The fact that tumstatin's distribution is limited and is mostly absent in dermal basement membrane suggest less possibility of side effects by tumstatin treatment. Also, existence of tumstatin in vascular basement membrane of limited organs such as kidney suggest its potential unique advantage in targeting tumors arising in limited organs. Ultimately it is desirable to develop alternative strategies to express the tumstatin gene in vivo in tumor vasculature employing gene transfer approaches (Kashihara, N. et al., 1997, Exp. Nephrol. 5:126–31; Maeshima, Y. et al., 1996, J. Am. Soc. Nephrol. 7:2219–29; Maeshima, T. et al., 1998, J. Clin. Invest. 101:2589–97).

The distribution of the α3 (IV) chain is limited to basement membranes of selected organs, and so tumstatin is likely to be less harmful considering the possible mechanism of this molecule by inhibiting the assembly of α-chains. Furthermore the α3 (IV) chain is observed in the vascular basement membrane of the kidney (Kalluri, R. et al., 1997, J. Clin. Invest. 99:2470–8), and these vessels are thought to be involved in the progression of primary renal tumors such as renal cell carcinoma. Therefore, tumstatin may be effective in the treatment of such tumors through disrupting the assembly of the α3 (IV) chain with the other α-chains.

As used herein, the term "angiogenesis" means the generation of new blood vessels into a tissue or organ, and involves endothelial cell proliferation. Under normal physiological conditions, humans or animals undergo angiogenesis only in very specific restricted situations. For example, angiogenesis is normally observed in wound healing, fetal and embryonal development, and formation of the corpus luteum, endometrium and placenta. The term "endothelium"

means a thin layer of flat epithelial cells that lines serous cavities, lymph vessels, and blood vessels. "Anti-angiogenic activity" therefore refers to the capability of a composition to inhibit the growth of blood vessels. The growth of blood vessels is a complex series of events, and includes localized breakdown of the basement membrane lying under the individual endothelial cells, proliferation of those cells, migration of the cells to the location of the future blood vessel, reorganization of the cells to form a new vessel membrane, cessation of endothelial cell proliferation, and, incorporation of pericytes and other cells that support the new blood vessel wall. "Anti-angiogenic activity" as used herein therefore includes interruption of any or all of these stages, with the end result that formation of new blood vessels is inhibited.

Anti-angiogenic activity may include endothelial inhibiting activity, which refers to the capability of a composition to inhibit angiogenesis in general and, for example, to inhibit the growth or migration of bovine capillary endothelial cells in culture in the presence of fibroblast growth factor, angiogenesis-associated factors, or other known growth factors. A "growth factor" is a composition that stimulates the growth, reproduction, or synthetic activity of cells. An "angiogenesis-associated factor" is a factor which either inhibits or promotes angiogenesis. An example of an angiogenesis-associated factor is an angiogenic growth factor, such as basic fibroblastic growth factor (bFGF), which is an angiogenesis promoter. Another example of an angiogenesis-associated factor is an angiogenesis inhibiting factor such as e.g., angiostatin (see, e.g., U.S. Pat. No. 5,801,012, U.S. Pat. No. 5,837,682, U.S. Pat. No. 5,733,876, U.S. Pat. No. 5,776,704, U.S. Pat. No. 5,639,725, U.S. Pat. No. 5,792,845, WO 96/35774, WO 95/29242, WO 96/41194, WO 97/23500) or endostatin (see, e.g., WO 97/15666).

By "substantially the same biological activity" or "substantially the same or superior biological activity" is meant that a composition has anti-angiogenic activity, and behaves similarly as do Arresten, Canstatin and Tumstatin, as determined in standard assays. "Standard assays" include, but are not limited to, those protocols used in the molecular biological arts to assess anti-angiogenic activity, cell cycle arrest, and apoptosis. Such assays include, but are not limited to, assays of endothelial cell proliferation, endothelial cell migration, cell cycle analysis, and endothelial cell tube formation, detection of apoptosis, e.g., by apoptotic cell morphology or Annexin V-FITC assay, chorioallantoic membrane (CAM) assay, and inhibition of renal cancer tumor growth in nude mice. Such assays are provided in the Examples below.

"Arresten," also referred to herein as "Arrestin," is intended to include fragments, mutants, homologs, analogs, and allelic variants of the amino acid sequence of the Arresten sequence, as well as Arresten from other mammals, and fragments, mutants, homologs, analogs and allelic variants of the Arresten amino acid sequence.

"Canstatin," as used herein, is intended to include fragments, mutants, homologs, analogs, and allelic variants of the amino acid sequence of the Canstatin sequence, as well as Canstatin from other mammals, and fragments, mutants, homologs, analogs and allelic variants of the Canstatin amino acid sequence.

"Tumstatin," as used herein, is intended to include fragments, mutants, homologs, analogs, and allelic variants of the amino acid sequence of the Tumstatin sequence, as well as Tumstatin from other mammals, and fragments, mutants, homologs, analogs and allelic variants of the Tumstatin amino acid sequence.

It is to be understood that the present invention is contemplated to include any derivatives of Arresten, Canstatin or Tumstatin that have endothelial inhibitory activity (e.g., the capability of a composition to inhibit angiogenesis in general and, for example, to inhibit the growth or migration of bovine capillary endothelial cells in culture in the presence of fibroblast growth factor, angiogenesis-associated factors, or other known growth factors). The present invention includes the entire Arresten, Canstatin or Tumstatin protein, derivatives of these proteins and biologically-active fragments of these proteins. These include proteins with Arresten, Canstatin or Tumstatin activity that have amino acid substitutions or have sugars or other molecules attached to amino acid functional groups.

The invention also describes fragments, mutants, homologs and analogs of Arresten, Canstatin and Tumstatin. A "fragment" of Arresten, Canstatin or Tumstatin is any amino acid sequence shorter that the Arresten, Canstatin or Tumstatin molecule, comprising at least 25 consecutive amino acids of the Arresten, Canstatin or Tumstatin polypeptide. Such molecules may or may not also comprise additional amino acids derived from the process of cloning, e.g., amino acid residues or amino acid sequences corresponding to full or partial linker sequences. To be encompassed by the present invention, such mutants, with or without such additional amino acid residues, must have substantially the same biological activity as the natural or full-length version of the reference polypeptide.

One such fragment, designated "Tumstatin N-53", was found to have anti-angiogenic activity equivalent to that of full-length Tumstatin, as determined by standard assays. Tumstatin N-53 comprises a Tumstatin molecule wherein the N-terminal 53 amino acids have been deleted. Other mutant fragments described herein have been found to have very high levels of anti-angiogenic activity, as shown by the assays described herein. These fragments, "Tumstatin 333," "Tumstatin 334," "12 kDa Arresten fragment," "8 kDa Arresten fragment," and "10 kDa Canstatin fragment" have $ED_{50}$ values of 75 ng/ml, 20 ng/ml, 50 ng/ml, 50 ng/ml, and 80 ng/ml, respectively. By contrast, full-length Arresten, Canstatin and Tumstatin were found to have $ED_{50}$ values of 400 ng/ml, 400 ng/ml, and 550 ng/ml, respectively. Tumstatin 333 comprises amino acids 1 to 124 of SEQ ID NO:10, and Tumstatin 334 comprises amino acids 125 to 244 of SEQ ID NO:10.

By "mutant" of Arresten, Canstatin or Tumstatin is meant a polypeptide that includes any change in the amino acid sequence relative to the amino acid sequence of the equivalent reference Arresten, Canstatin or Tumstatin polypeptide. Such changes can arise either spontaneously or by manipulations by man, by chemical energy (e.g., X-ray), or by other forms of chemical mutagenesis, or by genetic engineering, or as a result of mating or other forms of exchange of genetic information. Mutations include, e.g., base changes, deletions, insertions, inversions, translocations, or duplications. Mutant forms of Arresten, Canstatin or Tumstatin may display either increased or decreased anti-angiogenic activity relative to the equivalent reference Arresten, Canstatin or Tumstatin polynucleotide, and such mutants may or may not also comprise additional amino acids derived from the process of cloning, e.g., amino acid residues or amino acid sequences corresponding to full or partial linker sequences.

Mutants/fragments of the anti-angiogenic proteins of the present invention can be generated by PCR cloning. The fragments designated "Tumstatin 333" and "Tumstatin 334" were generated in this way, and have anti-angiogenic activity superior to that of full-length Tumstatin, as is described in Example 18, below, and shown in FIGS. 23 and 24. To make such fragments, PCR primers are designed from known sequence in such a way that each set of primers will amplify known subsequence from the overall protein. These subsequences are then cloned into an appropriate expression vector, such as the pET22b vector, and the expressed protein tested for its anti-angiogenic activity as described in the assays below.

Mutants/fragments of the anti-angiogenic proteins of the present invention can also be generated by Pseudomonas elastase digestion, as described by Mariyama, M. et al. (1992, J. Biol. Chem. 267:1253–8), and in Example 24, below. This method was used to produce the 12 kDa and 8 kDa Arrestin mutants, and the 10 kDa Canstatin mutant, all three of which have higher levels of anti-angiogenic activity than the original full-length proteins.

By "analog" of Arresten, Canstatin or Tumstatin is meant a non-natural molecule substantially similar to either the entire Arresten, Canstatin or Tumstatin molecule or a fragment or allelic variant thereof, and having substantially the same or superior biological activity. Such analogs are intended to include derivatives (e.g., chemical derivatives, as defined above) of the biologically active Arresten, Canstatin or Tumstatin, as well as its fragments, mutants, homologs, and allelic variants, which derivatives exhibit a qualitatively similar agonist or antagonist effect to that of the unmodified Arresten, Canstatin or Tumstatin polypeptide, fragment, mutant, homolog, or allelic variant.

By "allele" of Arresten, Canstatin or Tumstatin is meant a polypeptide sequence containing a naturally-occurring sequence variation relative to the polypeptide sequence of the reference Arresten, Canstatin or Tumstatin polypeptide. By "allele" of a polynucleotide encoding the Arresten, Canstatin or Tumstatin polypeptide is meant a polynucleotide containing a sequence variation relative to the reference polynucleotide sequence encoding the reference Arresten, Canstatin and Tumstatin polypeptide, where the allele of the polynucleotide encoding the Arresten, Canstatin or Tumstatin polypeptide encodes an allelic form of the Arresten, Canstatin or Tumstatin polypeptide.

It is possible that a given polypeptide may be either a fragment, a mutant, an analog, or allelic variant of Arresten, Canstatin or Tumstatin, or it may be two or more of those things, e.g., a polypeptide may be both an analog and a mutant of the Arresten, Canstatin or Tumstatin polypeptide. For example, a shortened version of the Arresten, Canstatin or Tumstatin molecule (e.g., a fragment of Arresten, Canstatin or Tumstatin) may be created in the laboratory. If that fragment is then mutated through means known in the art, a molecule is created that is both a fragment and a mutant of Arresten, Canstatin or Tumstatin. In another example, a mutant may be created, which is later discovered to exist as an allelic form of Arresten, Canstatin or Tumstatin in some mammalian individuals. Such a mutant Arresten, Canstatin or Tumstatin molecule would therefore be both a mutant and an allelic variant. Such combinations of fragments, mutants, allelic variants, and analogs are intended to be encompassed in the present invention.

For example, the Tumstatin made by the E. coli expression cloning method described in Example 18, below, is a monomer. It is also a fusion or chimeric protein because the E. coli expression cloning method adds polylinker sequence and a histidine tag to the expressed protein that do not exist in the native protein. The Tumstatin fragment "Tumstatin N-53," also described in Example 18, is a fragment and a deletion mutant of the full-length Tumstatin protein, and when made by the same E. coli expression cloning method, also has additional sequences added to it, and is therefore a fusion or chimeric mutant fragment of the full-length Tumstatin protein. Subunits of this Tumstatin N-53, when combined together, e.g., into a dimer, trimer, etc., would produce a multimeric fusion of chimeric mutant fragment of the Tumstatin protein.

Encompassed by the present invention are proteins that have substantially the same amino acid sequence as Arresten, Canstatin or Tumstatin, or polynucleotides that have substantially the same nucleic acid sequence as the polynucleotides encoding Arresten, Canstatin or Tumstatin. "Substantially the same sequence" means a nucleic acid or polypeptide that exhibits at least about 70% sequence identity with a reference sequence, e.g., another nucleic acid or polypeptide, typically at least about 80% sequence identity with the reference sequence, preferably at least about 90% sequence identity, more preferably at least about 95% identity, and most preferably at least about 97% sequence identity with the reference sequence. The length of comparison for sequences will generally be at least 75 nucleotide bases or 25 amino acids, more preferably at least 150 nucleotide bases or 50 amino acids, and most preferably 243–264 nucleotide bases or 81–88 amino acids. "Polypeptide" as used herein indicates a molecular chain of amino acids and does not refer to a specific length of the product. Thus, peptides, oligopeptides and proteins are included within the definition of polypeptide. This term is also intended to include polypeptide that have been subjected to post-expression modifications such as, for example, glycosylations, acetylations, phosphorylations and the like.

"Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length) of the positions in two peptide or compound sequences are identical, then the two sequences are 50% identical; if 90% of the positions, e.g., 9 of 10 are matched, the two sequences share 90% sequence identity. By way of example, the amino acid sequences $R_2R_5R_7R_{10}R_6R_3$ and $R_9R_8R_1R10R_6R_3$ have 3 of 6 positions in common, and therefore share 50% sequence identity, while the sequences $R_2R_5R_7R_{10}R_6R_3$ and $R_8R_1R_{10}R_6R_3$ have 3 of 5 positions in common, a therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_2R_5R_7R_{10}R_6R_3$ and $R_2R_5R_7R_{10}R_3$ have 5 out of 6 positions in common, and therefore share 83.3% sequence identity.

Identity is often measured using sequence analysis software e.g., BLASTN or BLASTP (available at http://www.ncbi.nlm.nih.gov/BLAST/). The default parameters for comparing two sequences (e.g., "Blast"-ing two sequences against each other, http://www.ncbi.nlm.nih.gov/gorf/b12.html) by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1.

When two sequences share "sequence homology," it is meant that the two sequences differ from each other only by conservative substitutions. For polypeptide sequences, such conservative substitutions consist of substitution of one amino acid at a given position in the sequence for another amino acid of the same class (e.g., amino acids that share characteristics of hydrophobicity, charge, pK or other conformational or chemical properties, e.g., valine for leucine, arginine for lysine), or by one or more non-conservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one nonpolar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another; or the use of a chemically derivatized residue in place of a non-derivatized residue; provided that the polypeptide displays the requisite biological activity. Two sequences which share sequence homology may called "sequence homologs."

Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also encompassed by the present invention are chemical derivatives of Arresten, Canstatin and Tumstatin. "Chemical derivative" refers to a subject polypeptide having one or more residues chemically derivatized by reaction of a functional side group. Such derivatized residues include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substitute for lysine; 3-methylhistidine may be substituted for histidine; homoserine may be substituted for serine; and ornithine may be substituted for lysine.

The present invention also includes fusion proteins and chimeric proteins comprising the anti-angiogenic proteins, their fragments, mutants, homologs, analogs, and allelic variants. A fusion or chimeric protein can be produced as a result of recombinant expression and the cloning process, e.g., the protein may be produced comprising additional amino acids or amino acid sequences corresponding to full or partial linker sequences, e.g., the Arresten of the present invention, when produced in E. coli (see Example 2, below), comprises additional vector sequence added to the protein, including a histidine tag. As used herein, the term "fusion or chimeric protein" is intended to encompass changes of this type to the original protein sequence. Similar changes were made to the Canstatin and Tumstatin proteins (Examples 11 and 18, respectively). A fusion or chimeric protein can consist of a multimer of a single protein, e.g., repeats of the anti-angiogenic proteins, or the fusion and chimeric proteins can be made up of several proteins, e.g., several of the anti-angiogenic proteins. The fusion or chimeric protein can comprise a combination of two or more known anti-angiogenic proteins (e.g., angiostatin and endostatin, or biologically active fragments of angiostatin and endostatin), or an anti-angiogenic protein in combination with a targeting agent (e.g., endostatin with epidermal growth factor (EGF) or RGD peptides), or an anti-angiogenic protein in combination with an immunoglobulin molecule (e.g., endostatin and IgG, specifically with the Fc portion removed). The fusion and chimeric proteins can also include the anti-angiogenic proteins, their fragments, mutants, homologs, analogs, and allelic variants, and other anti-angiogenic proteins, e.g., endostatin, or angiostatin. Other anti-angiogenic proteins can include restin and apomigren; (WO99/29856, the teachings of which are herein incorporated by reference) and fragments of endostatin (WO99/29855, the teachings of which are herein incorporated by reference). The term "fusion protein" or "chimeric protein" as used herein can also encompass additional components for e.g., delivering a chemotherapeutic agent, wherein a polynucleotide encoding the chemotherapeutic agent is linked to the polynucleotide encoding the anti-angiogenic protein. Fusion or chimeric proteins can also encompass multimers of an anti-angiogenic protein, e.g., a dimer or trimer. Such fusion or chimeric proteins can be linked together via post-translational modification (e.g., chemically linked), or the entire fusion protein may be made recombinantly.

Multimeric proteins comprising Arresten, Canstatin, Tumstatin, their fragments, mutants, homologs, analogs and allelic variants are also intended to be encompassed by the present invention. By "multimer" is meant a protein comprising two or more copies of a subunit protein. The subunit protein may be one of the proteins of the present invention, e.g., Arresten repeated two or more times, or a fragment, mutant, homolog, analog or allelic variant, e.g., a Tumstatin mutant or fragment, e.g., Tumstatin 333, repeated two or more times. Such a multimer may also be a fusion or chimeric protein, e.g., a repeated tumstatin mutant may be combined with polylinker sequence, and/or one or more anti-angiogenic peptides, which may be present in a single copy, or may also be tandemly repeated, e.g., a protein may comprise two or more multimers within the overall protein.

The invention also encompasses a composition comprising one or more isolated polynucleotide(s) encoding Arresten, Canstatin or Tumstatin, as well as vectors and host cells containing such a polynucleotide, and processes for producing Arresten, Canstatin and Tumstatin, and their fragments, mutants, homologs, analogs and allelic variants. The term "vector" as used herein means a carrier into which pieces of nucleic acid may be inserted or cloned, which carrier functions to transfer the pieces of nucleic acid into a host cell. Such a vector may also bring about the replication and/or expression of the transferred nucleic acid pieces. Examples of vectors include nucleic acid molecules derived, e.g., from a plasmid, bacteriophage, or mammalian, plant or insect virus, or non-viral vectors such as ligand-nucleic acid conjugates, liposomes, or lipid-nucleic acid complexes. It may be desirable that the transferred nucleic molecule is operatively linked to an expression control sequence to form an expression vector capable of expressing the transferred nucleic acid. Such transfer of nucleic acids is generally called "transformation," and refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome. "Operably linked" refers to a situation wherein the components described are in a relationship permitting them to function in their intended manner, e.g., a control sequence "operably linked" to a coding sequence is ligated in such a manner that expression of the coding sequence is achieved under conditions compatible with the control sequence. A "coding sequence" is a polynucleotide sequence which is transcribed into mRNA and translated into a polypeptide when placed under the control of (e.g., operably linked to) appropriate regulatory sequences. The boundaries of the coding sequence are determined by a translation start codon at the 5'-terminus and a translation stop codon at the 3'-terminus. Such boundaries can be naturally-occurring, or can be introduced into or added the polynucleotide sequence by methods known in the art. A coding sequence can include, but is not limited to, mRNA, cDNA, and recombinant polynucleotide sequences.

The vector into which the cloned polynucleotide is cloned may be chosen because it functions in a prokaryotic, or alternatively, it is chosen because it functions in a eukaryotic organism. Two examples of vectors which allow for both the cloning of a polynucleotide encoding the Arresten, Canstatin and Tumstatin protein, and the expression of those proteins from the polynucleotides, are the pET22b and pET28(a) vectors (Novagen, Madison, Wis., USA) and a modified pPICZαA vector (InVitrogen, San Diego, Calif., USA), which allow expression of the protein in bacteria and yeast, respectively. (See for example, WO99/29878, the teachings which are hereby incorporated by reference).

Once a polynucleotide has been cloned into a suitable vector, it can be transformed into an appropriate host cell. By "host cell" is meant a cell which has been or can be used as the recipient of transferred nucleic acid by means of a vector. Host cells can prokaryotic or eukaryotic, mammalian, plant, or insect, and can exist as single cells, or as a collection, e.g., as a culture, or in a tissue culture, or in a tissue or an organism. Host cells can also be derived from normal or diseased tissue from a multicellular organism, e.g., a mammal. Host cell, as used herein, is intended to include not only the original cell which was transformed with a nucleic acid, but also descendants of such a cell, which still contain the nucleic acid.

In one embodiment, the isolated polynucleotide encoding the anti-angiogenic protein additionally comprises a polynucleotide linker encoding a peptide. Such linkers are known to those of skill in the art and, for example the linker can comprise at least one additional codon encoding at least one additional amino acid. Typically the linker comprises one to about twenty or thirty amino acids. The polynucleotide linker is translated, as is the polynucleotide encoding the anti-angiogenic protein, resulting in the expression of an anti-angiogenic protein with at least one additional amino acid residue at the amino or carboxyl terminus of the anti-angiogenic protein. Importantly, the additional amino acid, or amino acids, do not compromise the activity of the anti-angiogenic protein.

After inserting the selected polynucleotide into the vector, the vector is transformed into an appropriate prokaryotic strain and the strain is cultured (e.g., maintained) under suitable culture conditions for the production of the biologically active anti-angiogenic protein, thereby producing a biologically active anti-angiogenic protein, or mutant, derivative, fragment or fusion protein thereof. In one embodiment, the invention comprises cloning of a polynucleotide encoding an anti-angiogenic protein into the vectors pET22b, pET17b or pET28a, which are then transformed into bacteria. The bacterial host strain then expresses the anti-angiogenic protein. Typically the anti-angiogenic proteins are produced in quantities of about 10–20 milligrams, or more, per liter of culture fluid.

In another embodiment of the present invention, the eukaryotic vector comprises a modified yeast vector. One method is to use a pPICzα plasmid wherein the plasmid contains a multiple cloning site. The multiple cloning site has inserted into the multiple cloning site a His.Tag motif. Additionally the vector can be modified to add a NdeI site, or other suitable restriction sites. Such sites are well known to those of skill in the art. Anti-angiogenic proteins produced by this embodiment comprise a histidine tag motif (His.tag) comprising one, or more histidines, typically about 5–20 histidines. The tag must not interfere with the anti-angiogenic properties of the protein.

One method of producing Arresten, Canstatin or Tumstatin, for example, is to amplify the polynucleotide of SEQ ID NO:1, SEQ ID NO:5, or SEQ ID NO:9, respectively, and clone it into an expression vector, e.g., pET22b, pET28(a), pPICZαA, or some other expression vector, transform the vector containing the polynucleotide into a host cell capable of expressing the polypeptide encoded by the polynucleotide, culturing the transformed host cell under culture conditions suitable for expressing the protein, and then extracting and purifying the protein from the culture. Exemplary methods of producing anti-angiogenic proteins in general, and Arresten, Canstatin and Tumstatin in particular, are provided in the Examples below. The Arresten, Canstatin or Tumstatin protein may also be expressed as a product of transgenic animals, e.g., as a component of the milk of transgenic cows, goats, sheep or pigs, or as a product of a transgenic plant, e.g., combined or linked with starch molecules in maize.

Arresten, Canstatin or Tumstatin may also be produced by conventional, known methods of chemical synthesis. Methods for constructing the proteins of the present invention by synthetic means are known to those skilled in the art. The synthetically-constructed Arresten, Canstatin or Tumstatin protein sequences, by virtue of sharing primary, secondary or tertiary structural and/or conformational characteristics with e.g., recombinantly-produced Arresten, Canstatin or Tumstatin, may possess biological properties in common therewith, including biological activity. Thus, the synthetically-constructed Arresten, Canstatin or Tumstatin protein sequences may be employed as biologically active or immunological substitutes for e.g., recombinantly-produced, purified Arresten, Canstatin or Tumstatin protein in screening of therapeutic compounds and in immunological processes for the development of antibodies.

The Arresten, Canstatin and Tumstatin proteins are useful in inhibiting angiogenesis, as determined in standard assays, and provided in the Examples below. Arresten, Canstatin or Tumstatin do not inhibit the growth of other cell types, e.g., non-endothelial cells.

Polynucleotides encoding Arresten, Canstatin or Tumstatin can be cloned out of isolated DNA or a cDNA library. Nucleic acids and polypeptides, referred to herein as "isolated" are nucleic acids or polypeptides substantially free (i.e., separated away from) the material of the biological source from which they were obtained (e.g., as exists in a mixture of nucleic acids or in cells), which may have undergone further processing. "Isolated" nucleic acids or polypeptides include nucleic acids or polypeptides obtained by methods described herein, similar methods, or other suitable methods, including essentially pure nucleic acids or polypeptides, nucleic acids or polypeptides produced by chemical synthesis, by combinations of chemical or biological methods, and recombinantly produced nucleic acids or polypeptides which are isolated. An isolated polypeptide therefore means one which is relatively free of other proteins, carbohydrates, lipids, and other cellular components with which it is normally associated. An isolated nucleic acid is not immediately contiguous with (i.e., covalently linked to) both of the nucleic acids with which it is immediately contiguous in the naturally-occurring genome of the organism from which the nucleic acid is derived. The term, therefore, includes, for example, a nucleic acid which is incorporated into a vector (e.g., an autonomously replicating virus or plasmid), or a nucleic acid which exists as a separate molecule independent of other nucleic acids such as a nucleic acid fragment produced by chemical means or restriction endonuclease treatment.

The polynucleotides and proteins of the present invention can also be used to design probes to isolate other anti-angiogenic proteins. Exceptional methods are provided in U.S. Pat. No. 5,837,490, by Jacobs et al., the entire teachings of which are herein incorporated by reference in their entirety. The design of the oligonucleotide probe should preferably follow these parameters: (a) it should be designed to an area of the sequence which has the fewest ambiguous bases ("N's"), if any, and (b) It should be designed to have a $T_m$ of approx. 80° C. (assuming 2° C. for each A or T and 4 degrees for each G or C).

The oligonucleotide should preferably be labeled with g-$^{32}$P-ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4×10$^6$ dpm/pmole. The bacterial culture containing the pool of full-length clones should preferably be thawed and 100 µl of the stock used to inoculate a sterile culture flask containing 25 ml of sterile L-broth containing ampicillin at 100 µg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 µg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them. Highly stringent condition are those that are at least as stringent as, for example, 1×SSC at 65° C., or 1×SSC and 50% formamide at 42° C. Moderate stringency conditions are those that are at least as stringent as 4×SSC at 65° C., or 4×SSC and 50% formamide at 42° C. Reduced stringency conditions are those that are at least as stringent as 4×SSC at 50° C., or 6×SSC and 50% formamide at 40° C.

The filter is then preferably incubated at 65° C. for 1 hour with gentle agitation in 6×. SSC (20× stock is 175.3 g NaCl/liter, 88.2 g Na citrate/liter, adjusted to pH 7.0 with NaOH) containing 0.5% SDS, 100 µg/ml of yeast RNA, and 10 mM EDTA (approximately 10 mL per 150 mm filter). Preferably, the probe is then added to the hybridization mix at a concentration greater than or equal to 1×10$^6$ dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed. The positive colonies are then picked, grown in culture, and plasmid DNA isolated using standard procedures. The clones can then be verified by restriction analysis, hybridization analysis, or DNA sequencing.

The present invention includes methods of inhibiting angiogenesis in mammalian tissue using Arresten, Canstatin, Tumstatin or their biologically-active fragments, analogs, homologs, derivatives or mutants. In particular, the present invention includes methods of treating an angiogenesis-mediated disease with an effective amount of one or more of the anti-angiogenic proteins, or one or more biologically active fragment thereof, or combinations of fragments that possess anti-angiogenic activity, or agonists and antagonists. An effective amount of anti-angiogenic protein is an amount sufficient to inhibit the angiogenesis which results in the disease or condition, thus completely, or partially, alleviating the disease or condition. Alleviation of the angiogenesis-mediated disease can be determined by observing an alleviation of symptoms of the disease, e.g., a reduction in the size of a tumor, or arrested tumor growth. As used herein, the term "effective amount" also means the total amount of each active component of the composition or method that is sufficient to show a meaningful patient benefit, i.e., treatment, healing, prevention or amelioration of the relevant medical condition, or an increase in rate of treatment, healing, prevention or amelioration of such conditions. When applied to a combination, the term refers to combined amounts of the active ingredients that result in the therapeutic effect, whether administered in combination, serially or simultaneously. Angiogenesis-mediated diseases include, but are not limited to, cancers, solid tumors, blood-born tumors (e.g., leukemias), tumor metastasis, benign tumors (e.g., hemangiomas, acoustic neuromas, neurofibromas, trachomas, and pyogenic granulomas), rheumatoid arthritis, psoriasis, ocular angiogenic diseases (e.g., diabetic retinopathy, retinopathy of prematurity, macular degeneration, corneal graft rejection, neovascular glaucoma, retrolental fibroplasia, rubeosis), Osler-Webber Syndrome, myocardial angiogenesis, plaque neovascularization, telangiectasia, hemophiliac joints, angiofibroma, and wound granulation. The anti-angiogenic proteins are useful in the treatment of diseases of excessive or abnormal stimulation of endothelial cells. These diseases include, but are not limited to, intestinal adhesions, Crohn's disease, atherosclerosis, scleroderma, and hypertrophic scars (i.e., keloids). The anti-angiogenic proteins can be used as a birth control agent by preventing vascularization required for embryo implantation. The anti-angiogenic proteins are useful in the treatment of diseases that have angiogenesis as a pathologic consequence such as cat scratch disease (*Rochele minalia quintosa*) and ulcers (*Heliobacter pylori*). The anti-angiogenic proteins can also be used to prevent dialysis graft vascular access stenosis, and obesity, e.g., by inhibiting capillary formation in adipose tissue, thereby preventing its expansion. The anti-angiogenic proteins can also be used to treat localized (e.g., nonmetastisized) diseases. "Cancer" means neoplastic growth, hyperplastic or proliferative growth or a pathological state of abnormal cellular development and includes solid tumors, non-solid tumors, and any abnormal cellular proliferation, such as that seen in leukemia. As used herein, "cancer" also means angiogenesis-dependent cancers and tumors, i.e., tumors that require for their growth (expansion in volume and/or mass) an increase in the number and density of the blood vessels supplying them with blood. "Regression" refers to the reduction of tumor mass and size as determined using methods well-known to those of skill in the art.

Alternatively, where an increase in angiogenesis is desired, e.g., in wound healing, or in post-infarct heart tissue, antibodies or antisera to the anti-angiogenic proteins can be used to block localized, native anti-angiogenic proteins and processes, and thereby increase formation of new blood vessels so as to inhibit atrophy of tissue.

The anti-angiogenic proteins may be used in combination with other compositions and procedures for the treatment of diseases. For example, a tumor may be treated conventionally with surgery, radiation, chemotherapy, or immunotherapy, combined with the anti-angiogenic proteins and then the anti-angiogenic proteins may be subsequently administered to the patient to extend the dormancy of micrometastases and to stabilize and inhibit the growth of any residual primary tumor. The anti-angiogenic proteins, or fragments, antisera, receptor agonists, or receptor antagonists thereof, or combinations thereof, can also be combined with other anti-angiogenic compounds, or proteins, fragments, antisera, receptor agonists, receptor antagonists of other anti-angiogenic proteins (e.g., angiostatin, endostatin). Additionally, the anti-angiogenic proteins, or their fragments, antisera, receptor agonists, receptor antagonists, or combinations thereof, are combined with pharmaceutically acceptable excipients, and optionally sustained-release matrix, such as biodegradable polymers, to form therapeutic compositions. The compositions of the present invention may also contain other anti-angiogenic proteins or chemical compounds, such as endostatin or angiostatin, and mutants, fragments, and analogs thereof. The compositions may further contain other agents which either enhance the activity of the protein or compliment its activity or use in treatment, such as chemotherapeutic or radioactive agents. Such additional factors and/or agents may be included in the composition to produce a synergistic effect with protein of the invention, or to minimize side effects. Additionally, administration of the composition of the present invention may be administered concurrently with other therapies, e.g., administered in conjunction with a chemotherapy or radiation therapy regimen.

The invention includes methods for inhibiting angiogenesis in mammalian tissues by contacting the tissue with a composition comprising the proteins of the invention. By "contacting" is meant not only topical application, but also those modes of delivery that introduce the composition into the tissues, or into the cells of the tissues.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating composition of the present invention may be a solid, liquid or aerosol and may be administered by any known route of administration. Examples of solid compositions include pills, creams, and implantable dosage units. The pills may be administered orally, the therapeutic creams may be administered topically. The implantable dosage unit may be administered locally, for example at a tumor site, or which may be implanted for systemic release of the angiogenesis-modulating composition, for example subcutaneously. Examples of liquid composition include formulations adapted for injection subcutaneously, intravenously, intraarterially, and formulations for topical and intraocular administration. Examples of aerosol formulation include inhaler formulation for administration to the lungs.

The proteins and protein fragments with the anti-angiogenic activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the anti-angiogenic proteins may be incorporated into biodegradable polymers allowing for sustained release of the compound, the polymers being implanted in the vicinity of where drug delivery is desired, for example, at the site of a tumor or implanted so that the anti-angiogenic proteins are slowly released systemically. Osmotic minipumps may also be used to provide controlled delivery of high concentrations of the anti-angiogenic proteins through cannulae to the site of interest, such as directly into a metastatic growth or into the vascular supply to that tumor. The biodegradable polymers and their use are described, for example, in detail in Brem et al. (1991) (*J. Neurosurg.* 74:441–446), which is hereby incorporated by reference in its entirety.

The compositions containing a polypeptide of this invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

Modes of administration of the compositions of the present inventions include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyois (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polmer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The therapeutic compositions of the present invention can include pharmaceutically acceptable salts of the components therein, e.g., which may be derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences* (1977) 66:1 et seq., which is incorporated herein by reference. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

As used herein, the terms "pharmaceutically acceptable," "physiologically tolerable" and grammatical variations thereof as they refer to compositions, carriers, diluents and reagents, are used interchangeably and represent that the materials are capable of administration to or upon a mammal with a minimum of undesirable physiological effects such as nausea, dizziness, gastric upset and the like. The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The anti-angiogenic proteins of the present invention can also be included in a composition comprising a prodrug. As used herein, the term "prodrug" refers to compounds which are rapidly transformed in vivo to yield the parent compound, for example, by enzymatic hydrolysis in blood. A thorough discussion is provided in T. Higuchi and V. Stella, *Prodrugs as Novel Delivery Systems*, Vol. 14 of the ACS Symposium Series and in Edward B. Roche, ed., *Bioreversible Carriers in Drug Design*, American Pharmaceutical Association and Permagon Press, 1987, both of which are incorporated herein by reference. As used herein, the term "pharmaceutically acceptable prodrug" refers to (1) those prodrugs of the compounds of the present invention which are, within the scope of sound medical judgement, suitable for use in contact with the tissues of humans and animals without undue toxicity, irritation, allergic response and the like, commensurate with a suitable benefit-to-risk ratio and effective for their intended use and (2) zwitterionic forms, where possible, of the parent compound.

The dosage of the anti-angiogenic proteins of the present invention will depend on the disease state or condition being treated and other clinical factors such as weight and condition of the human or animal and the route of administration of the compound. For treating humans or animals, about 10 mg/kg of body weight to about 20 mg/kg of body weight of the protein can be administered. In combination therapies, e.g., the proteins of the invention in combination with radiotherapy, chemotherapy, or immunotherapy, it may be possible to reduce the dosage, e.g., to about 0.1 mg/kg of body weight to about 0.2 mg/kg of body weight. Depending upon the half-life of the anti-angiogenic proteins in the particular animal or human, the anti-angiogenic proteins can be administered between several times per day to once a week. It is to be understood that the present invention has application for both human and veterinary use. The methods of the present invention contemplate single as well as multiple administrations, given either simultaneously or over an extended period of time. In addition, the anti-angiogenic proteins can be administered in conjunction with other forms of therapy, e.g., chemotherapy, radiotherapy, or immunotherapy.

The anti-angiogenic protein formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The anti-angiogenic protein formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

When an effective amount of protein of the present invention is administered orally, the anti-angiogenic proteins of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When an effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with the anti-angiogenic proteins, or biologically functional protein fragments thereof, to provide dual therapy to the patient.

The therapeutic compositions are also presently valuable for veterinary applications. Particularly domestic animals and thoroughbred horses, in addition to humans, are desired patients for such treatment with proteins of the present invention.

Cytotoxic agents such as ricin, can be linked to the anti-angiogenic proteins, and fragments thereof, thereby providing a tool for destruction of cells that bind the anti-angiogenic proteins. These cells may be found in many locations, including but not limited to, micrometastases and primary tumors. Proteins linked to cytotoxic agents are infused in a manner designed to maximize delivery to the desired location. For example, ricin-linked high affinity fragments are delivered through a cannula into vessels supplying the target site or directly into the target. Such agents are also delivered in a controlled manner through osmotic pumps coupled to infusion cannulae. A combination of antagonists to the anti-angiogenic proteins may be co-applied with stimulators of angiogenesis to increase vascularization of tissue. This therapeutic regimen provides an effective means of destroying metastatic cancer.

Additional treatment methods include administration of the anti-angiogenic proteins, fragments, analogs, antisera, or receptor agonists and antagonists thereof, linked to cytotoxic agents. It is to be understood that the anti-angiogenic proteins can be human or animal in origin. The anti-angiogenic proteins can also be produced synthetically by chemical reaction or by recombinant techniques in conjunction with expression systems. The anti-angiogenic proteins can also be produced by enzymatically cleaving isolated Type IV collagen to generate proteins having anti-angiogenic activity. The anti-angiogenic proteins may also be produced by compounds that mimic the action of endogenous enzymes that cleave Type IV collagen to the anti-angiogenic proteins. Production of the anti-angiogenic proteins may also be modulated by compounds that affect the activity of cleavage enzymes.

The present invention also encompasses gene therapy whereby a polynucleotide encoding the anti-angiogenic proteins, or a mutant, fragment, or fusion protein thereof, is introduced and regulated in a patient. Various methods of transferring or delivering DNA to cells for expression of the gene product protein, otherwise referred to as gene therapy, are disclosed in *Gene Transfer into Mammalian Somatic Cells in vivo*, N. Yang (1992) *Crit. Rev. Biotechn.* 12(4):335–356, which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene such as that encoding one or more of the anti-angiogenic proteins may be placed in a patient and thus prevent occurrence of angiogenesis; or a gene that makes tumor cells more susceptible to radiation could be inserted and then radiation of the tumor would cause increased killing of the tumor cells.

Many protocols for transfer of the DNA or regulatory sequences of the anti-angiogenic proteins are envisioned in this invention. Transfection of promoter sequences, other than one normally found specifically associated with the anti-angiogenic proteins, or other sequences which would increase production of the anti-angiogenic proteins are also envisioned as methods of gene therapy. An example of this technology is found in Transkaryotic Therapies, Inc., of Cambridge, Mass., using homologous recombination to insert a "genetic switch" that turns on an erythropoietin gene in cells. See *Genetic Engineering News*, Apr. 15, 1994. Such "genetic switches" could be used to activate the anti-angiogenic proteins (or their receptors) in cells not normally expressing those proteins (or receptors).

Gene transfer methods for gene therapy fall into three broad categories: physical (e.g., electroporation, direct gene transfer and particle bombardment), chemical (e.g., lipid-based carriers, or other non-viral vectors) and biological (e.g., virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of the DNA or regulatory sequences controlling production of the anti-angiogenic proteins.

Chemical methods of gene therapy may involve a lipid based compound, not necessarily a liposome, to transfer the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct the tissue-specific expression of foreign genes, cis-acting regulatory elements or promoters that are known to be tissue-specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product proteins at high levels. Adenoviral vectors have high efficiencies of infectivity, even with low titers of virus. Additionally, the virus is fully infective as a cell free virion so injection of producer cell lines is not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Electroporation for gene transfer uses an electrical current to make cells or tissues susceptible to electroporation-mediated mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site-specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of the anti-angiogenic proteins may be accomplished by administering compounds that bind to the gene encoding one of the anti-angiogenic proteins, or control regions associated with the gene, or its corresponding RNA transcript to modify the rate of transcription or translation. Additionally, cells transfected with a DNA sequence encoding the anti-angiogenic proteins may be administered to a patient to provide an in vivo source of those proteins. For example, cells may be transfected with a vector containing a nucleic acid sequence encoding the anti-angiogenic proteins. The transfected cells may be cells derived from the patient's normal tissue, the patient's diseased tissue, or may be non-patient cells.

For example, tumor cells removed from a patient can be transfected with a vector capable of expressing the proteins of the present invention, and re-introduced into the patient. The transfected tumor cells produce levels of the protein in the patient that inhibit the growth of the tumor. Patients may be human or non-human animals. Cells may also be transfected by non-vector, or physical or chemical methods known in the art such as electroporation, ionoporation, or via a "gene gun." Additionally, the DNA may be directly injected, without the aid of a carrier, into a patient. In particular, the DNA may be injected into skin, muscle or blood.

The gene therapy protocol for transfecting the anti-angiogenic proteins into a patient may either be through integration of the anti-angiogenic protein DNA into the genome of the cells, into minichromosomes or as a separate replicating or non-replicating DNA construct in the cytoplasm or nucleoplasm of the cell. Expression of the anti-angiogenic proteins may continue for a long-period of time or may be reinjected periodically to maintain a desired level of the protein(s) in the cell, the tissue or organ or a determined blood level.

In addition, the invention encompasses antibodies and antisera, which can be used for testing of novel anti-angiogenic proteins, and can also be used in diagnosis, prognosis, or treatment of diseases and conditions characterized by, or associated with, angiogenic activity or lack thereof. Such antibodies and antisera can also be used to up-regulate angiogenesis where desired, e.g., in post-infarct heart tissue, antibodies or antisera to the proteins of the invention can be used to block localized, native anti-angiogenic proteins and processes, and increase formation of new blood vessels and inhibit atrophy of heart tissue.

Such antibodies and antisera can be combined with pharmaceutically-acceptable compositions and carriers to form diagnostic, prognostic or therapeutic compositions. The term "antibody" or "antibody molecule" refers to a population of immunoglobulin molecules and/or immunologically active portions of immunoglobulin molecules, i.e., molecules that contain an antibody combining site or paratope.

Passive antibody therapy using antibodies that specifically bind the anti-angiogenic proteins can be employed to modulate angiogenic-dependent processes such as reproduction, development, and wound healing and tissue repair. In addition, antisera directed to the Fab regions of antibodies of the anti-angiogenic proteins can be administered to block the ability of endogenous antisera to the proteins to bind the proteins.

The the anti-angiogenic proteins of the present invention also can be used to generate antibodies that are specific for the inhibitor(s) and receptor(s). The antibodies can be either polyclonal antibodies or monoclonal antibodies. These antibodies that specifically bind to the anti-angiogenic proteins or their receptors can be used in diagnostic methods and kits that are well known to those of ordinary skill in the art to detect or quantify the anti-angiogenic proteins or their receptors in a body fluid or tissue. Results from these tests can be used to diagnose or predict the occurrence or recurrence of a cancer and other angiogenic mediated diseases.

The invention also includes use of the anti-angiogenic proteins, antibodies to those proteins, and compositions comprising those proteins and/or their antibodies in diagnosis or prognosis of diseases characterized by angiogenic activity. As used herein, the term "prognostic method" means a method that enables a prediction regarding the progression of a disease of a human or animal diagnosed with the disease, in particular, an angiogenesis dependent disease. The term "diagnostic method" as used herein means a method that enables a determination of the presence or type of angiogenesis-dependent disease in or on a human or animal.

The the anti-angiogenic proteins can be used in a diagnostic method and kit to detect and quantify antibodies capable of binding the proteins. These kits would permit detection of circulating antibodies to the anti-angiogenic proteins which indicates the spread of micrometastases in the presence of the anti-angiogenic proteins secreted by primary tumors in situ. Patients that have such circulating anti-protein antibodies may be more likely to develop multiple tumors and cancers, and may be more likely to have recurrences of cancer after treatments or periods of remission. The Fab fragments of these anti-protein antibodies may be used as antigens to generate anti-protein Fab-fragment antisera which can be used to neutralize anti-protein antibodies. Such a method would reduce the removal of circulating protein by anti-protein antibodies, thereby effectively elevating circulating levels of the anti-angiogenic proteins.

The present invention also includes isolation of receptors specific for the anti-angiogenic proteins. Protein fragments that possess high affinity binding to tissues can be used to isolate the receptor of the anti-angiogenic proteins on affinity columns. Isolation and purification of the receptor(s) is a fundamental step towards elucidating the mechanism of action of the anti-angiogenic proteins. Isolation of a receptor and identification of agonists and antagonists will facilitate development of drugs to modulate the activity of the receptor, the final pathway to biological activity. Isolation of the receptor enables the construction of nucleotide probes to monitor the location and synthesis of the receptor, using in situ and solution hybridization technology. Further, the gene for the receptor can be isolated, incorporated into an expression vector and transfected into cells, such as patient tumor cells to increase the ability of a cell type, tissue or tumor to bind the anti-angiogenic proteins and inhibit local angiogenesis.

The anti-angiogenic proteins are employed to develop affinity columns for isolation of the receptor(s) for the anti-angiogenic proteins from cultured tumor cells. Isolation and purification of the receptor is followed by amino acid sequencing. Using this information the gene or genes coding for the receptor can be identified and isolated. Next, cloned nucleic acid sequences are developed for insertion into vectors capable of expressing the receptor. These techniques are well known to those skilled in the art. Transfection of the nucleic acid sequence(s) coding for the receptor into tumor cells, and expression of the receptor by the transfected tumor cells enhances the responsiveness of these cells to endogenous or exogenous anti-angiogenic proteins and thereby decreasing the rate of metastatic growth.

Angiogenesis-inhibiting proteins of the present invention can be synthesized in a standard microchemical facility and purity checked with HPLC and mass spectrophotometry. Methods of protein synthesis, HPLC purification and mass spectrophotometry are commonly known to those skilled in these arts. The anti-angiogenic proteins and their receptors proteins are also produced in recombinant E. coli or yeast expression systems, and purified with column chromatography.

Different protein fragments of the intact the anti-angiogenic proteins can be synthesized for use in several applications including, but not limited to the following; as antigens for the development of specific antisera, as agonists and antagonists active at binding sites of the anti-angiogenic proteins, as proteins to be linked to, or used in combination with, cytotoxic agents for targeted killing of cells that bind the anti-angiogenic proteins.

The synthetic protein fragments of the anti-angiogenic proteins have a variety of uses. The protein that binds to the receptor(s) of the anti-angiogenic proteins with high specificity and avidity is radiolabeled and employed for visualization and quantitation of binding sites using autoradiographic and membrane binding techniques. This application provides important diagnostic and research tools. Knowledge of the binding properties of the receptor(s) facilitates investigation of the transduction mechanisms linked to the receptor(s).

The anti-angiogenic proteins and proteins derived from them can be coupled to other molecules using standard methods. The amino and carboxyl termini of the anti-angiogenic proteins both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. Alternatively, tyrosine or lysine is added to fragments that do not have these residues to facilitate labeling of reactive amino and hydroxyl groups on the protein. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

The anti-angiogenic proteins are chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of a protein of the present invention with $^{125}$I is accomplished using chloramine T and Na$^{125}$I of high specific activity. The reaction is terminated with sodium metabisulfite and the mixture is desalted on disposable columns. The labeled protein is eluted from the column and fractions are collected. Aliquots are removed from each fraction and radioactivity measured in a gamma counter. In this manner, the unreacted Na$^{125}$I is separated from the labeled protein. The protein fractions with the highest specific radioactivity are stored for subsequent use such as analysis of the ability to bind to antisera of the anti-angiogenic proteins.

In addition, labeling the anti-angiogenic proteins with short lived isotopes enables visualization of receptor binding sites in vivo using positron emission tomography or other modern radiographic techniques to locate tumors with the proteins' binding sites.

Systematic substitution of amino acids within these synthesized proteins yields high affinity protein agonists and antagonists to the receptor(s) of the anti-angiogenic proteins that enhance or diminish binding to the receptor(s). Such agonists are used to suppress the growth of micrometastases, thereby limiting the spread of cancer. Antagonists to the anti-angiogenic proteins are applied in situations of inadequate vascularization, to block the inhibitory effects of the anti-angiogenic proteins and promote angiogenesis. For example, this treatment may have therapeutic effects to promote wound healing in diabetics.

The invention is further illustrated by the following examples, which are not meant to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Isolation of Native Arresten

Arresten can be generated in milligram quantities from human placenta and amnion tissue. The protocol for isolating this and similar proteins has been described by others (e.g., Langeveld, J. P. et al., 1988, *J. Biol. Chem.* 263:10481–10488; Saus, J. et al., 1988, *J. Biol. Chem.* 263:13374–13380; Gunwar, S. et al., 1990, *J. Biol. Chem.* 265:5466–5469; Gunwar S. et al., 1991, *J. Biol. Chem.* 266:15318–15324; Kahsai, T. Z. et al., 1997, *J. Biol. Chem.* 272:17023–17032). Production of the recombinant form of Arresten is described in Neilson et al. (1993, *J. Biol. Chem.* 268:8402–8406). The protein can also be expressed in 293 kidney cells (e.g., by the method described in Hohenester, E. et al., 1998, *EMBO J.* 17:1656–1664). Arresten can also be isolated according to the method of Pihlajaniemi, T. et al. (1985, *J. Biol. Chem.* 260:7681–7687).

The nucleotide (SEQ ID NO:1) and amino acid (SEQ ID NO:2) ("Arresten") sequence of the α1 chain of the NC1 domain of Type IV collagen are shown in FIG. 1. Arresten generally comprises the NC1 domain of the α1 chain of Type IV collagen, and possibly also the junction region, which are the 12 amino acids immediately before the NC1 domain.

Native Arresten was isolated from human placenta using bacterial collagenase, anion-exchange chromatography, gel filtration chromatography, HPLC, and affinity chromatography (Gunwar, S. et al., 1991, J. Biol. Chem. 266:15318–24; Weber, S. et al., 1984, Eur. J. Biochem. 139:401–10). Type IV collagen monomers isolated from human placenta were HPLC-purified using a C-18 hydrophobic column (Pharmacia, Piscataway, N.J., USA). The constituent proteins were resolved with an acetonitrile gradient (32%–39%). A major peak was visible, and a small double peak. SDS-PAGE analysis revealed two bands within the first peak, and no detectable proteins in the second peak. Immunoblotting, also found no immunodetectable protein in the second peak, and the major peak was identified as Arresten.

Example 2

Recombinant Production of Arresten in *E. coli*

The sequence encoding Arresten was amplified by PCR from the α1 NC1(IV)/pDS vector (Neilson, E. G. et al., 1993, J. Bio. Chem. 268:8402–5) using the forward primer 5'-CGG GAT CCT TCT GTT GAT CAC GGC TTC-3' (SEQ ID NO:3) and the reverse primer 5'-CCC AAG CTT TGT TCT TCT CAT ACA GAC-3' (SEQ ID NO:4). The resulting cDNA fragment was digested with BamHI and HindIII and ligated into predigested pET22b(+) (Novagen, Madison, Wis., USA). This construct is shown in FIG. 2. This placed Arresten downstream of and in frame with The pelB leader sequence, allowing for periplasmic localization and expression of soluble protein. Additional vector sequence was added to the protein encoding amino acids MDIGINSD (SEQ ID NO:13). The 3' end of the sequence was ligated in frame with the polyhistidine tag sequence. Additional vector sequence between the 3' end of the cDNA and the his-tag encoded the amino acids KLAAALE (SEQ ID NO:14). Positive clones were sequenced on both strands.

Plasmid constructs encoding Arresten were first transformed into *E. coli* HMS174 (Novagen, Madison, Wis., USA) and then transformed into BL21 (Novagen, Madison, Wis., USA) for expression. An overnight bacterial culture was used to inoculate a 500 ml culture of LB medium. This culture was grown for approximately four hours until the cells reached an $OD_{600}$ of 0.6. Protein expression was then induced by addition of IPTG to a final concentration of 1–2 mM. After a two-hour induction, cells were harvested by centrifugation at 5000×g and lysed by resuspension in 6 M guanidine, 0.1 M $NaH_2PO_4$, 0.01 M Tris-HCl (pH 8.0). Resuspended cells were sonicated briefly, and centrifuged at 12,000×g for 30 minutes. The supernatant fraction was passed over a 5 ml Ni-NTA agarose column (Qiagen, Hilden, Germany) four to six times at a speed of 2 ml per minute. Non-specifically bound protein was removed by washing with both 10 mM and 25 mM imidazole in 8 M urea, 0.1 M $NaH_2PO_4$, 0.01 M Tris-HCl (pH 8.0). Arresten protein was eluted from the column with increasing concentrations of imidazole (50 mM, 125 mM and 250 mM) in 8 M urea, 0.1 M $NaH_2PO_4$, 0.01 M Tris-HCl (pH 8.0). The eluted protein was dialyzed twice against PBS at 4° C. A minor portion of the total protein precipitated during dialysis. Dialyzed protein was collected and centrifuged at approximately 3500×g and separated into pellet and supernatant fractions. Protein concentration in each fraction was determined by the BCA assay (Pierce Chemical Co., Rockford, Ill., USA) and quantitative SDS-PAGE analysis. The fraction of total protein in the pellet was approximately 22%, with the remaining 78% recovered as a soluble protein. The total yield of protein was approximately 10 mg/liter.

The *E. coli*-expressed protein was isolated predominantly as a soluble protein, and SDS-PAGE revealed a monomeric band at 29 kDa. The additional 3 kDa arises from polylinker and histidine tag sequences and was immunodetected by both Arresten and 6-Histidine tag antibodies.

Example 3

Expression of Arresten in 293 Embryonic Kidney Cells

The pDS plasmid containing α1(IV) NC1 was used to amplify Arresten in a way that it would add a leader signal sequence in-frame into the pcDNA 3.1 eukaryotic expression vector (InVitrogen, San Diego, Calif., USA). The leader sequence from the 5' end of the full length α1(IV) chain was cloned 5' to the NC1 domain to enable protein secretion into the culture medium. The Arresten-containing recombinant vectors were sequenced using flanking primers. Error-free cDNA clones were further purified and used for in vitro translation studies to confirm protein expression. The Arresten-containing plasmid and control plasmid were used to transfect 293 cells using the calcium chloride method. Transfected clones were selected by geneticin antibiotic treatment (Life Technologies/Gibco BRL, Gaithersburg, Md., USA). The cells were passed for three weeks in the presence of the antibiotic until no cell death was evident. Clones were then expanded into T-225 flasks and grown until confluent. The supernatant was then collected and concentrated using an amicon concentrator (Amicon). The concentrated supernatant was analyzed by SDS-PAGE, immunoblotting and ELISA for Arresten expression. Strong binding in the supernatant was detected by ELISA. SDS-PAGE analysis revealed a single major band at about 30 kDa. Arresten-containing supernatant was subjected to affinity chromatography using Arresten-specific antibodies (Gunwar, S. et al., 1991, J. Biol. Chem. 266:15318–24). A major peak was identified, containing a monomer of about 30 kDa that was immunoreactive with Arresten antibodies. Approximately 1–2 mg of recombinant Arresten was produced per liter of culture fluid.

Example 4

Arresten Inhibits Endothelial Cell Proliferation

Figure 3A:
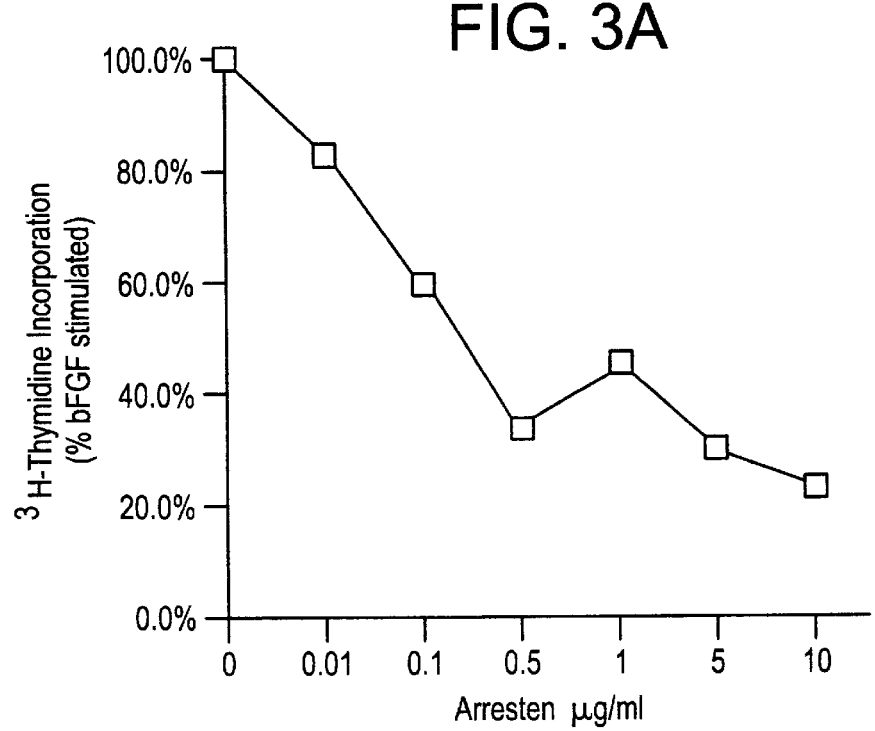
FIGS. 3A and 3B are a pair of line graphs showing the effects of Arresten (FIG. 3A, 0 μg/ml to 10 μg/ml, x-axis) and endostatin (FIG. 3B, 0 μg/ml to 10 μg/ml, x-axis) on $^3$H-thymidine incorporation (y-axis) as an indicator of endothelial cell (C-PAE) proliferation.
Figure 3B:
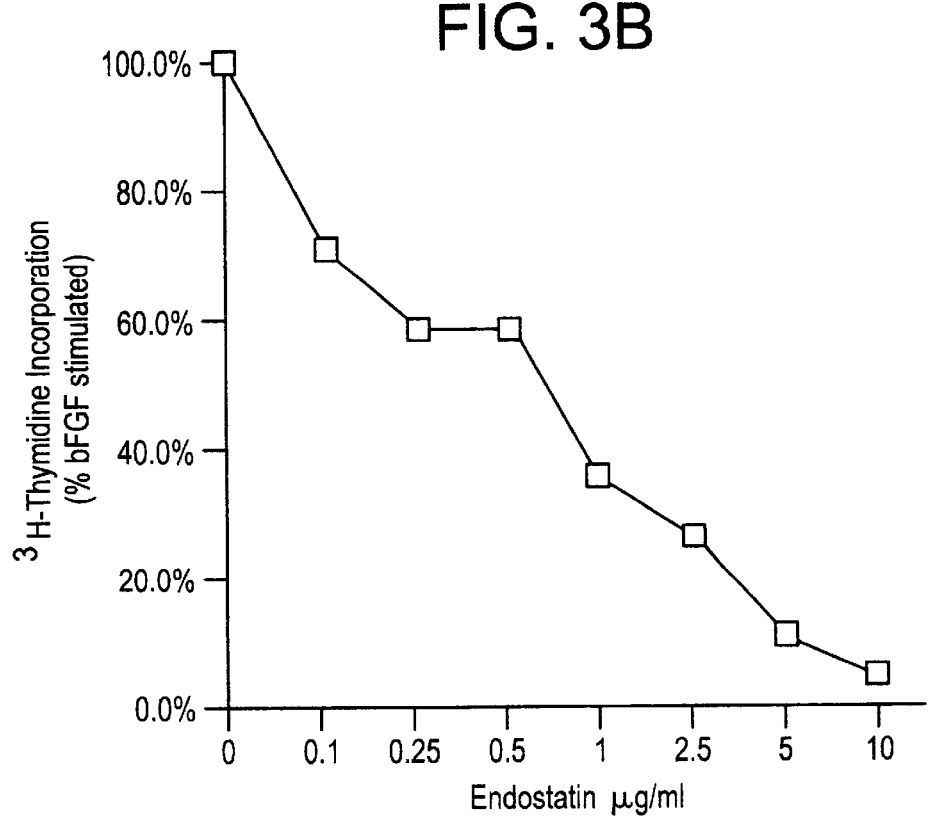
Figure 4A:
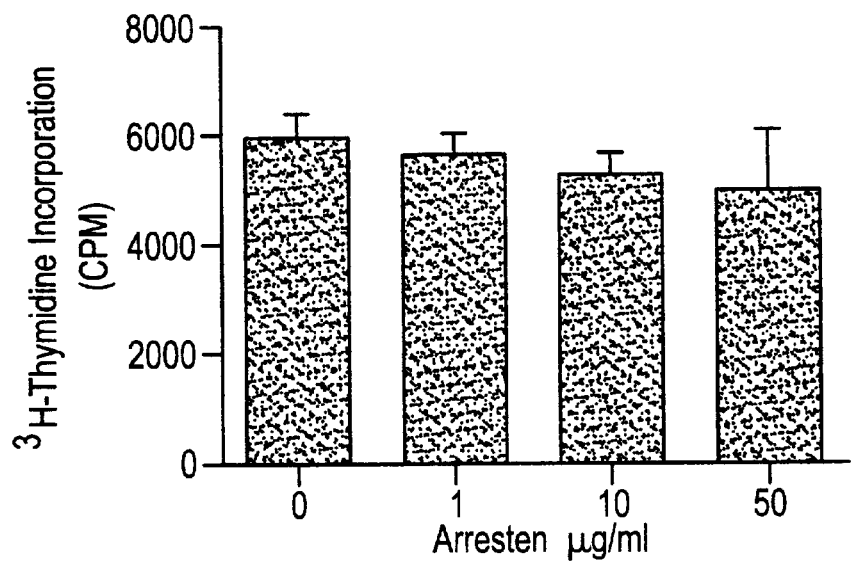
FIGS. 4A, 4B, 4C and 4D are a set of four bar charts showing the effect of Arresten and endostatin on $^3$H-thymidine incorporation (y-axis) as an indicator of endothelial cell proliferation.
Figure 4B:
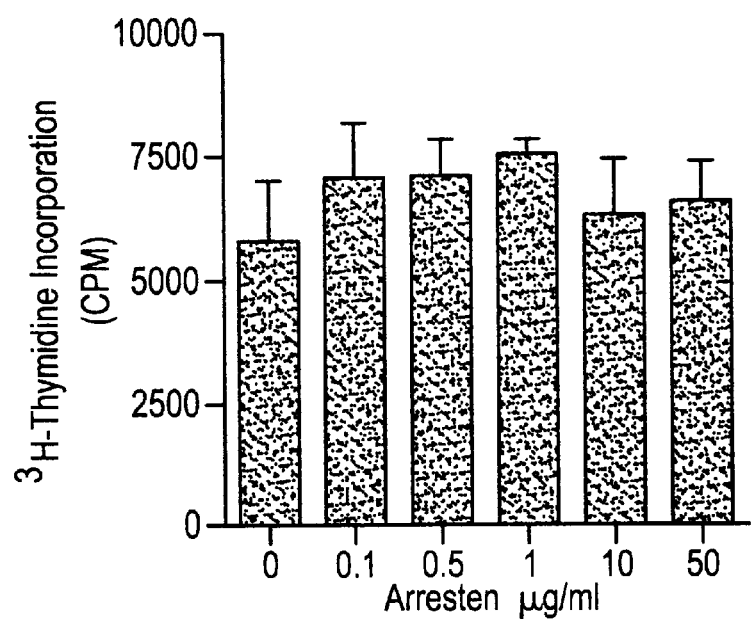
Figure 4C:
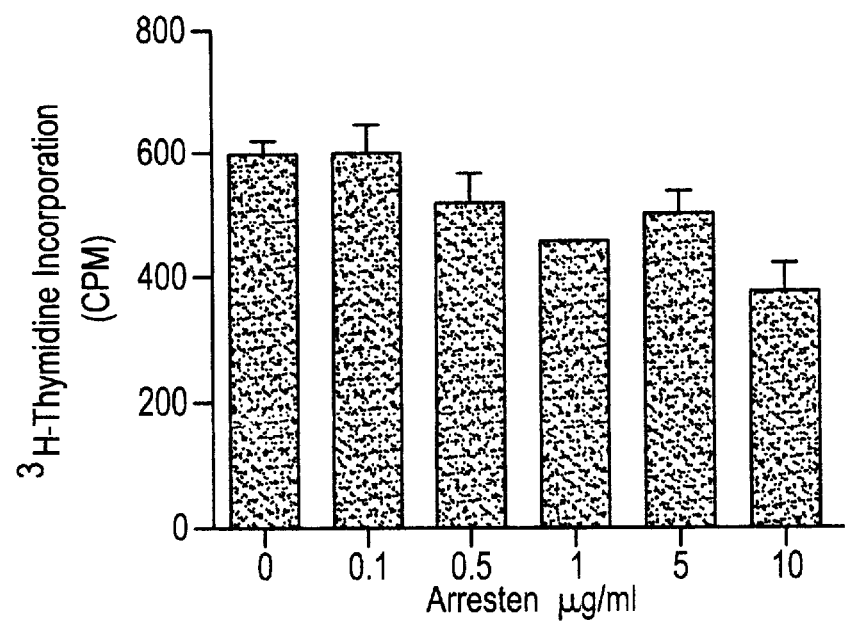
Figure 4D:
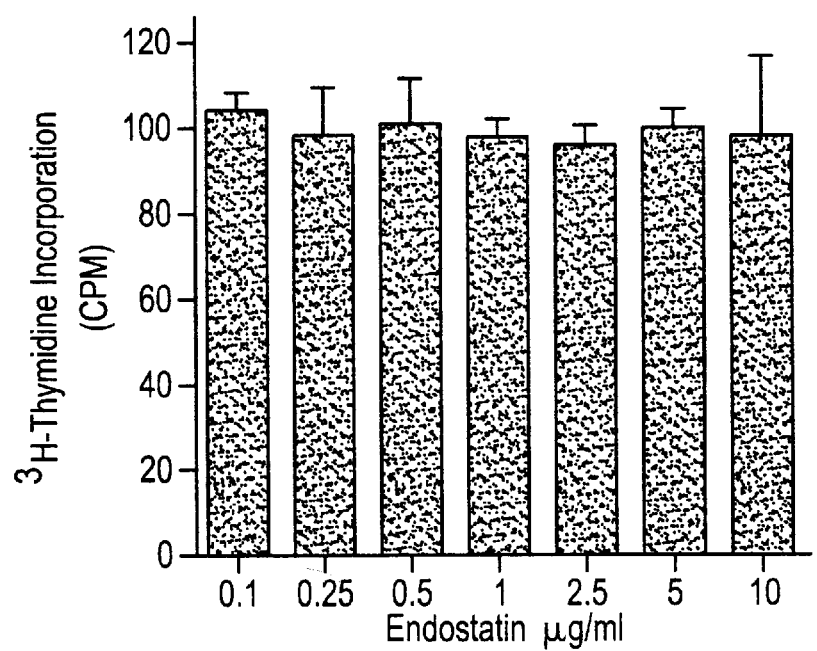

C-PAE cells were grown to confluence in DMEM with 10% fetal calf serum (FCS) and kept contact inhibited for 48 hours. Control cells were 786-O (renal carcinoma) cells, PC-3 cells, HPEC cells, and A-498 (renal carcinoma) cells. Cells were harvested with trypsinization (Life Technologies/Gibco BRL, Gaithersburg, Md., USA) at 37° C. for five minutes. A suspension of 12,500 cells in DMEM with 1% FCS was added to each well of a 24-well plate coated with 10 μg/ml fibronectin. The cells were incubated for 24 hours at 37° C. with 5% $CO_2$ and 95% humidity. Medium was removed and replaced with DMEM containing 0.5% FCS and 3 ng/ml bFGF (R&D Systems, Minneapolis, Minn., USA). Unstimulated controls received no bFGF. Cells were treated with concentrations of Arresten or endostatin ranging from 0.01 to 50 μg/ml. All wells received 1 μCurie of $^3$H-thymidine at the time of treatment. After 24 hours, medium was removed and the wells were washed with PBS. Cells were extracted with 1N NaOH and added to a scintillation vial containing 4 ml of ScintiVerse II (Fisher Scientific, Pittsburgh, Pa., USA) solution. Thymidine incorporation was measured using a scintillation counter. The results are shown in FIGS. 3A and 3B, which are a pair of graphs showing incorporation of $^3$H-thymidine into C-PAE cells treated with varying amounts of Arresten (FIG. 3A) or endostatin (FIG. 3B). Arresten appeared to inhibit thymidine incorporation in C-PAE as well as did endostatin. Behavior of control cells treated with Arresten and endostatin is also shown in FIGS. 4A, 4B, 4C, and 4D, with Arresten having little effect on 786-O cells (FIG. 4A), PC-3 cells (FIG. 4B), or HPEC cells (FIG. 4C). Endostatin had little effect on A-498 cells (FIG. 4D). All groups in FIGS. 3 and 4 represent triplicate samples.

Example 5

Arresten Inhibits Endothelial Cell Migration

Figure 5A:
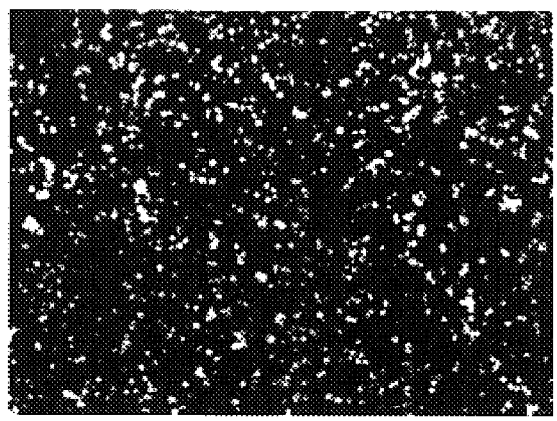
FIGS. 5A, 5B and 5C are a set of four photomicrographs showing the effects of Arresten (2 μg/ml, FIG. 5B) and endostatin (20 μg/ml, FIG. 5C) on endothelial cell migration via FBS-induced chemotaxis in human umbilical endothelial (ECV-304) cells.
Figure 5B:
Figure 5C:
Figure 6:
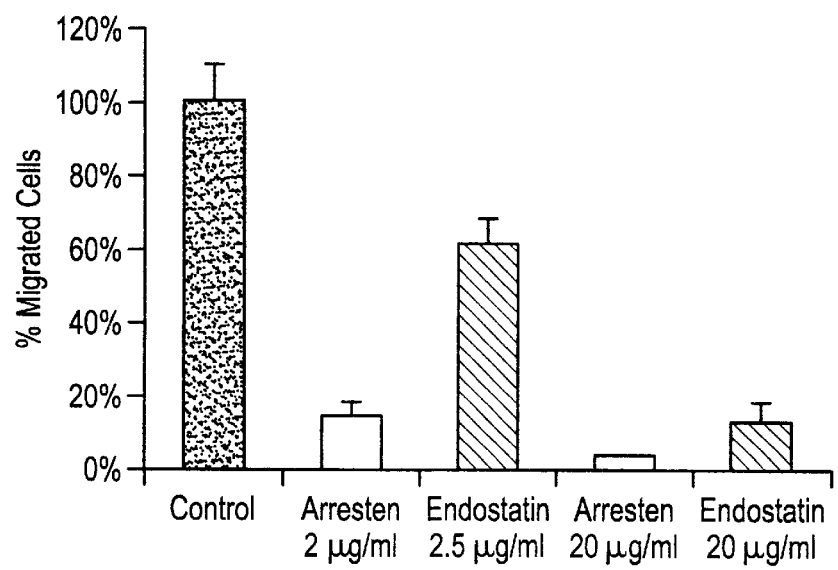
FIG. 6 is a bar chart showing in graphic form the results of FIG. 5.

The inhibitory effect of Arresten and endostatin on FBS-induced chemotaxis was tested on human umbilical endothelial cells (ECV-304 cells, ATCC 1998-CRL, ATCC (American Type Culture Collection, 10801 University Boulevard, Manassas, Va., 20110-2209, USA)) using a Boyden chamber assay (Neuro-Probe, Inc., Cabin John, Md., USA). ECV-304 cells were grown in M199 medium containing 10% FBS and 5 ng/mlDilC18(3) living fluorescent stain (Molecular Probes, Inc., Eugene, Oreg., USA) overnight. After trypsinization, washing and diluting cells in M199 containing 0.5% FBS, 60,000 cells were seeded on the upper chamber wells, together with or without Arresten or endostatin (2–40 μg/ml). M199 medium containing 2% FBS was placed in the lower chamber as a chemotactant. The cell-containing compartments were separated from the chemotactant with polycarbonate filters (Poretics Corp., Livermore, Calif., USA) of 8 μm pore size. The chamber was incubated at 37° C. with 5% $CO_2$ and 95% humidity for 4.5 hours. After discarding the non-migrated cells and washing the upper wells with PBS, the filters were scraped with a plastic blade, fixed in 4% formaldehyde in PBS, and placed on a glass slide. Using a fluorescent high power field, several independent homogenous images were recorded by a digital SenSys™ camera operated with image processing software PMIS (Roper Scientific/Photometrics, Tucson, Ariz., USA). Representative pictures are shown in FIGS. 5A, 5B and 5C, which show Arresten at 2 μg/ml as effective as endostatin at 20 μg/ml. Cells were counted using the OPTIMAS 6.0 software (Media Cybernetics, Rochester, N.Y.), and the results are shown in FIG. 6, which shows in graphic form the results seen in the photomicrographs.

Example 6

Arresten Inhibits Endothelial Tube Formation

Figure 7:
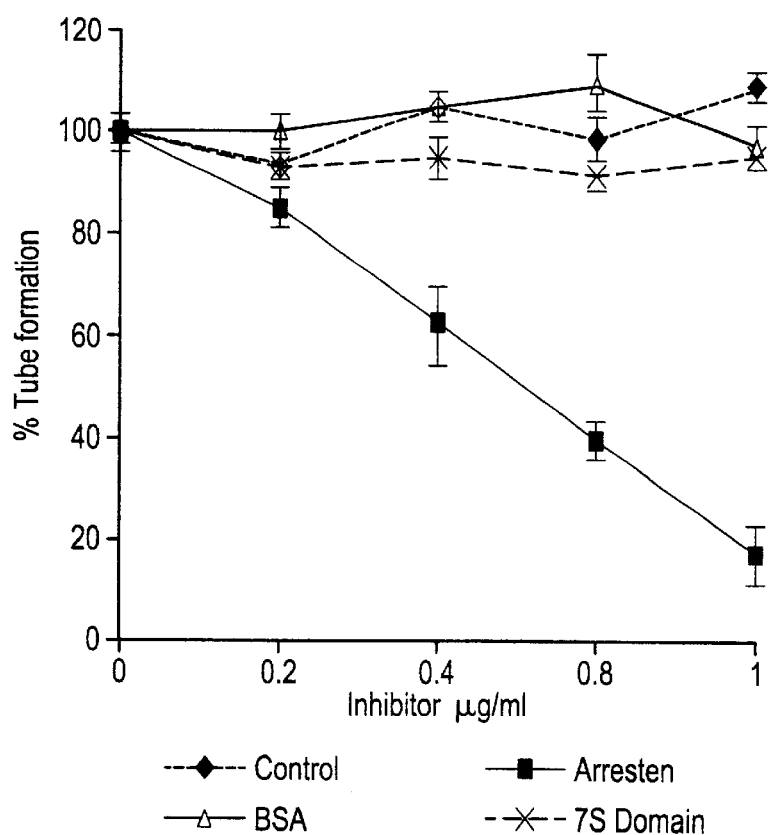
FIG. 7 is a line graph showing the effect of Arresten on the endothelial tube formation. Percent tube formation is shown on the y-axis, and concentration of inhibitor on the x-axis. The treatments were: none (control, ♦), BSA (control, Δ), 7S domain (control, X) and Arresten (■).
Figure 8A:
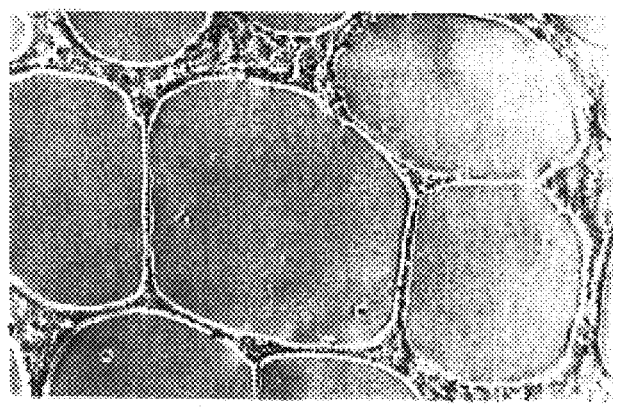
FIGS. 8A and 8B are a pair of photomicrographs showing the effect of Arresten (0.8 μg/ml, FIG. 8B) on endothelial tube formation relative to control (FIG. 8A).
Figure 8B:
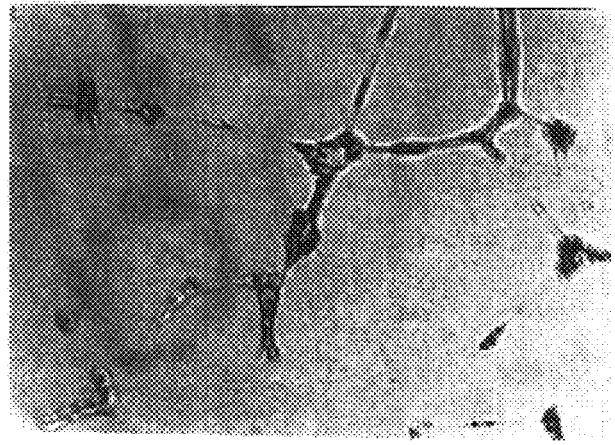

To measure inhibition of endothelial tube formation, 320 μl of matrigel (Collaborative Biomedical Products, Bedford, Mass., USA) was added to each well of a 24-well plate and allowed to polymerize (Grant, D. S. et al., 1994, Pathol. Res. Pract. 190:854–63). A suspension of 25,000 mouse aortic endothelial cells (MAE) in EGM-2 medium (Clonetics Corporation, San Diego, Calif., USA) without antibiotic was passed into each well coated with matrigel. The cells were treated with increasing concentrations of either Arresten, BSA, sterile PBS or the 7S domain. All assays were performed in triplicate. Cells were incubated for 24–48 hours at 37° C. and viewed using a CK2 Olympus microscope (3.3 ocular, 10× objective). The cells were then photographed using 400 DK coated TMAX film (Kodak). Cells were stained with diff-quik fixative (Sigma Chemical Company, St. Louis, Mo., USA) and photographed again. Ten fields were viewed, and the tubes counted and averaged. The results are shown in FIG. 7, which shows that Arresten (■) inhibits tube formation relative to controls (sterile PBS, ♦; BSA, Δ; 7S domain, x). Representative well-formed tubes can be observed in FIG. 8A, which shows the cells treated with the 7S domain (100× magnification). FIG. 8B, on the other hand, shows poor or no tube formation in MAE cells treated with 0.8 μg/ml Arresten (100× magnification).

The matrigel assay was also conducted in vivo in C57/BL6 mice. Matrigel was thawed overnight at 4° C. It was then mixed with 20 U/ml of heparin (Pierce Chemical Co., Rockford, Ill., USA), 150 ng/ml of bFGF (R&D Systems, Minneapolis, Minn., USA), and either 1 μg/ml of Arresten or 10 μg/ml of endostatin. The matrigel mixture was injected subcutaneously using a 21 g needle. Control groups received the same mixture, but with no angiogenic inhibitor. After 14 days, mice were sacrificed and the matrigel plugs removed. The matrigel plugs were fixed in 4% paraformaldehyde in PBS for 4 hours at room temperature, then switched to PBS for 24 hours. The plugs were embedded in paraffin, sectioned, and H&E stained. Sections were examined by light microscopy and the number of blood vessels from 10 high-power fields were counted and averaged.

When Matrigel was placed in the presence of bFGF, with or without increasing concentrations of Arresten, a 50% reduction in the number of blood vessels was observed at 1 μg/ml Arresten and 10 μg/ml of endostatin. These results show that Arresten affects the formation of new blood vessels by inhibiting various steps in the angiogenic process. The results also show that Arresten at 1 μg/ml is as effective as 10 μg/ml endostatin in inhibiting new vessel formation in vivo.

Example 7

Arresten Inhibits Tumor Metastases in vivo

C57/BL6 mice were intravenously injected with 1 million MC38/MUC1 (Gong, J. et al., 1997, Nat. Med. 3:558–61). Every other day for 26 days, five control mice were injected with 10 mM of sterile PBS, while six experimental mice received 4 mg/ml Arresten. After 26 days of treatment, pulmonary tumor nodules were counted for each mouse, and averaged for the two groups. Two deaths were recorded in each group. Arresten significantly reduced the average number of primary nodules from 300 in control mice, to 200.

Example 8

Arresten Inhibits Tumor Growth in vivo

Figure 9A:
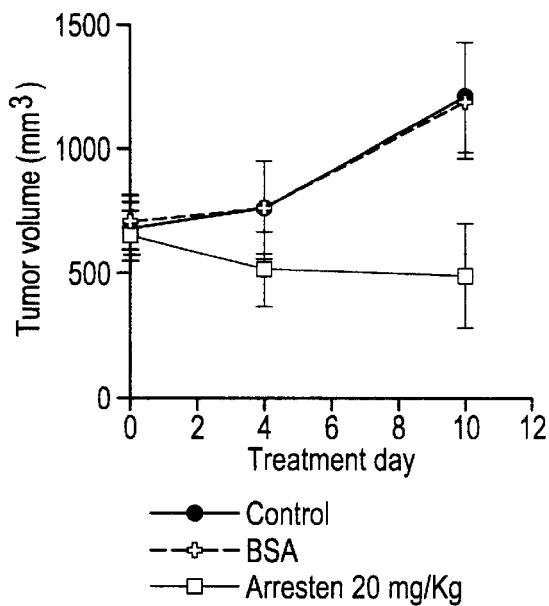
FIGS. 9A, 9B, 9C and 9D are a set of four line graphs showing the effect of Arresten and endostatin on tumor growth in vivo.
Figure 9B:
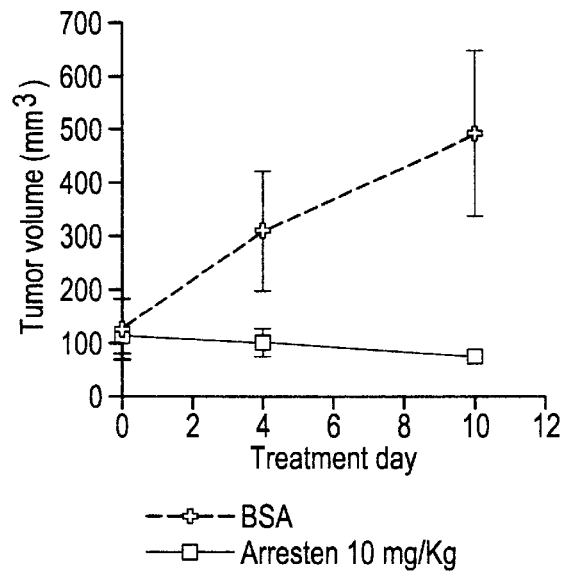

Two million 786-O cells were injected subcutaneously into 7- to 9-week-old male athymic nude mice. In the first group of six mice, the tumors were allowed to grow to about 700 mm$^3$. In a second group of six mice, the tumors were allowed to group to 100 mm$^3$. Arresten in sterile PBS was injected I.P. daily for 10 days, at a concentration of 20 mg/kg for the mice with tumors of 700 mm$^3$, and 10 mg/kg for the mice with tumors of 100 mm$^3$. Control mice received either BSA or the PBS vehicle. The results are shown in FIGS. 9A and 9B. FIG. 9A is a plot showing the increase in tumor volume from 700 mm$^3$ for 10 mg/kg Arresten-treated (□), BSA-treated (+), and control mice (●). Tumors in the Arresten-treated mice shrank from 700 to 500 mm$^3$, while tumors in BSA-treated and control mice grew to about 1200 mm$^3$ in 10 days. FIG. 9B shows that in mice with tumors of 100 mm$^3$, Arresten (□) also resulted in tumor shrinkage, to about 80 mm$^3$, while BSA-treated tumors (+) increaed in size to nearly 500 mm$^3$ in 10 days.

Figure 9C:
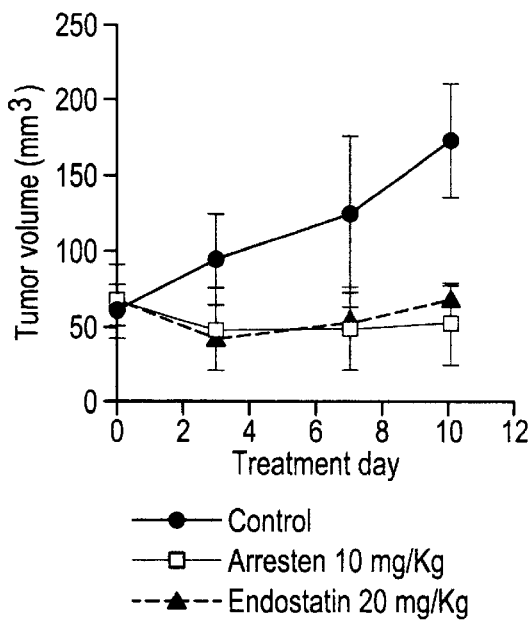
Figure 9D:
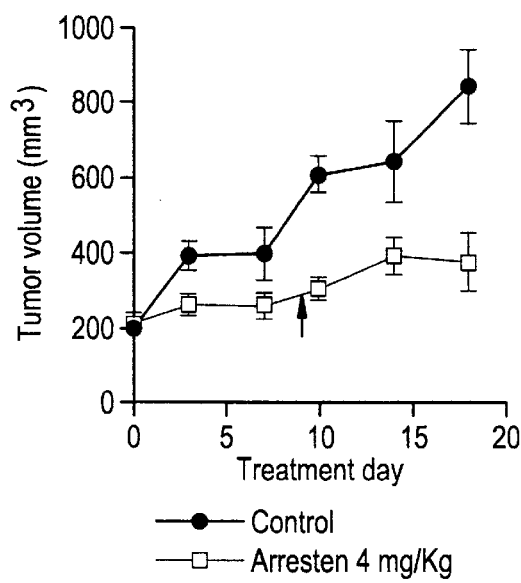

About 5 million PC-3 cells (human prostate adenocarcinoma cells) were harvested and injected subcutaneously into 7- to 9-week-old male athymic nude mice. The tumors grew for 10 days, and were then measured with Vernier calipers. The tumor volume was calculated using the standard formula (width$^2$×length×0.52 (O'Reilly, M. S. et al., 1997, Cell 88:277–85; O'Reilly, M. S. et al., 1994, Cell 79:315–28). Animals were divided into groups of 5–6 mice. Experimental groups were injected I.P. daily with Arresten (10 mg/kg/day) or endostatin (10 mg/kg/day). The control group received PBS each day. The results are shown in FIG. 9C, which shows that Arresten (□) inhibited the growth of tumors as well, or slightly better, than did endostatin (▲) or controls (●). The experiment was repeated, but with an Arresten dosage of 4 mg/kg/day. The results are in FIG. 9D (Arresten, □; control, ●). The treatment was stopped after eight days (arrow), but significant inhibition continued for twelve more days without additional Arresten treatments. After twelve days of no treatment, the tumors began to escape the inhibitory affects of Arresten.

Example 9

Circulating Half-life of Arresten

Native Arresten isolated from human placenta was injected intravenously into rate 200 g in size. Each rat received 5 mg of human Arresten. Serum was analyzed by direct ELISA at different time points for the presence of circulating Arresten by use of anti-Arresten antibodies. As a control, serum albumin was also evaluated at each time point to ensure that identical amounts of serum were used for the analysis. Arresten was found to circulate in the serum with a half-life of about 36 hours.

Another group of rats were injected with 200 μg of human Arresten I.P. and/or subcutaneously, and evaluated for signs of disease pathogenesis in the lung, kidney, liver, pancreas, spleen, brain, testis, ovary, etc. Direct ELISA was performed and Arresten antibodies were detected in the serum of these rats and some endogenous IgG deposition was noticed on the kidney glomerular basement membrane, as was observed previously (Kalluri, R. et al., 1994, Proc. Natl. Acad. Sci. USA 91:6201–5). The antibody deposition in the kidney was not accompanied by any signs of inflammation or deterioration of renal function. These experiments suggest that Arresten is non-pathogenic.

Example 10

Binding and Inhibition of MMP-2 Enzyme by Arresten

MMP-2, MMP-9, and antibodies to these enzymes were purchased from Oncogene, Inc. Direct ELISA was performed using native Arresten isolated from human placenta as described previously (Kalluri, R. et al., 1994, Proc. Natl. Acad. Sci. USA 91:6201–5). Both MMP-2 and MMP-9 specifically bound Arresten. They did not bind the 7S domain. This binding is independent of TIMP-2 and TIMP-1 binding, respectively.

To assess Arresten's ability to degrade basement membranes Matrigel was incubated with MMP-2 and MMP-9 for six hours at 37° C. with gentle shaking. The supernatant was analyzed by SDS-PAGE, and immunoblot with antibody to the α2 chain of Type IV collagen. At the beginning of the degradation assay, Arresten was added at increasing concentrations, and inhibition of MMP-2 activity was observed. The NC1 domains resolved in SDS-PAGE gels as monomers of 26 kDa and dimers of 56 kDa, and could be visualized by Western blot using Type IV collagen antibodies. Increasing concentrations of Arresten inhibited the degradation of basement membrane by MMP-2, showing that Arresten can bind MMP-2 and prevent it from degrading basement membrane collagen. Similar results were obtained for MMP-9.

Example 11

Recombinant Production of Canstatin in *E. coli*

Figure 11:
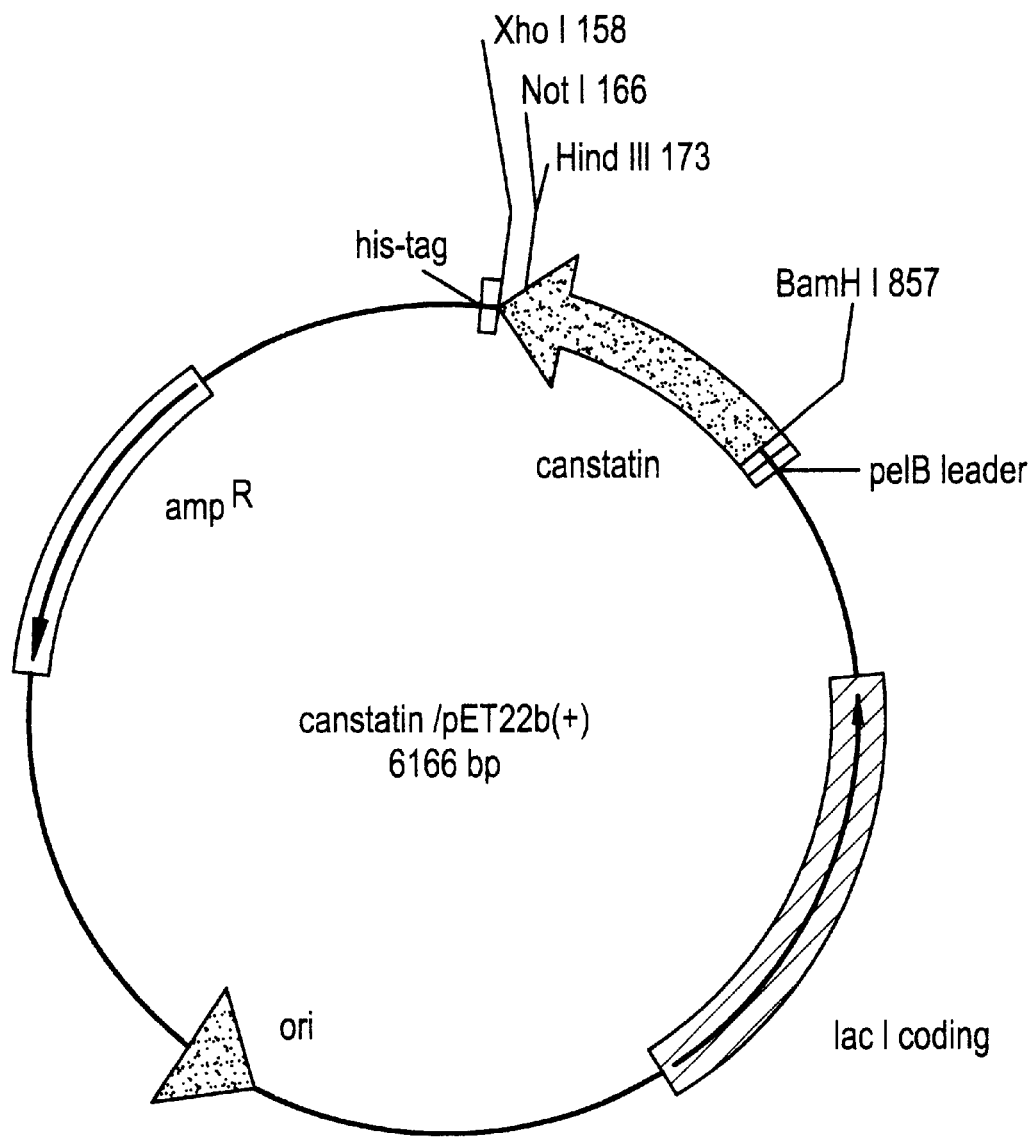
FIG. 11 is a schematic diagram representing the Canstatin cloning vector pET22b(+). Forward (SEQ ID NO:7) and reverse (SEQ ID NO:8) primers and site into which Canstatin was cloned are indicated.

The nucleotide (SEQ ID NO:5) and amino acid (SEQ ID NO:6) ("Canstain") sequence for the α2 NC1 domain of Type IV collagen is shown in FIG. 10. The sequence encoding Canstatin was amplified by PCR from the α2 NC1 (IV)/pDS vector (Neilson, E. G. et al., 1993, J. Biol. Chem. 268:8402–5) using forward primer 5'-CGG GAT CCT GTC AGC ATC GGC TAC CTC-3' (SEQ ID NO:7) and reverse primer 5'-CCC AAG CTT CAG GTT CTT CAT GCA CAC-3' (SEQ ID NO:8). The resulting cDNA fragment was digested with BamHI and HindIII and ligated into predigested pET22b(+) (Novagen, Madison, Wis., USA). The construct is shown in FIG. 11. This ligation placed Canstatin downstream of, and in-frame with, the pelB leader sequence, allowing for periplasmic localization and expression of soluble protein. Additional vector sequence was added to the protein encoding amino acids MDIGINSD (SEQ ID NO:13). The 3' end of the sequence was ligated in-frame with the poly-histidine-tag sequence. Additional vector sequence between the 3' end of the cDNA and the his-tag encoded the amino acids KLAAALE (SEQ ID NO:14). Positive clones were sequenced on both strands.

Plasmid constructs encoding Canstatin were first transformed into *E. coli* HMS174 (Novagen, Madison, Wis., USA) and then transformed into BL21 for expression (Novagen, Madison, Wis., USA). An overnight bacterial culture was used to inoculate a 500 ml culture in LB medium. This culture was grown for approximately 4 hours until the cells reached an $OD_{600}$ of 0.6. Protein expression was then induced by addition of IPTG to a final concentration of 0.5 mM. After a 2-hour induction, cells were harvested by centrifugation at 5,000×g and lysed by resuspension in 6 M guanidine, 0.1 M $NaH_2PO_4$, 0.01 M Tris-HCl, pH 8.0. Resuspended cells were sonicated briefly, and centrifuged at 12,000×g for 30 minutes. The supernatant fraction was passed over a 5 ml Ni-NTA agarose column (Qiagen, Hilden, Germany) 4–6 times at a speed of 2 ml/min. Non-specifically bound protein was removed by washing with 15 ml each of 10 mM, 25 mM and 50 mM imidazole in 8 M urea, 0.1 M $NaH_2PO_4$, 0.01 M Tris-HCl, pH 8.0. Canstatin protein was eluted from the column with two concentrations of imidazole (125 mM and 250 mM) in 8 M urea, 0.1 M $NaH_2PO_4$, 0.01 M Tris-HCl, pH 8.0. The eluted protein was dialyzed twice against PBS at 4° C. A portion of the total protein precipitated during dialysis. Dialyzed protein was collected and centrifuged at approximately 3,500×g and separated into pellet and supernatant fractions. Protein concentration in each fraction was determined by the BCA assay (Pierce Chemical Co., Rockford, Ill., USA) and quantitative SDS-PAGE analysis. The SDS-PAGE analysis revealed a monomeric band at 29 kDa, with the additional 3 kDa arising from polylinker and histidine tag sequences. The elutions containing Canstatin were combined and dialyzed against PBS for use in subsequent assays. Canstatin protein analyzed by SDS-PAGE and Western blotting was detected by poly-histidine tag antibodies. Collagen Type IV NC1 antibodies also detected bacterially-expressed recombinant constatin protein.

The *E. coli* expressed protein was isolated predominantly as a soluble protein. The fraction of total protein in the pellet was approximately 40%, with the remaining 60% recovered as a soluble protein. The total yield of protein was approximately 15 mg/liter.

Example 12

Expression of Canstatin in 293 Embryonic Kidney Cells

The pDS plasmid containing α2(IV)NC1 (Neilson, E. G. et al., 1993, J. Biol. Chem. 268:8402–5) was used to PCR amplify Canstatin in such a way that a leader signal sequence would be added in-frame into the pcDNA 3.1 eukaryotic expression vector (InVitrogen, San Diego, Calif., USA). The leader sequence from the 5' end of full length α2(IV) chain was cloned 5' to the NC1 domain to enable protein secretion into the culture medium. The Canstatin-containing recombinant vectors were sequenced using flanking primers. Error free cDNA clones were further purified and used for in vitro translation studies to confirm protein expression. The Canstatin-containing plasmid and control plasmid were used to transfect 293 cells using the calcium chloride method (Kingston, R. E., 1996, "Calcium Phosphate Transfection," pp. 9.1.4–9.1.7, in: *Curent Protocols in Molecular Biology*, Ausubel, F. M., et al., eds., Wiley and Sons, Inc. New York, N.Y., USA). Transfected clones were selected by geneticin (Life Technologies/Gibco BRL, Gaithersberg, Md., USA) antibiotic treatment. The cells were passed for three weeks in the presence of the antibiotic until no cell death was evident. Clones were expanded into T-225 flasks and grown until confluent. Then, the supernatant was collected and concentrated using an amicon concentrator (Amicon, Inc.). The concentrated supernatant was analyzed by SDS-PAGE, immunoblotting and ELISA for Canstatin expression. Strong binding in the supernatant was detected by ELISA. Canstatin-containing supernatant was subjected to affinity chromatography using Canstatin specific antibodies (Gunwar, S. et al., 1991, J. Biol. Chem. 266:15318–24). A major peak was identified, containing a pure monomer of about 24 kDa that was immunoreactive with Canstatin antibodies (anti-α2 NC1 antibody, 1:200 dilution).

Example 13

Canstatin Inhibits Endothelial Cell Proliferation

Bovine calf aortic endothelial (CPAE) cells were grown to confluence in DMEM with 10% fetal calf serum (FCS) and kept contact inhibited for 48 hours. Cells were harvested by trypsinization (Life Technologies/Gibco BRL, Gaithersberg, Md., USA) at 37° C. for 5 minutes. A suspension of 12,500 cells in DMEM with 0.5% FCS was added to each well of a 24-well plate coated with 10 μg/ml fibronectin. The cells were incubated for 24 hours at 37° C. with 5% $CO_2$ and 95% humidity. Medium was removed, and replaced with DMEM containing 0.5% FCS (unstimulated) or 10% FCS (stimulated and treated cells). 786-O, PC-3 and HEK 293 cells served as controls and were also grown to confluency, trypsinized and plated in the same manner. Cells were treated with concentrations of Canstatin or endostatin ranging from 0.025 to 40 mg/ml in triplicate. In thymidine incorporation experiments, all wells received 1 mCurie of $^3$H-thymidine at the time of treatment. After 24 hours, medium was removed and the wells were washed 3 times with PBS. Radioactivity was extracted with 1N NaOH and added to a scintillation vial containing 4 ml of ScintiVerse II (Fisher Scientific, Pittsburgh, Pa., USA) solution. Thymidine incorporation was measured using a scintillation counter.

Figure 12A:
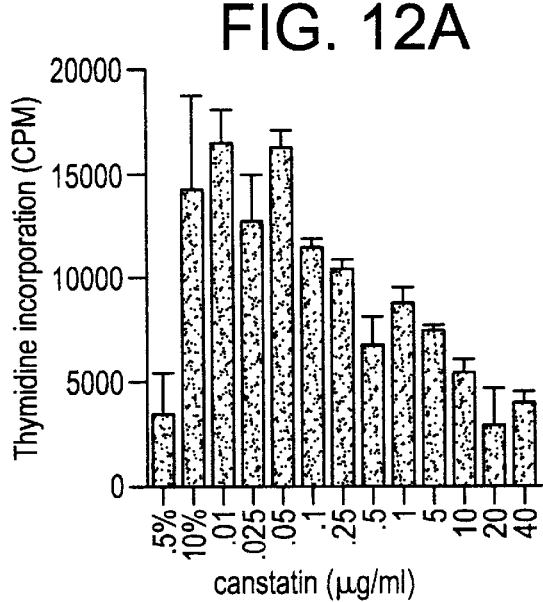
FIGS. 12A, 12B, 12C and 12D are histograms showing the effect of varying concentrations of Canstatin (x-axis) on proliferation of endothelial (C-PAE) cells (FIGS. 12A and 12C) and non-endothelial (786-O, PC-3 and HEK 293) cells (FIGS. 12B and 12D). Proliferation was measured as a function of $^3$H-thymidine incorporation (FIGS. 12A and 12B) and methylene blue staining (FIGS. 12C and 12D).
Figure 12B:
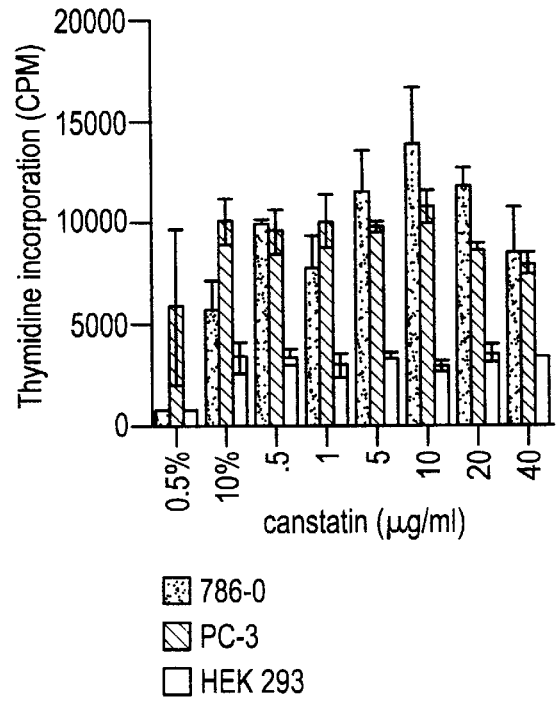

The results are shown in FIGS. 12A and 12B. FIG. 12A is a histogram showing the effect of varying amounts of Canstatin on the proliferation of CPAE cells. Thymidine incorporation in counts per minute is on the y-axis. "0.5%" on the x-axis is the 0.5% FCS (unstimulated) control, and "10%" is the 10% FCS (stimulated) control. Treatment with increasing concentrations of Canstatin steadily reduced thymidine incorporation. FIG. 12B is a histogram showing the effect of increasing amounts of Canstatin on thymidine incorporation in the nonendothelial cells 786-O (black bars), PC-3 (cross-hatched bars) and HEK 293 (white bars). Thymidine incorporation in counts per minute is show in the y-axis, and the x-axis shows, for each of the three cell lines, the 0.5% FCS (unstimulated) and the 10% FCS (stimulated) control, followed by increasing concentrations of Canstatin. All groups represent triplicate samples, and the bars represent mean counts per minute±the standard error of the mean.

A methylene blue staining test was also done. 3,100 cells were added to each well and treated as above, and cells were then counted using the method of Oliver et al. (Oliver, M. H. et al., 1989, J. Cell. Science 92:513–8). All wells were washed one time with 100 ml of 1×PBS and the cells were fixed by adding 100 ml of 10% formalin in neutral-buffered saline (Sigma Chemical Co., St. Louis, Mo., USA) for 30 minutes at room temperature. After formalin removal cells were stained with a solution of 1% methylene blue (Sigma Chemical Co., St. Louis, Mo., USA) in 0.01 M borate buffer (pH 8.5) for 30 minutes at room temperature. After removal of staining solution, the wells were washed 5 times with 100 ml of 0.01 M borate buffer (pH 8.5). Methylene blue was extracted from the cells with 100 ml of 0.1N HCl/ethanol (1:1 mixture) for 1 hour at room temperature. The amount of methylene blue staining was measured on a microplate reader (BioRad, Hercules, Calif., USA) using light absorbance at 655 nm wavelength.

Figure 12C:
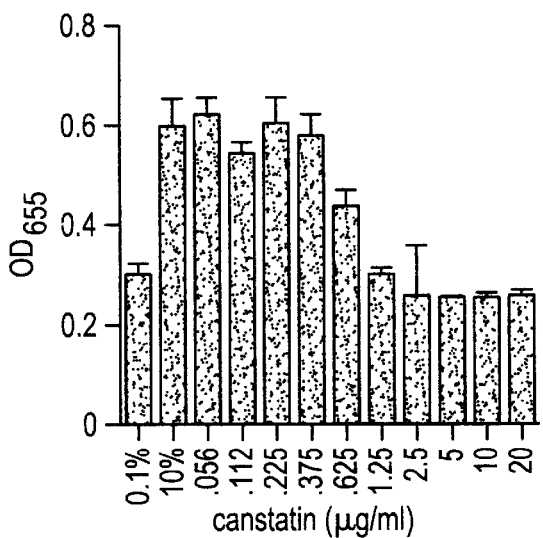
Figure 12D:
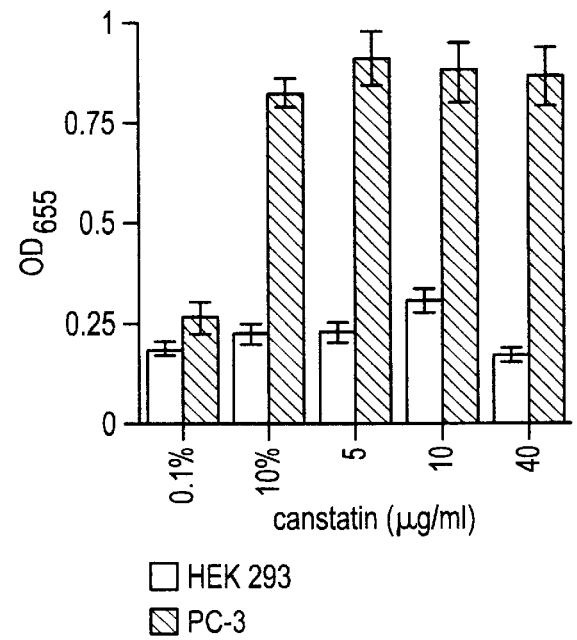

The results are shown in FIGS. 12C and 12D. FIG. 12C is a histogram showing the effect of increasing amounts of Canstatin on the uptake of dye by CPAE cells. Absorbance at $OD_{655}$ is shown on the y-axis. "0.1%" represents the 0.1% FCS-treated (unstimulated) control, and "10%" is the 10% FCS-treated (stimulated) control. The remaining bars represent treatments with increasing concentrations of Canstatin. In CPAE cells, dye uptake dropped off to the level seen in unstimulated cells at a Canstatin treatment level of about 0.625–1.25 μg/ml. FIG. 12D is a histogram showing the effect of varying concentrations of Canstatin on non-endothelial cells HEK 293 (white bars) and PC-3 (cross-hatched bars). Absorbance at $OD_{655}$ is on the y-axis. "0.1%" represents the 0.1% FCS-treated (unstimulated) control, and "10%" is the 10% FCS-treated (stimulated) control. Bars represent mean of the relative absorbance units at 655 nm±the standard error for 8 wells per treatment concentration.

A dose-dependent inhibition of 10% serum-stimulated endothelial cells was detected with an $ED_{50}$ value of approximately 0.5 μg/ml (FIGS. 12A and 12C). No significant effect was observed on the proliferation of renal carcinoma cells (786-O), prostate cancer cells (PC-3) or human embryonic kidney cells (HEK293), at Canstatin doses up to 40 mg/ml (FIGS. 12B and 12D). This endothelial cell specificity indicates that Canstatin is likely a particularly effective anti-angiogenic agent.

Example 14

Canstatin Inhibits Endothelial Cell Migration

In the process of angiogenesis, endothelial cells not only proliferate but also migrate. Therefore, the effect of Canstatin on endothelial cell migration was assessed. The inhibitory effect of Canstatin and endostatin on FBS-induced chemotaxis was tested on human umbilical endothelial cells (HUVECs) using the Boyden chamber assay (Neuro-Probe, Inc., Cabin John, Md., USA). HUVECs cells were grown in M199 (Life Technologies/Gibco BRL, Gaithersberg, Md., USA) containing 10% FBS and 5 ng/ml DiIC18(3) living fluorescent stain (Molecular Probes, Inc., Eugene, Oreg., USA) overnight. After trypsinizing, washing and diluting cells in M199 containing 0.5% FBS, 60,000 cells were seeded in the upper chamber wells, together with or without Canstatin (0.01 or 1.00 mg/ml). M199 medium containing 2% FBS was placed in the lower chamber as a chemotactant. The cell-containing compartments were separated from the chemotactant with polycarbonate filters (Poretics Corp., Livermore, Calif., USA) of 8 μm pore size. The chamber was incubated at 37° C. with 5% $CO_2$ and 95% humidity for 4.5 hours. After discarding the non-migrated cells and washing the upper wells with PBS, the filters were scraped with a plastic blade, fixed in 4% formaldehyde in PBS and placed on a glass slide. Using a fluorescent high power field, several independent homogenous images were recorded by a digital SenSys™ camera operated with Image Processing Software PMIS (Roper Scientific/Photometrics, Tucson, Ariz., USA). Cells were counted by employing the OPTI-MIZE 6.0 software-program (Media Cybernetics, Rochester, N.Y.) (Klemke, R. L. et al., 1994, J. Cell. Biol. 127:859–66).

Figure 13:
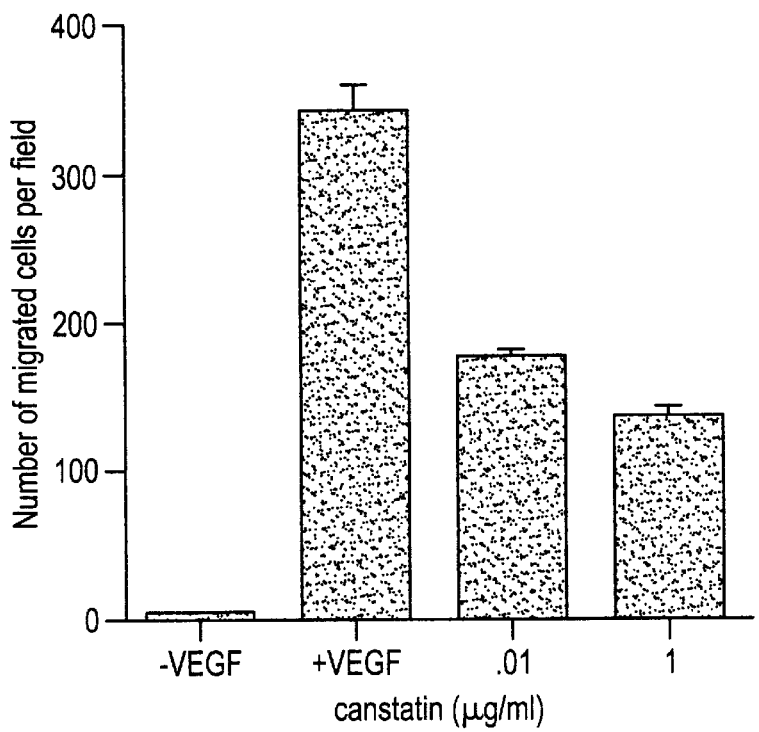
FIG. 13 is a bar chart showing the number of migrated endothelial cells per field (y-axis) for treatments of no VEGF (no VEGF or serum), and VEGF (1% FCS and 10 ng/ml VEGF) cells, and for treatments of 0.01 Canstatin (1% FCS and 10 ng/ml VEGF and 0.01 μg/ml Canstatin) and 1.0 μg/ml Canstatin (1% FCS and 10 ng/ml VEGF and 1 μg/ml Canstatin).

The results are shown in FIG. 13, which is a bar chart showing the number of migrated endothelial cells per field (y-axis) for treatments of no VEGF (no VEGF or serum), and VEGF (1% FCS and 10 ng/ml VEGF) cells, and for treatments of 0.01 Canstatin (1% FCS and 10 ng/ml VEGF and 0.01 μg/ml Canstatin) and 1.0 μg/ml Canstatin (1% FCS and 10 ng/ml VEGF and 1 μg/ml Canstatin).

Canstatin inhibited the migration of HUVECs with a significant effect observed at 10 ng/ml. The ability of Canstatin to inhibit both proliferation and migration of endothelial cells suggests that it works at more than one step in the process of angiogenesis. Alternatively, Canstatin may act as an apoptotic signal for stimulated endothelial cells which would be able to affect both proliferation and migration. Apoptotic induction has been reported for angiostatin, another anti-angiogenic molecule (O'Reilly, M. S. et al., 1994, Cell 79:315–28; Lucas, R. et al., 1998, Blood 92:4730–41).

Example 15

Canstatin Inhibits Endothelial Tube Formation

As a first test of Canstatin's anti-angiogenic capacity, it was assessed for its ability to disrupt tube formation by endothelial cells in matrigel, a solid gel of mouse basement membrane proteins. When mouse aortic endothelial cells are cultured on matrigel, they rapidly align and form hollow tube-like structures.

Matrigel (Collaborative Biomedical Products, Bedford, Mass., USA) was added (320 ml) to each well of a 24 well plate and allowed to polymerize (Grant, D. S. et al., 1994, Pathol. Res. Pract. 190:854–63). A suspension of 25,000 mouse aortic endothelial cells (MAE) in EGM-2 (Clonetics Corporation, San Diego, Calif., USA) medium without antibiotic was passed into each well coated with matrigel. The cells were treated with either Canstatin, BSA, sterile PBS or α5-NC1 domain in increasing concentrations. All assays were performed in triplicate. Cells were incubated for 24–48 hours at 37° C. and viewed using a CK2 Olympus microscope (3.3 ocular, 10× objective). The cells were then photographed using 400 DK coated TMAX film (Kodak). Cells were stained with diff-quik fixative (Sigma Chemical Co., St. Louis, Mo., USA) and photographed again (Grant, D. S. et al., 1994, Pathol. Res. Pract. 190:854–63). Ten fields were viewed, tubes counted and averaged.

Figure 14:
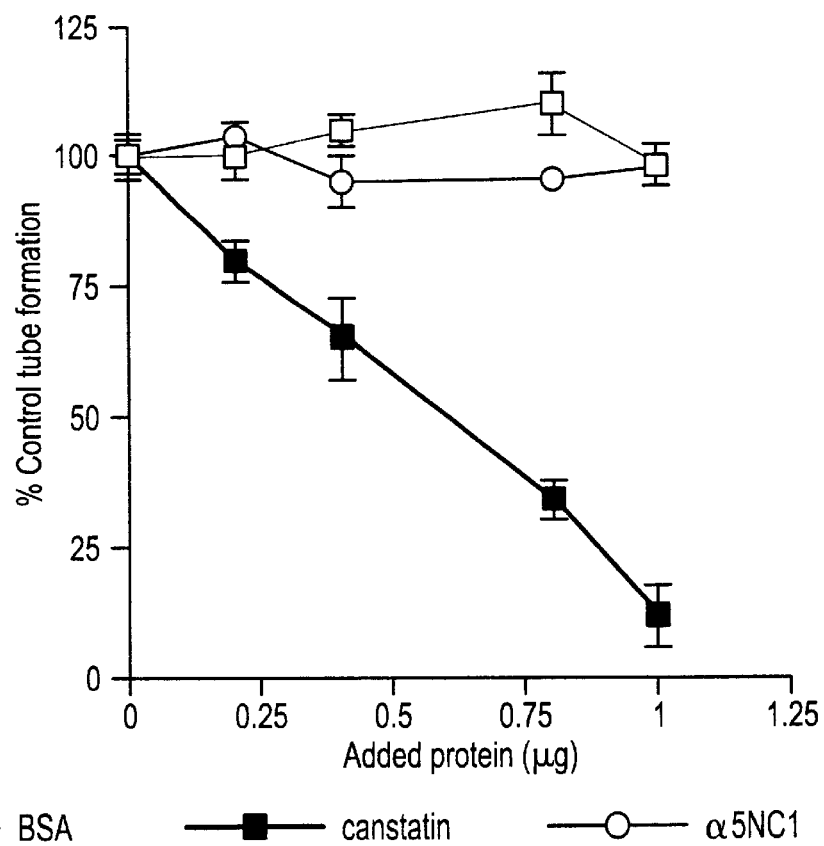
FIG. 14 is a line graph showing the amount of endothelial tube formation as a percent of control (PBS-treated wells) tube formation (y-axis) under varying treatments of BSA (□), Canstatin (■), and α5NC1 (○). Vertical bars represent the standard error of the mean.

The results are shown in FIG. 14, which is a graph showing the amount of tube formation as a percent of control (PBS-treated wells) tube formation (y-axis) under varying treatments of BSA (□), Canstatin (■), and α5NC1 (○). Vertical bars represent the standard error of the mean. The results show that Canstatin greatly reduces endothelial tube formation relative to controls.

Canstatin selectively inhibited endothelial tube formation in a dose dependent manner, with a near complete inhibition of tube formation seen with the addition of 1 mg of Canstatin protein (FIG. 14). Neither a control protein, bovine serum albumin (BSA), nor the NC1 domain of type IV collagen α5 chain, had an effect on endothelial tube formation, demonstrating that Canstatin's inhibitory effect in this assay is specific to Canstatin and not due to the added protein content. These results indicated that Canstatin is an anti-angiogenic agent.

Example 16

Canstatin Inhibits Tumor Growth in vivo

Figure 15A:
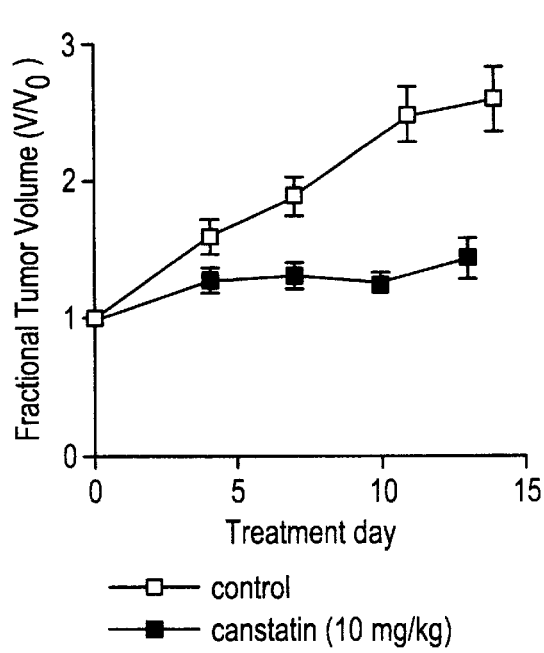
FIGS. 15A, 15B, 15C and 15D are line graphs depicting the effect on PC-3 cells (FIGS. 15A and 15B) and 786-O cells (FIGS. 15C and 15D) of Canstatin (■), endostatin (○) and controls (□) on fractional tumor volume (y-axis, FIGS. 15A and 15B) or tumor volume in mm$^3$ (y-axis, FIGS. 15C and 15D), plotted over the days of treatment (x-axis).

Human prostate adenocarcinoma cells (PC-3 cells) were harvested from culture and 2 million cells in sterile PBS were injected subcutaneously into 7- to 9-week-old male SCID mice. The tumors grew for approximately 4 weeks after which animals were divided into groups of 4 mice. Experimental groups were injected daily I.P. with Canstatin at a dosage of 10 mg/kg in a total volume of 0.1 ml of PBS. The control group received equal volumes of PBS each day. At the start of treatment (day 0), the tumors ranged in volume from 88 mm$^3$ to 135 mm$^3$ for the control mice, and 108 mm$^3$ to 149 mm$^3$ for the Canstatin-treated mice. Each group contained 5 mice. The calculated tumor volume on a given day was divided by the volume on treatment day 0 to produce a fractional tumor volume (V/V$_0$). The results are shown in FIG. 15A, which is a graph depicting the fractional tumor volume (y-axis)±the standard error, plotted over the treatment day (x-axis). Canstatin-treated (■) tumors increased only marginally in size relative to controls (□).

Figure 15B:
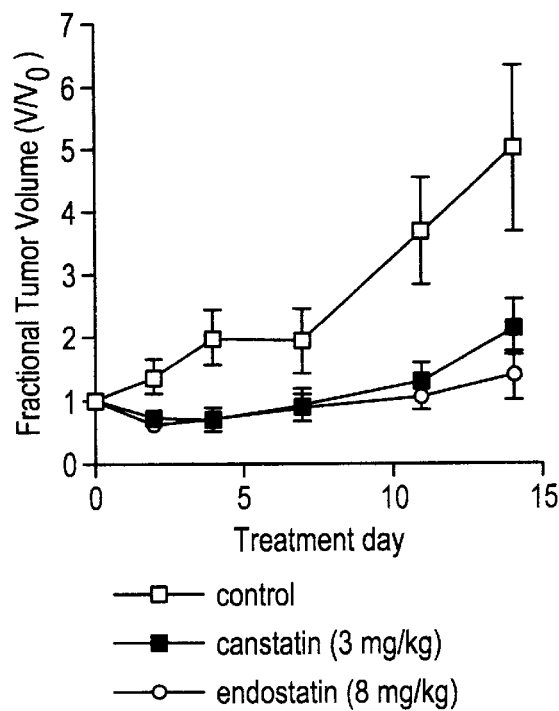

In a second PC-3 experiment, PC-3 cells were harvested from culture and 3 million cells were injected into 6- to 7-week-old old athymic nude mice, and tumors were allowed to grow subcutaneously for approximately 2 weeks after which the animals were divided into groups of 4 mice. Experimental groups (4 mice) were injected daily I.P. with Canstatin at a dosage of 3 mg/kg in a total volume of 0.2 ml of PBS or endostatin at a dosage of 8 mg/kg in the same volume of PBS. The control group (4 mice) received equal volumes of PBS each day. Tumor length and width were measured using a Vernier caliper and the tumor volume was calculated using the standard formula: length×width$^2$×0.52. Tumor volumes ranged from 26 mm$^3$ to 73 mm$^3$, and the calculated tumor volume on a given day was divided by the volume on treatment day 0 to produce a fractional tumor volume (V/V$_0$), as described above. The results are shown in FIG. 15B, which is a graph depicting the fractional tumor volume (y-axis)±the standard error, plotted over the treatment day (x-axis). Relative to controls (□), Canstatin-treated (■) tumors increased only marginally in size, and the results compared favorably with those achieved with endostatin (○).

Figure 15C:
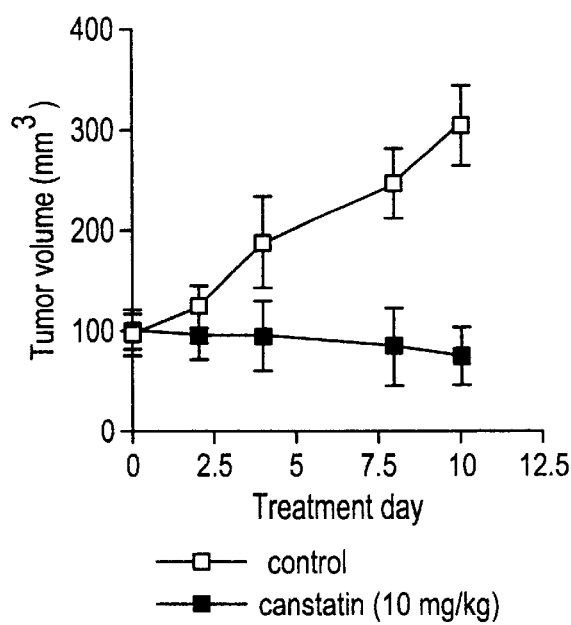

For the renal cell carcinoma cell model, 2 million 786-O cells were injected subcutaneously into 7- to 9-week-old male athymic nude mice. The tumors were allowed to grow to either about 100 mm$^3$ or about 700 mm$^3$. Each group contained 6 mice. Canstatin in sterile PBS was injected I.P. daily at a concentration of 10 mg/kg for 10 days. The control group received the same volume of PBS. The results are shown in FIGS. 15C (100 mm$^3$ tumors) and 15D (700 mm$^3$ tumors). In both groups, the Canstatin-treated (■) tumors actually shrank relative to the controls (□).

Figure 15D:
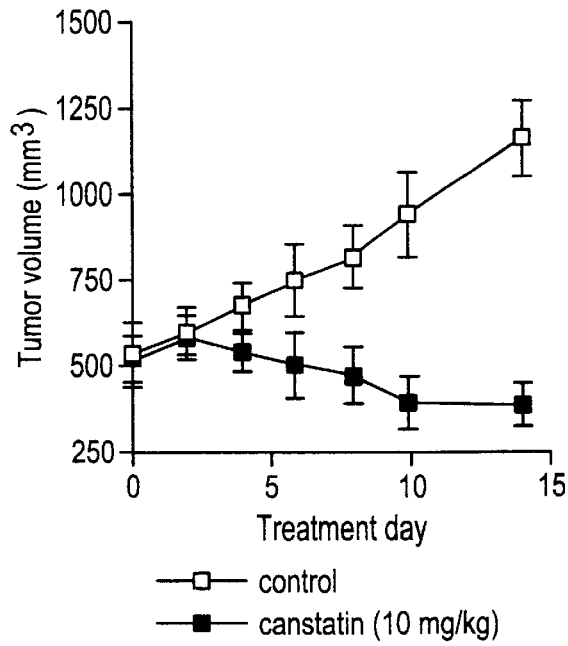

Canstatin produced in *E. coli* inhibited the growth of small (100 mm$^3$, FIG. 15C) and large (700 mm$^3$, FIG. 15D) renal cell carcinoma (786-O) tumors. For human prostate (PC-3) tumors in severe combined immunodeficient (SCID) mice, Canstatin at 10 mg/kg held the fractional tumor volume to 55% of the vehicle only-injected mice. In athymic (nu/nu) mice lower doses of both Canstatin and endostatin were used, and 3 mg/kg of Canstatin had the same suppressive effect as 8 mg/kg of endostatin. In all in vivo studies, mice appeared healthy with no signs of wasting and none of the mice died during treatment.

Example 17

CD31 Immunohistochemistry on Canstatin-treated Mice

The decreased size of the tumors in vivo suggested a suppressive effect on the formation of blood vessels in these tumors. To detect tumor blood vessels, anti-CD31 antibody alkaline phosphatase-conjugated immunocytochemistry was performed on paraffin-embedded tumor sections. The removed tumors were dissected with a scapel into several pieces approximately 3–4 mm thick then fixed in 4% paraformaldehyde for 24 hours. Tissues were then switched to PBS for 24 hours before dehydration and paraffin embedding. After embedding in paraffin, 3 mm tissue sections were cut and mounted. Sections were deparaffinized, rehydrated, and pretreated with 300 mg/ml protease XXIV (Sigma Chemical Co., St. Louis, Mo., USA) at 37° C. for 5 minutes. Digestion was stopped in 100% ethanol. Sections were air dried, rehydrated and blocked with 10% rabbit serum. Slides were then incubated at 4° C. overnight with a 1:50 dilution of rat anti-mouse CD31 monoclonal antibody (PharMingen, San Diego, Calif., USA), followed by two successive incubations at 37° C. for 30 minutes each with 1:50 dilutions of rabbit anti-rat immunoglobulin (DAKO) and rat APAAP (DAKO). The color reaction was performed with new fuchsin. Sections were counterstained with hematoxylin.

A decrease in blood vessel number was seen in Canstatin treated tumors compared to control tumors.

Example 18

Recombinant Production of Tumstatin and Tumstatin Mutants in *E. coli*

Figure 17:
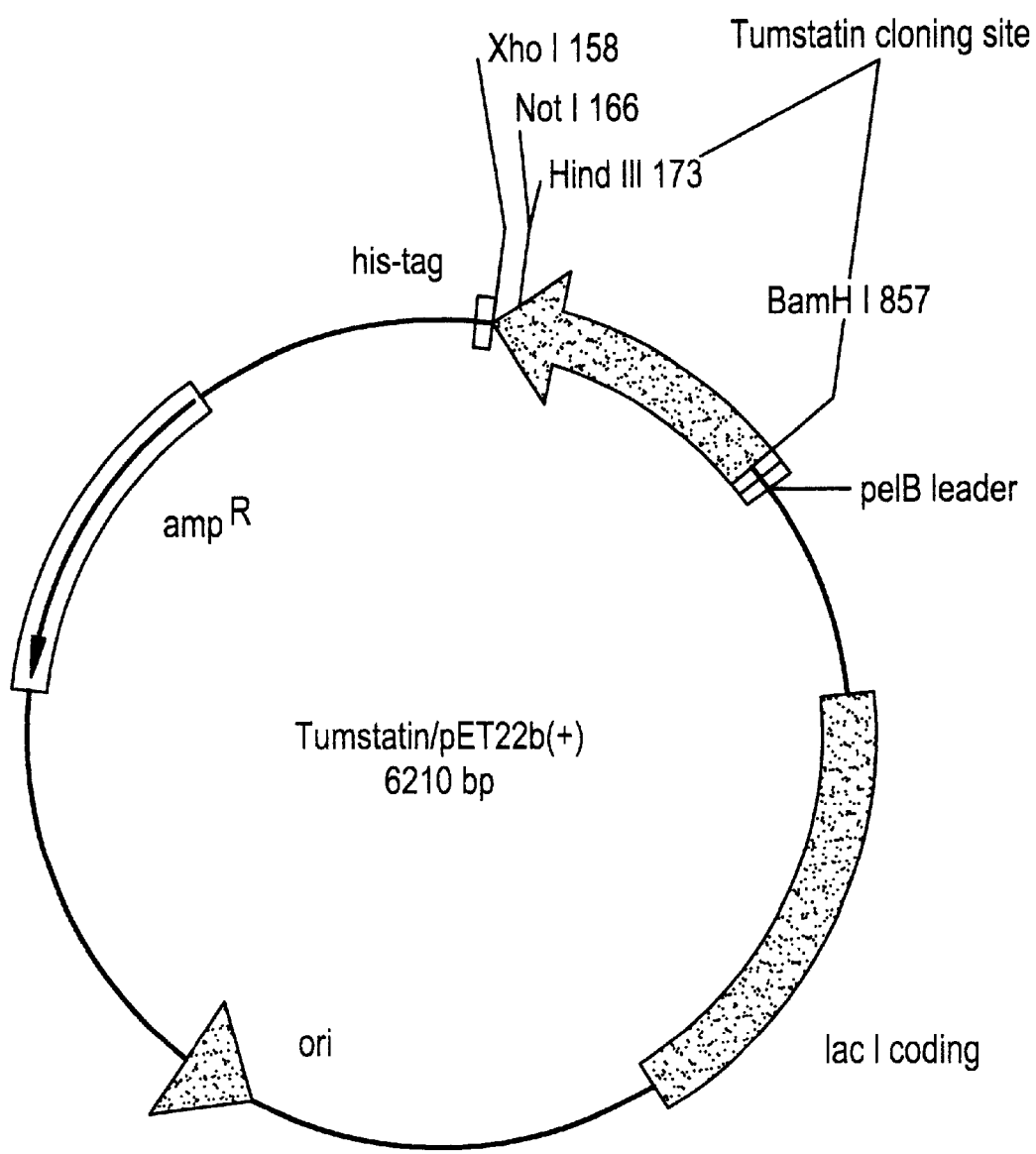
FIG. 17 is a schematic diagram representing the Tumstatin cloning vector pET22b(+). Forward (SEQ ID NO:11) and reverse (SEQ ID NO:12) primers and site into which Tumstatin was cloned are indicated.

The nucleotide (SEQ ID NO:9) and amino acid (SEQ ID NO:10) ("Tumstatin") sequences for the α3 chain of the NC1 domain of Type IV collagen are shown in FIG. 16. The sequence encoding Tumstatin was amplified by PCR from the α3 NC1 (IV)/pDS vector (Neilson, E. G. et al., 1993, J. Biol. Chem. 268:8402–5) using the forward primer 5'-CGG GAT CCA GGT TTG AAA GGA AAA CGT-3' (SEQ ID NO:11) and the reverse primer 5'-CCC AAG CTT TCA GTG TCT TTT CTT CAT-3' (SEQ ID NO:12). The resulting cDNA fragment was digested with BamHI and HindIII and ligated into predigested pET22b(+) (Novagen, Madison, Wis., USA). The construct is shown in FIG. 17. The ligation placed Tumstatin downstream of and in-frame with the pelB leader sequence, allowing for periplasmic localization and expression of soluble protein. Additional vector sequence was added to the protein encoding amino acids MDIGINSD (SEQ ID NO:13). The 3' end of the sequence was ligated in-frame with the polyhistidine tag sequence. Additional vector sequence between the 3' end of the cDNA and the his-tag encoded the amino acids KLAAALE (SEQ ID NO:14). Positive clones were sequenced on both strands. Plasmid constructs encoding Tumstatin were first transformed into *E. coli* HMS174 (Novagen, Madison, Wis., USA) and then transformed into BL21 for expression (Novagen, Madison, Wis., USA). Overnight bacterial culture was used to inoculate a 500 ml culture in LB medium (Fisher Scientific, Pittsburgh, Pa., USA). This culture was grown for approximately 4 hours until the cells reached an $OD_{600}$ of 0.6. Protein expression was then induced by addition of IPTG to a final concentration of 1 mM. After a 2-hour induction, cells were harvested by centrifugation at 5,000×g and lysed by resuspension in 6 M guanidine, 0.1 M $NaH_2PO_4$, 0.01 M Tris-HCl, pH 8.0. Resuspended cells were sonicated briefly, and centrifuged at 12,000×g for 30 minutes. The supernatant fraction was passed over a 5 ml Ni-NTA agarose column (Qiagen, Hilden, Germany) 4–6 times at a speed of 2 ml per minute. Non-specifically bound protein was removed by washing with both 10 mM and 25 mM imidazole in 8 M urea, 0.1 M $NaH_2PO_4$, 0.01 M Tris-HCl, pH 8.0. Tumstatin protein was eluted from the column with increasing concentrations of imidazole (50 mM, 125 mM, and 250 mM) in 8 M urea, 0.1 M $NaH_2PO_4$, 0.01 M Tris-HCl, pH 8.0. The eluted protein was dialyzed twice against PBS at 4° C. A portion of the total protein precipitated during dialysis. Dialyzed protein was collected and centrifuged at approximately 3,500×g and separated into insoluble (pellet) and soluble (supernatant) fractions.

*E. coli*-expressed Tumstatin was isolated predominantly as a soluble protein and SDS-PAGE analysis revealed a monomeric band at 31 kDa. The additional 3 kDa arises from polylinker and histidine tag sequences. The eluted fractions containing this band were used in following experiments. Protein concentration in each fraction was determined by the BCA assay (Pierce Chemical Co., Rockford, Ill., USA) and quantitative SDS-PAGE analysis using scanning densitometry. Under reducing conditions, a band observed around 60 kDa representing a dimer of tumstatin in non-reduced condition resolved as a single band of 31 kDa. The total yield of protein was approximately 5 mg per liter.

Figure 18:
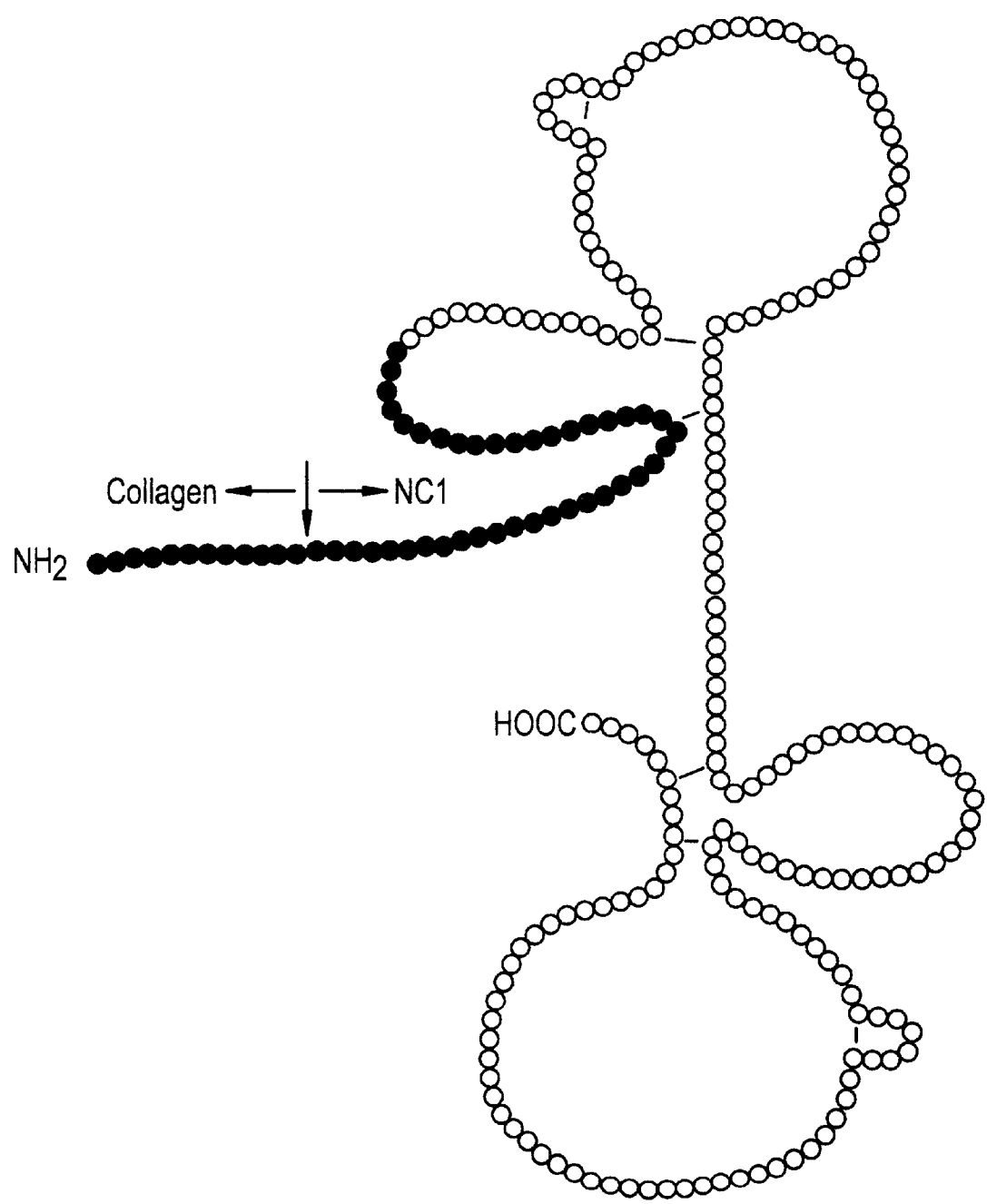
FIG. 18 is a schematic diagram showing the location of truncated amino acids within the α3(IV)NC1 monomer in the Tumstatin mutant Tumsatin N-53. The filled circles correspond to the N-terminal 53 amino acid residues deleted from Tumstatin to generate this mutant. The disulfide bonds, marked by short bars, are arranged as they occur in α1(IV) NC1 and α2(IV)NC1.

Recombinant truncated Tumstatin (Tumstatin-N53) lacking the 53 N-terminal amino acids was produced in *E. coli* and purified as previously described for another mutant (Kalluri, R. et al., 1996, J. Biol. Chem. 271:9062–8). This mutant is depicted in FIG. 18, which is a composite diagram showing the location of truncated amino acids within the α3(IV) NC1 monomer. The filled circles correspond to the N-terminal 53 amino acid residues deleted from Tumstatin to generate 'Tumstatin-N53' (Kalluri, R. et al., 1996, J. Biol. Chem. 271:9062–8). The disulfide bonds, marked by short bars, are arranged as they occur in α1(IV) NC2 and α2(IV) NC1 (Siebold, B. et al., 1988, Eur. J. Biochem. 176:617–24). For clarity, only one of two possible disulfide configurations is indicated.

Rabbit antibodies raised against human α3 (IV) NC1 were prepared as previously described (Kalluri, R. et al., 1997, J. Clin. Invest. 99:2470–8). Monoclonal rat anti-mouse CD31 (platelet endothelial cell adhesion molecule, PECAM-1) antibody was purchased from (PharMingen, San Diego, Calif., USA). FITC-conjugated goat anti-rat IgG antibody, FITC-conjugated goat anti-rabbit IgG antibody, and goat anti rabbit IgG antibody conjugated with horseradish peroxidase were purchased from Sigma Chemical Co. (St. Louis, Mo., USA).

The concentrated supernatant obtained above was analyzed by SDS-PAGE and immunoblotting for the Tumstatin expression as previously described (Kalluri, R. et al., 1996, J. Biol. Chem. 271:9062–8). SDS-PAGE in one dimension was carried out with 12% resolving gels and the discontinuous buffer system. The separated proteins were transferred to nitrocellulose membrane and blocked with 2% BSA for 30 minutes at room temperature. After blocking the remaining binding sites, the membrane was washed thoroughly with wash buffer and incubated with a primary antibody at a dilution of 1:1000 in PBS containing 1% BSA. Incubation was carried out at room temperature overnight on a shaker. The blot was then washed thoroughly with washing buffer and incubated with a secondary antibody conjugated to horseradish peroxidase for 3 hours at room temperature on a shaker. The blot was again washed thoroughly and substrate (diaminobenzidine in 0.05 M phosphate buffer containing 0.01% cobalt chloride and nickel ammonium) was added and incubated for 10 minutes at room temperature. The substrate solution was then poured out, and substrate buffer containing hydrogen peroxide was added. After development of bands, the reaction was stopped with distilled water and the blot was dried. A single band of 31 kDa was seen.

Example 19

Expression of Tumstatin in 293 Embryonic Kidney Cells

Human Tumstatin was also produced as a secreted soluble protein in 293 embryonic kidney cells using the pcDNA 3.1 eukaryotic vector. This recombinant protein (without any purification or detection tags) was isolated using affinity chromatography and a pure monomeric form was detected in the major peak by SDS-PAGE and immunoblot analyses.

The pDS plasmid containing α3(IV)NC1 (Neilson, E. G. et al., 1993, J. Biol. Chem. 268:8402–5) was used to PCR amplify Tumstatin in a way that it would add a leader signal sequence in-frame into the pcDNA 3.1 eukaryotic expression vector (InVitrogen, San Diego, Calif., USA). The leader sequence from the 5' end of full length α3(IV) chain was cloned 5' to the NC1 domain to enable protein secretion into the culture medium. The Tumstatin-containing recombinant vectors were sequenced on both strands using flanking primers. Error-free cDNA clones were further purified and used for in vitro translation studies to confirm protein expression. The Tumstatin-containing plasmid and control plasmid were used to transfect 293 cells using the calcium chloride method (Sambrook, J. et al., 1989, *Molecular Cloning: A Laboratory Manual*, Cold Spring Harbor Laboratory, Cold Spring Harbor, N.Y., USA, pps. 16.32–16.40). Transfected clones were selected by geneticin (Life Technologies/Gibco BRL, Gaithersburg, Md., USA) antibiotic treatment. The cells were passed for three weeks in the presence of the antibiotic until no cell death was evident. Clones were expanded into T-225 flasks and grown until confluent. The supernatant was then collected and concentrated using an amicon concentrator (Amicon, Inc., Beverly, Mass., USA). The concentrated supernatant was analyzed by SDS-PAGE, immunoblotting and ELISA for the Tumstatin expression. Strong binding in the supernatant was detected by ELISA.

Tumstatin-containing supernatant was subjected to affinity chromatography and immunodetected with both anti-tumstatin and anti-6-Histidine tag antibodies (Gunwar, S. et al., 1991, J. Biol. Chem. 266:15318–24). A major peak was identified, containing a monomer of about 31 kDa that was immunoreactive with Tumstatin antibodies.

Example 20

Tumstatin Inhibits Endothelial Cell Proliferation

The anti-proliferative effect of tumstatin on C-PAE cells was examined by $^3$H-thymidine incorporation assay using *E. coli* produced soluble protein.

Cell lines and culture. 786-O (renal clear cell carcinoma line), PC-3 (human prostate adenocarcinoma cell line), C-PAE (bovine pulmonary arterial endothelial cell line), MAE (mouse aortic endothelial cell line) cell were all obtained from American Type Culture Collection. The 786-O and C-PAE cell lines were maintained in DMEM (Life Technologies/Gibco BRL, Gaithersburg, Md., USA), the ECV-304 cells in M199, and the MAE cells in EGM-2 (Clonetics Corporation, San Diego, Calif., USA) supplemented with 10% fetal calf serum (FCS), 100 units/ml of penicillin, and 100 mg/ml of streptomycin.

Proliferation assay. C-PAE cells were grown to confluence in DMEM with 10% FCS and kept contact-inhibited for 48 hours. C-PAE cells were used between the second and fourth passages. 786-O and PC-3 cells were used as non-endothelial controls in this experiment. Cells were harvested by trypsinization (Life Technologies/Gibco BRL, Gaithersberg, Md., USA) at 37° C. for 5 minutes. A suspension of 12,500 cells in DMEM with 0.1% FCS was added to each well of a 24-well plate coated with 10 μg/ml fibronectin. The cells were incubated for 24 hours at 37° C. with 5% $CO_2$ and 95% humidity. Medium was removed and replaced with DMEM containing 20% FCS. Unstimulated control cells were incubated with 0.1% FCS. Cells were treated with various concentrations of Tumstatin ranging from 0.01 to 10 mg/ml. All wells received 1 mCurie of $^3$H-thymidine 12 hours after the beginning of treatment. After 24 hours, medium was removed and the wells were washed with PBS three times. Cells were extracted with 1N NaOH and added to a scintillation vial containing 4 ml of ScintiVerse II (Fisher Scientific, Pittsburgh, Pa., USA) solution. Thymidine incorporation was measured using a scintillation counter.

The results are shown in FIGS. 19A, 19B and 19C, which are histograms showing $^3$H-thymidine incorporation (y-axis) for C-PAE cells (FIG. 19A), PC-3 cells (FIG. 19B) and 786-O cells (FIG. 19C) when treated with varying concentrations of Tumstatin (x-axis). All groups represent triplicate samples. Tumstatin significantly inhibited 20% FCS stimulated $^3$H-thymidine incorporation in a dose dependent manner with an $ED_{50}$ of approximately 0.01 mg/ml (FIG. 19A). Also, no significant anti-proliferative effect was observed with prostate cancer cells (PC-3) or renal carcinoma cells (786-O) even at tumstatin doses of up to 20 mg/ml (FIGS. 19B and 19C). The difference between the mean value of $^3$H-thymidine incorporation in Tumstatin treated (0.1–10 mg/ml) and control was significant (P<0.05). When PC-3 cells or 786-O cells were treated with Tumstatin, no inhibitory effect was observed (FIGS. 19B, 19C). Each column represents the mean±SE of triplicate wells. This experiment was repeated for three times. Bars marked with an asterisk are significant, with P<0.05 by one tailed Student's t test.

Example 21

Tumstatin Inhibits Endothelial Tube Formation

Matrigel (Collaborative Biomedical Products, Bedford, Mass., USA) was added (320 μl) to each well of a 24-well plate and allowed to polymerize (Grant, D. S. et al., 1994, Pathol. Res. Pract. 190:854–63). A suspension of 25,000 MAE cells in EGM-2 medium (Clonetics Corporation, San Diego, Calif., USA) without antibiotic was passed into each well coated with matrigel (Grant, D. S. et al., 1994, Pathol. Res. Pract. 190:854–63). The cells were treated with either Tumstatin, BSA or 7S domain in increasing concentrations. Control cells were incubated with sterile PBS. All assays were performed in triplicate. Cells were incubated for 24–48 hours at 37° C. and viewed using a CK2 Olympus microscope (magnification of 3.3× ocular, 10× objective). The cells were then photographed using 400 DK coated TMAX film (Kodak). Cells were stained with diff-quik fixative (Sigma Chemical Co., St. Louis, Mo., USA) and photographed again (Grant, D. S. et al., 1994, Pathol. Res. Pract. 190:854–63). Ten fields were viewed, and the number of tubes were counted by two investigators unaware of the experimental protocols, and averaged.

The results are shown in FIG. 20. When mouse aortic endothelial cells are cultured on matrigel, a solid gel of mouse basement membrane proteins, they rapidly align and form hollow tube-like structures (Haralabopoulos, G. C. et al., 1994, Lab. Invest. 71:575–82). Tumstatin, produced in 293 cells, significantly inhibited endothelial tube formation in MAE cells in a dose dependent manner as compared to BSA controls (FIG. 20). Percentage of tube formation after treatment with 1 mg/ml of protein was, BSA 98.0±4.0, tumstatin 14.0±4.0. Similar results were also obtained using *E. coli* produced tumstatin. The 7S domain of type IV collagen (N-terminal non-collagenous domain) had no effect on endothelial tube formation. Maximum inhibition with tumstatin was attained between 800–1000 ng/ml. The difference between the mean percentage value of Tumstatin-treated (●, 0.1–10 mg/ml) and control (BSA (L), 7S domain (○)) was significant (P<0.05). Each point represents the mean±SE of triplicate wells. This experiment was repeated three times. Data points marked by an asterisk were significant, with P<0.05 by one tailed Student's t test. Well-formed tubes were observed in the 7S domain treatments. MAE cells treated with 0.8 mg/ml Tumstatin exhibiting decreased tube formation.

To evaluate the in vivo effect of tumstatin on the formation of new capillaries, a matrigel plug assay was performed (Passaniti, A. et al., 1992, Lab Invest. 67:519–29). Five- to six-week-old male C57/BL6 mice (Jackson Laboratories, Bar Harbor, Me., USA) were obtained. Matrigel (Collaborative Biomedical Products, Bedford, Mass., USA) was thawed overnight at 4° C. Before injection into C57/BL6 mice, it was mixed with 20 U/ml of heparin (Pierce Chemical Co., Rockford, Ill., USA), 150 ng/ml of bFGF (R&D Systems, Minneapolis, Minn., USA), and 1 mg/ml of Tumstatin. Control groups received no angiogenic inhibitor. The Matrigel mixture was injected sub-cutaneously using a 21 gauge needle. After 14 days, mice were sacrificed and the Matrigel plugs were removed. Matrigel plugs were fixed in 4% para-formaldehyde (in PBS) for 4 hours at room temperature, then switched to PBS for 24 hours. The plugs were embedded in paraffin, sectioned, and H & E stained. Sections were examined by light microscopy and the number of blood vessels from 10 high power fields were counted and averaged. All sections were coded and observed by a pathologist who was unaware of the study protocols.

When Matrigel was placed in the presence of bFGF and heparin, with or without E. coli-produced tumstatin, a 67% reduction in the number of blood vessels was observed with treatment of 1 mg/ml tumstatin. The number of vessels per high power field was, tumstatin, 2.25±1.32 and control, 7.50±2.17. Each column represents the mean±SE of 5–6 mice per group. Tumstatin (1 mg/ml) significantly inhibited in vivo neo-vascularization as compared to controls treated with PBS. The difference between the mean percentage value of Tumstatin-treated animals and control animals was significant (P<0.05). The Tumstatin treatment was significant, with P<0.05 by one tailed Student's t test.

Example 22

Tumstatin and Tumstatin Mutant Inhibit Tumor Growth in vivo

Five million PC-3 cells were harvested and injected subcutaneously on the back of 7- to 9-week-old male athymic nude mice. The tumors were measured using Vernier calipers and the volume was calculated using the standard formula width$^2$×length×0.52. The tumors were allowed to grow to about 100 mm$^3$, and animals were then divided into groups of 5 or 6 mice. Tumstatin or mouse endostatin was intraperitoneally injected daily (20 mg/kg) for 10 days in sterile PBS to their respective experimental group. The control group received vehicle injection (either BSA or PBS). Tumor volume was calculated every 2 or 3 days over 10 days. The results are shown in FIG. 21A, which is a graph showing tumor volume in mm$^3$ (y-axis) against days of treatment (x-axis) for the PBS control (□), 20 mg/kg Tumstatin (●) and 20 mg/kg endostatin (○). Tumstatin, produced in E. coli, significantly inhibited the growth of PC-3 human prostate tumors (FIG. 21A). Tumstatin at 20 mg/Kg inhibited tumor growth similar to endostatin at 20 mg/kg (FIG. 21A). Significant inhibitory effect on tumor growth was observed on day 10 (control 202.8±50.0 mm$^3$, tumstatin 82.9±−25.2 mm$^3$, endostatin 68.9±16.7 mm$^3$). Daily intraperitoneal injection of Tumstatin or endostatin inhibited the growth of human prostate adenocarcinoma cell (PC-3) tumor as compared to the control. This experiment was started when the tumor volumes were less than 100 mm$^3$.

Tumstatin's effect on another established primary tumors in mice was also studied. Two million 786-O renal cell carcinoma cells were injected subcutaneously on the back of 7- to 9-week-old male athymic nude mice. The tumors were allowed to grow to about 600 to about 700 mm$^3$ and animals were then divided into groups of 6. Tumstatin was intraperitoneally injected daily (6 mg/kg) for 10 days in sterile PBS. The control group received BSA injections. The results are shown in FIG. 21B, which is a graph showing tumor volume in mm$^3$ (y-axis) against days of treatment (x-axis) for the PBS control (□) and for 6 mg/kg Tumstatin (●). E. coli-produced Tumstatin at 6 mg/kg inhibited the tumor growth of 786-O human renal cell carcinoma as compared to the BSA control (FIG. 21B). Significant inhibitory effect on tumor growth was observed on day 10 (control 1096±179.7 mm$^3$, tumstatin 619±120.7 mm$^3$). Daily intraperitoneal injection of Tumstatin inhibited the tumor growth of human renal cell carcinoma (786-O) as compared to the control. This experiment was started when the tumor volumes were 600–700 mm$^3$. Each point represents the mean±SE of 5–6 mice per group. Data points marker with an asterisk were significant, with P<0.05 by one tailed Student's t test.

A portion of the NC1 domain of the α3 chain of type IV collagen (α3 (IV) NC1) is the pathogenic epitope of Goodpasture syndrome (Butkowski, R. J. et al., 1987, J. Biol. Chem. 262:7874–7; Saus, J. et al., 1988, J. Biol. Chem. 263:13374–80; Kalluri, R. et al., 1991, J. Biol. Chem. 266:24018–24). Goodpasture syndrome is an autoimmune disease characterized by pulmonary hemorrhage and/or rapidly progressing glomerulonephritis (Wilson, C. & F. Dixon, 1986, The Kidney, W.B. Sanders Co., Philadelphia, Pa., USA, pps. 800–89; Hudson, B. G. et al., 1993, J. Biol. Chem. 268:16033–6). These symptoms are caused by the disruption of glomerular and alveolar basement membrane through binding of auto-antibody against α3 (IV) NC1 (Wilson, 1986, supra; Hudson, 1993, supra). Several groups have attempted to map or predict the location of the Goodpasture autoantigen on α3 (IV) (Kalluri, R. et al., 1995, J. Am. Soc. Nephrol. 6:1178–85; Kalluri, R. et al., 1996, J. Biol. Chem. 271:9062–8; Levy, J. B. et al., 1997, J. Am. Soc. Nephrol. 8:1698–1705; Kefalides, N. A. et al., 1993, Kidney Int. 43:94–100; Quinones, S. et al., 1992, J. Biol. Chem. 267:19780–4 (erratum in J. Biol. Chem 269:17358); Netzer, K. O. et al., 1999, J. Biol. Chem. 274:11267–74), residues in the N-terminus, C-terminus, and mid-portion have been reported to be the epitope position. Recently, the most probable disease-related pathogenic epitope was identified in the N-terminal portion (Hellmark, T. et al., 1999, Kidney Int. 55:936–44) and was further confined to be the N-terminal 40 amino acids. A truncated tumstatin was designed lacking N-terminal 53 amino acids (Tumstatin-N53) corresponding to the pathogenic Goodpasture auto-epitopes. This mutant protein was used in the following exeriments.

Two million 786-O renal cell carcinoma cells were injected subcutaneously on the back of 7- to 9-week-old male athymic nude mice. The tumors were allowed to grow to a size of about 100–150 mm$^3$. The mice were then divided into groups of 5, and were injected daily intraperitoneally with 20 mg/kg of the E. coli-expressed truncated Tumstatin lacking the 53 N-terminal amino acids (Kalluri, R. et al.,

49

Figure 22:
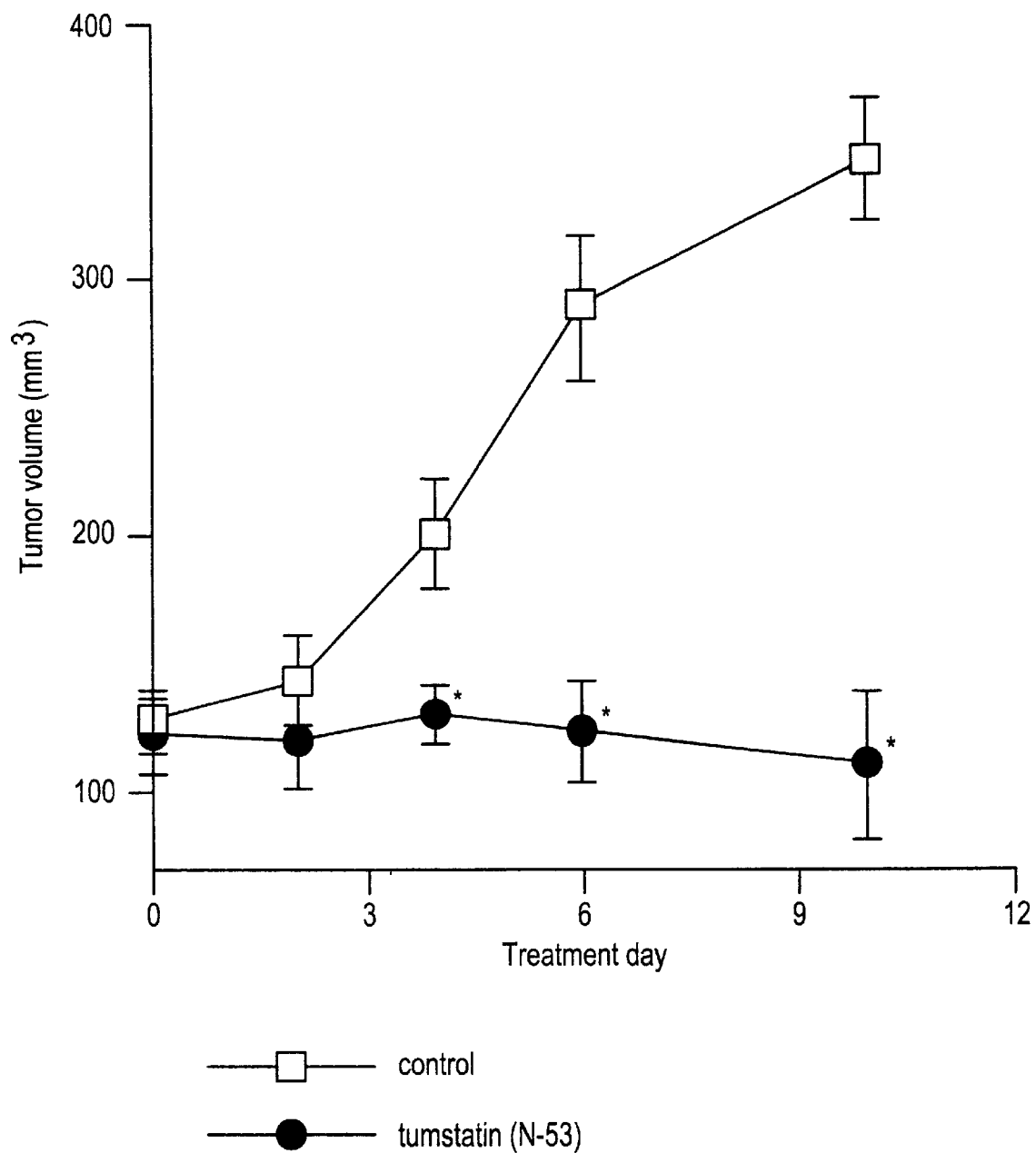
FIG. 22 is a graph showing increase in tumor volume (y-axis) against day of treatment (x-axis) for control mice (□) and mice treated with the Tumstatin mutant N-53 (●). Data points marked with an asterisk are significant, with $P<0.05$ by one-tailed Student's test.

1996, J. Biol. Chem. 271:9062–8) for 10 days. Control mice received PBS injection. The results are shown in FIG. 22, which is a graph showing increase in tumor volume (y-axis) against day of treatment (x-axis) for control mice (□) and mice treated with the Tumstatin mutant N53 (●). *E. coli*-produced tumstatin-N53 at 20 mg/kg inhibited the growth of 786-O human renal tumors significantly from day 4 to day 10 as compared to control (day 10: tumstatin-N53 110.0±29.0 mm³, control 345.0±24.0 mm³) (FIG. 22). Each point represents the mean±SE of 5–6 mice/group. Data points marked with an asterisk were significant, with P<0.05 by one tailed Student's t test.

Example 23

Immunohistochemical Staining for α3 (IV) NC1 and CD31

Kidney and skin tissue from a 7-week-old male C57/BL6 mouse was processed for evaluation by immunofluorescence microscopy. The tissue samples were frozen in liquid nitrogen, and sections 4 mm thick were used. Tissue was processed by indirect immunofluorescence technique as previously described (Kalluri, R. et al., 1996, J. Biol. Chem. 271:9062–8). Frozen sections were stained with the primary antibodies, polyclonal anti-CD31 antibody (1:100 dilution) or polyclonal anti-α3 (IV) NC1 antibody (1:50 dilution), followed by the secondary antibody, FITC-conjugated anti-rat IgG antibody or FITC-conjugated anti-human IgG antibody. Immunofluorescence was examined under an Olympus fluorescent microscope (Tokyo, Japan). Negative controls were performed by substituting the primary antibody with an irrelevant pre-immune serum.

In mouse kidney, expression of α3 (IV) NC1 was observed in GBM and in vascular basement membrane. The expression of CD31, PECAM-1, was observed in glomerular endothelium and vascular endothelium. In mouse skin, α3 (IV) NC1 was absent in epidermal basement membrane and vascular basement membranes. The expression of CD31 was observed in vascular endothelium of the skin. CD31 expression was observed in the endothelium of glomeruli and small vessels in mouse kidney α3 (IV) NC1 expression was observed in glomerular basement membrane and in extraglomerular vascular basement membranes. Expression of CD31 was observed in the endothelium of dermal small vessels in mouse skin. α3 (IV) NC1 expression was absent in the epidermal basement membrane and almost not observed in the basement membrane of dermal small vessels. These results show an example of restricted distribution of tumstatin.

Example 24

Mutants and Fragments of the Anti-angiogenic Proteins

Fragments and mutants of Arresten and Canstatin were also made according to the Pseudomonas elastase digestions of Mariyama et al. (1992, J. Biol. Chem. 267:1253–8). The digest was resolved by gel filtration HPLC and the resultant fragments were analyzed by SDS-PAGE and evaluated in the endothelial tube assay described above. These fragments included a 12 kDa fragment of Arresten, an 8 kDa fragment of Arresten, and a 10 kDa fragment of Canstatin. In addition, two fragments of Tumstatin ('333' and '334') were generated by PCR cloning.

Figure 23:
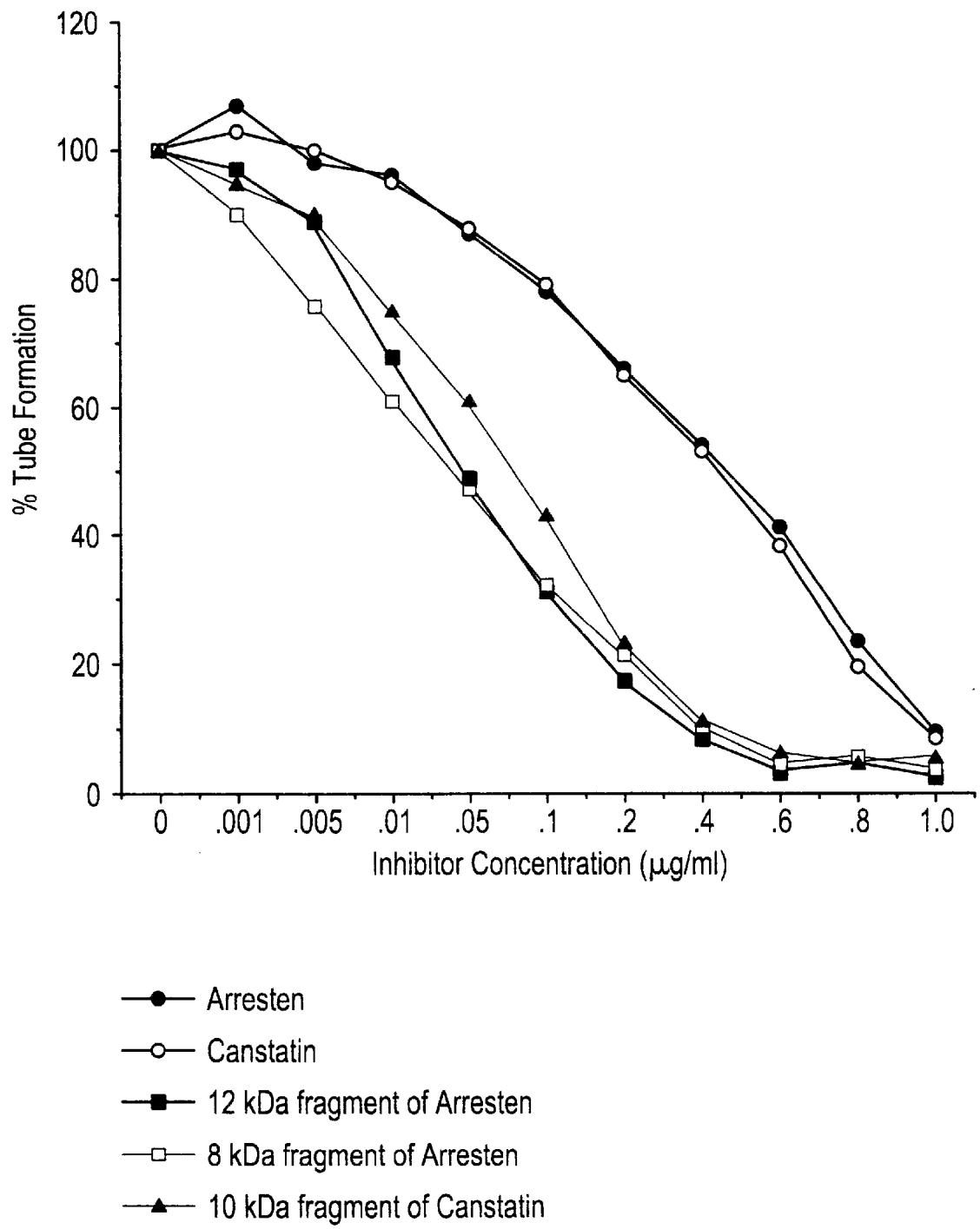
FIG. 23 is a line graph showing the inhibition of endothelial tube formation (y-axis) by varying concentrations (x-axis) of Arresten (●), Canstatin (○), the 12 kDa Arresten fragment (■), the 8 kDa Arresten fragment (□), and the 10 kDa Canstatin fragment (▲).
Figure 24:
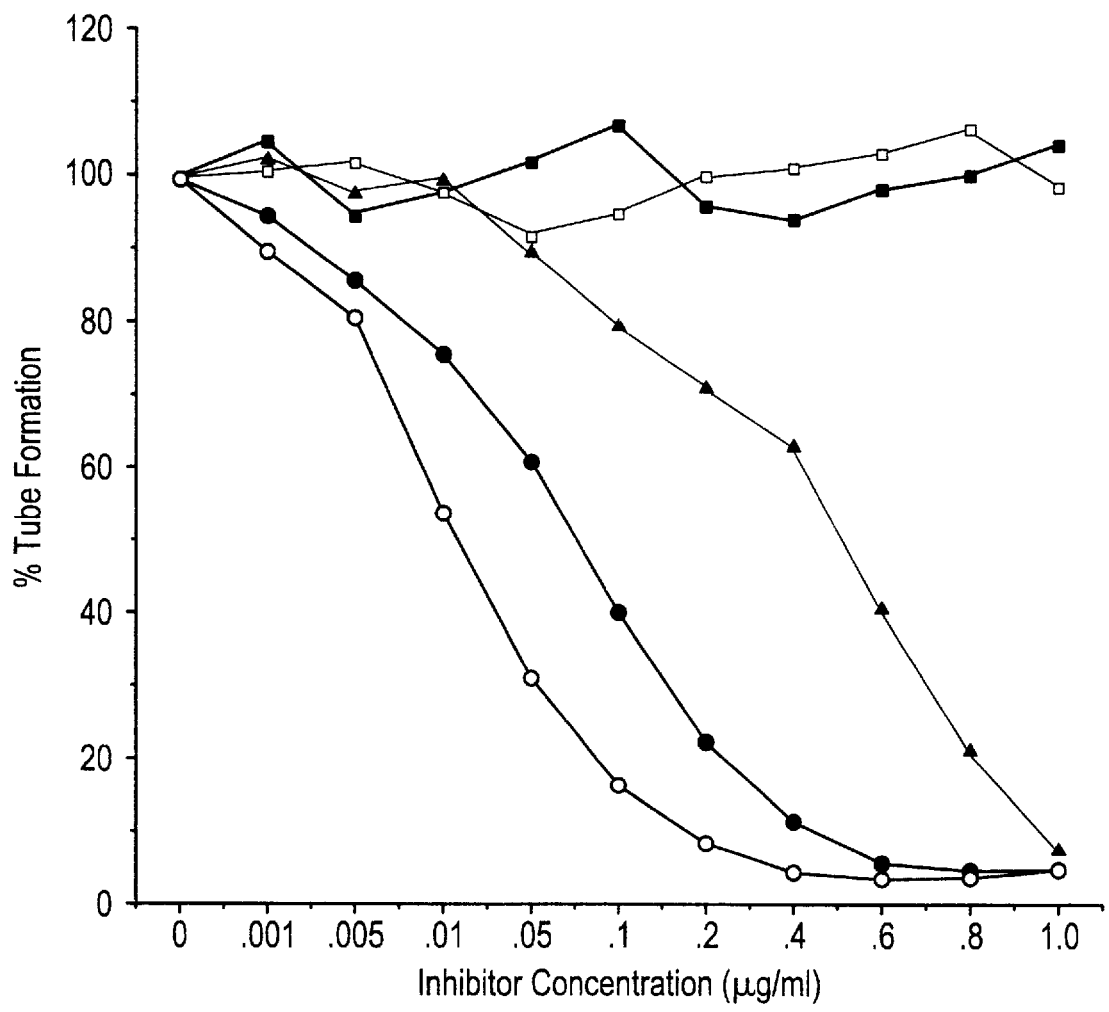
FIG. 24 is a line graph showing the inhibition of endothelial tube formation (y-axis) by varying concentrations (x-axis) of Tumstatin fragment 333 (●), Tumstatin fragment 334 (○), BSA (control, ■), α6 (control, □), and Tumstatin (▲).

As shown in FIG. 23, the endothelial tube assay, performed as described above, the two Arresten fragments (12 kDa (●) and 8 kDa (□)) and the Canstatin fragment (19 kDa (▲)) inhibited the formation of endothelial tubes to an even greater extent than did Arresten (●) or Canstatin (○). FIG. 24 shows that the Tumstatin fragments, "333" (●) and "334" (○) likewise outperformed Tumstatin (▲), with BSA (■) and the α6 chain (□) serving as controls.

All references, patents, and patent applications are incorporated herein by reference in their entirety. While this invention has been particularly shown and described with references to preferred embodiments thereof, it will be understood by those of ordinary skill in the art that various changes in form and details may be made therein without departing from the spirit and scope of the invention as defined by the appended claims.

What is claimed is:

1. A method for inhibiting angiogenic activity in mammalian tissue, the method comprising contacting the tissue with a composition comprising an isolated protein selected from the group consisting of: the NC1 domain of the α1 chain of Type IV collagen (SEQ ID NO:2), the NC1 domain of the α2 chain of Type IV collagen (SEQ ID NO:6), and the NC1 domain of the α3 chain of Type IV collagen (SEQ ID NO:10).

2. The method of claim 1, wherein the angiogenic activity is characteristic of an angiogenesis-dependent cancer or benign tumor.

3. The method of claim 1, wherein said method is in conjunction with radiation therapy, chemotherapy, or immunotherapy.

4. A method for inhibiting angiogenic activity in mammalian tissue, comprising contacting the tissue with a composition comprising the NC1 domain of the α1 chain of human type IV collagen having the amino acid sequence of SEQ ID NO:2.

5. A method for inhibiting angiogenic activity in mammalian tissue, comprising contacting the tissue with a composition comprising the NC1 domain of the α2 chain of human type IV collagen having the amino acid sequence of SEQ ID NO:6.

6. A method for inhibiting angiogenic activity in mammalian tissue, comprising contacting the tissue with a composition comprising the NC1 domain of the α3 chain of human type IV collagen having the amino acid sequence of SEQ ID NO:10.

7. A method for inhibiting angiogenic activity in mammalian tissue, comprising contacting the tissue with a composition comprising a fragment of an α1 chain of human type IV collagen, wherein said fragment is a 12 kDa fragment of SEQ ID NO:2.

8. A method for inhibiting angiogenic activity in mammalian tissue, comprising contacting the tissue with a composition comprising a fragment of an α1 chain of human type IV collagen, wherein said fragment is a 8 kDa fragment of SEQ ID NO:2.

9. A method for inhibiting angiogenic activity in mammalian tissue, comprising contacting the tissue with a composition comprising a fragment of an α2 chain of human type IV collagen, wherein said fragment is a 10 kDa fragment of SEQ ID NO:6.

10. A method for inhibiting angiogenic activity in mammalian tissue, comprising contacting the tissue with a composition comprising a fragment of an α3 chain of human type IV collagen, consisting of amino acids 1–124 of SEQ ID NO:10.

11. A method for inhibiting angiogenic activity in mammalian tissue, comprising contacting the tissue with a composition comprising a fragment of an α3 chain of human type IV collagen, consisting of amino acids 125–244 of SEQ ID NO:10.

12. A method for inhibiting angiogenic activity in mammalian tissue, comprising contacting the tissue with a composition comprising a fragment of an α3 chain of human type IV collagen, consisting of amino acids 53–243 of SEQ ID NO:10.

* * * * *

SEQUENCE LISTING

```
<160> NUMBER OF SEQ ID NOS: 18

<210> SEQ ID NO 1
<211> LENGTH: 690
<212> TYPE: DNA
<213> ORGANISM: Homo sapiens
<220> FEATURE:
<221> NAME/KEY: CDS
<222> LOCATION: (1)..(687)
<223> OTHER INFORMATION:

<400> SEQUENCE: 1 tct gtt gat cac ggc ttc ctt gtg acc agg cat agt caa aca ata gat        48
Ser Val Asp His Gly Phe Leu Val Thr Arg His Ser Gln Thr Ile Asp
1               5                   10                  15 gac cca cag tgt cct tct ggg acc aaa att ctt tac cac ggg tac tct        96
Asp Pro Gln Cys Pro Ser Gly Thr Lys Ile Leu Tyr His Gly Tyr Ser
            20                  25                  30 ttg ctc tac gtg caa ggc aat gaa cgg gcc cat gga cag gac ttg ggc       144
Leu Leu Tyr Val Gln Gly Asn Glu Arg Ala His Gly Gln Asp Leu Gly
        35                  40                  45
```

```
acg gcc ggc agc tgc ctg cgc aag ttc agc aca atg ccc ttc ctg ttc      192
Thr Ala Gly Ser Cys Leu Arg Lys Phe Ser Thr Met Pro Phe Leu Phe
 50                  55                  60 tgc aat att aac aac gtg tgc aac ttt gca tca cga aat gac tac tcg      240
Cys Asn Ile Asn Asn Val Cys Asn Phe Ala Ser Arg Asn Asp Tyr Ser
 65                  70                  75                  80 tac tgg ctg tcc acc cct gag ccc atg ccc atg tca atg gca ccc atc      288
Tyr Trp Leu Ser Thr Pro Glu Pro Met Pro Met Ser Met Ala Pro Ile
                 85                  90                  95 acg ggg gaa aac ata aga cca ttt att agt agg tgt gct gtg tgt gag      336
Thr Gly Glu Asn Ile Arg Pro Phe Ile Ser Arg Cys Ala Val Cys Glu
             100                 105                 110 gcg cct gcc atg gtg atg gcc gtg cac agc cag acc att cag atc cca      384
Ala Pro Ala Met Val Met Ala Val His Ser Gln Thr Ile Gln Ile Pro
         115                 120                 125 ccg tgc ccc agc ggg tgg tcc tcg ctg tgg atc ggc tac tct ttt gtg      432
Pro Cys Pro Ser Gly Trp Ser Ser Leu Trp Ile Gly Tyr Ser Phe Val
130                 135                 140 atg cac acc agc gct ggt gca gaa ggc tct ggc caa gcc ctg gcg tcc      480
Met His Thr Ser Ala Gly Ala Glu Gly Ser Gly Gln Ala Leu Ala Ser
145                 150                 155                 160 ccc ggc tcc tgc ctg gag gag ttt aga agt gcg cca ttc atc gag tgt      528
Pro Gly Ser Cys Leu Glu Glu Phe Arg Ser Ala Pro Phe Ile Glu Cys
                165                 170                 175 cac ggc cgt ggg acc tgc aat tac tac gca aac gct tac agc ttt tgg      576
His Gly Arg Gly Thr Cys Asn Tyr Tyr Ala Asn Ala Tyr Ser Phe Trp
            180                 185                 190 ctc gcc acc ata gag agg agc gag atg ttc aag aag cct acg ccg tcc      624
Leu Ala Thr Ile Glu Arg Ser Glu Met Phe Lys Lys Pro Thr Pro Ser
        195                 200                 205 acc ttg aag gca ggg gag ctg cgc acg cac gtc agc cgc tgc caa gtc      672
Thr Leu Lys Ala Gly Glu Leu Arg Thr His Val Ser Arg Cys Gln Val
210                 215                 220 tgt atg aga aga aca taa                                              690
Cys Met Arg Arg Thr
225
```

<210> SEQ ID NO 2
<211> LENGTH: 229
<212> TYPE: PRT
<213> ORGANISM: Homo sapiens

<400> SEQUENCE: 2

```
Ser Val Asp His Gly Phe Leu Val Thr Arg His Ser Gln Thr Ile Asp
  1               5                  10                  15

Asp Pro Gln Cys Pro Ser Gly Thr Lys Ile Leu Tyr His Gly Tyr Ser
             20                  25                  30

Leu Leu Tyr Val Gln Gly Asn Glu Arg Ala His Gly Gln Asp Leu Gly
         35                  40                  45

Thr Ala Gly Ser Cys Leu Arg Lys Phe Ser Thr Met Pro Phe Leu Phe
 50                  55                  60

Cys Asn Ile Asn Asn Val Cys Asn Phe Ala Ser Arg Asn Asp Tyr Ser
 65                  70                  75                  80

Tyr Trp Leu Ser Thr Pro Glu Pro Met Pro Met Ser Met Ala Pro Ile
                 85                  90                  95

Thr Gly Glu Asn Ile Arg Pro Phe Ile Ser Arg Cys Ala Val Cys Glu
             100                 105                 110

Ala Pro Ala Met Val Met Ala Val His Ser Gln Thr Ile Gln Ile Pro
         115                 120                 125
```

```
Pro Cys Pro Ser Gly Trp Ser Ser Leu Trp Ile Gly Tyr Ser Phe Val
    130                 135                 140
Met His Thr Ser Ala Gly Ala Glu Gly Ser Gly Gln Ala Leu Ala Ser
145                 150                 155                 160
Pro Gly Ser Cys Leu Glu Glu Phe Arg Ser Ala Pro Phe Ile Glu Cys
                165                 170                 175
His Gly Arg Gly Thr Cys Asn Tyr Tyr Ala Asn Ala Tyr Ser Phe Trp
            180                 185                 190
Leu Ala Thr Ile Glu Arg Ser Glu Met Phe Lys Lys Pro Thr Pro Ser
        195                 200                 205
Thr Leu Lys Ala Gly Glu Leu Arg Thr His Val Ser Arg Cys Gln Val
    210                 215                 220
Cys Met Arg Arg Thr
225
```

<210> SEQ ID NO 3
<211> LENGTH: 27
<212> TYPE: DNA
<213> ORGANISM: Artificial sequence
<220> FEATURE:
<223> OTHER INFORMATION: pET22b(+) forward oligonucleotide primer for Arresten

<400> SEQUENCE: 3
cgggatcctt ctgttgatca cggcttc         27

<210> SEQ ID NO 4
<211> LENGTH: 27
<212> TYPE: DNA
<213> ORGANISM: Artificial sequence
<220> FEATURE:
<223> OTHER INFORMATION: pET22b(+) reverse oligonuceotide primer for Arresten

<400> SEQUENCE: 4
cccaagcttt gttcttctca tacagac         27

<210> SEQ ID NO 5
<211> LENGTH: 684
<212> TYPE: DNA
<213> ORGANISM: Homo sapiens
<220> FEATURE:
<221> NAME/KEY: CDS
<222> LOCATION: (1)..(681)
<223> OTHER INFORMATION:

<400> SEQUENCE: 5

```
gtc agc atc ggc tac ctc ctg gtg aag cac agc cag acg gac cag gag    48
Val Ser Ile Gly Tyr Leu Leu Val Lys His Ser Gln Thr Asp Gln Glu
1               5                  10                  15 ccc atg tgc ccg gtg ggc atg aac aaa ctc tgg agt gga tac agc ctg    96
Pro Met Cys Pro Val Gly Met Asn Lys Leu Trp Ser Gly Tyr Ser Leu
                20                  25                  30 ctg tac ttc gag ggc cag gag aag gcg cac aac cag gac ctg ggg ctg   144
Leu Tyr Phe Glu Gly Gln Glu Lys Ala His Asn Gln Asp Leu Gly Leu
            35                  40                  45 gcg ggc tcc tgc ctg gcg cgg ttc agc acc atg ccc ttc ctg tac tgc   192
Ala Gly Ser Cys Leu Ala Arg Phe Ser Thr Met Pro Phe Leu Tyr Cys
        50                  55                  60 aac cct ggt gat gtc tgc tac tat gcc agc cgg aac gac aag tcc tac   240
Asn Pro Gly Asp Val Cys Tyr Tyr Ala Ser Arg Asn Asp Lys Ser Tyr
65                  70                  75                  80
```

```
tgg ctc tct acc act gcg ccg ctg ccc atg atg ccc gtg gcc gag gac      288
Trp Leu Ser Thr Thr Ala Pro Leu Pro Met Met Pro Val Ala Glu Asp
            85                  90                  95 gag atc aag ccc tac atc agc cgc tgt tct gtg tgt gag gcc ccg gcc      336
Glu Ile Lys Pro Tyr Ile Ser Arg Cys Ser Val Cys Glu Ala Pro Ala
        100                 105                 110 atc gcc atc gcg gtc cac agt cag gat gtc tcc atc cca cac tgc cca      384
Ile Ala Ile Ala Val His Ser Gln Asp Val Ser Ile Pro His Cys Pro
    115                 120                 125 gct ggg tgg cgg agt ttg tgg atc gga tat tcc ttc ctc atg cac acg      432
Ala Gly Trp Arg Ser Leu Trp Ile Gly Tyr Ser Phe Leu Met His Thr
130                 135                 140 gcg gcg gga gac gaa ggc ggt ggc caa tca ctg gtg tca ccg ggc agc      480
Ala Ala Gly Asp Glu Gly Gly Gly Gln Ser Leu Val Ser Pro Gly Ser
145                 150                 155                 160 tgt cta gag gac ttc cgc gcc aca cca ttc atc gaa tgc aat gga ggc      528
Cys Leu Glu Asp Phe Arg Ala Thr Pro Phe Ile Glu Cys Asn Gly Gly
                165                 170                 175 cgc ggc acc tgc cac tac tac gcc aac aag tac agc ttc tgg ctg acc      576
Arg Gly Thr Cys His Tyr Tyr Ala Asn Lys Tyr Ser Phe Trp Leu Thr
            180                 185                 190 acc att ccc gag cag agc ttc cag ggc tcg ccc tcc gcc gac acg ctc      624
Thr Ile Pro Glu Gln Ser Phe Gln Gly Ser Pro Ser Ala Asp Thr Leu
        195                 200                 205 aag gcc ggc ctc atc cgc aca cac atc agc cgc tgc cag gtg tgc atg      672
Lys Ala Gly Leu Ile Arg Thr His Ile Ser Arg Cys Gln Val Cys Met
    210                 215                 220 aag aac ctg tga                                                      684
Lys Asn Leu
225
```

<210> SEQ ID NO 6
<211> LENGTH: 227
<212> TYPE: PRT
<213> ORGANISM: Homo sapiens

<400> SEQUENCE: 6

```
Val Ser Ile Gly Tyr Leu Leu Val Lys His Ser Gln Thr Asp Gln Glu
1               5                   10                  15

Pro Met Cys Pro Val Gly Met Asn Lys Leu Trp Ser Gly Tyr Ser Leu
            20                  25                  30

Leu Tyr Phe Glu Gly Gln Glu Lys Ala His Asn Gln Asp Leu Gly Leu
        35                  40                  45

Ala Gly Ser Cys Leu Ala Arg Phe Ser Thr Met Pro Phe Leu Tyr Cys
    50                  55                  60

Asn Pro Gly Asp Val Cys Tyr Tyr Ala Ser Arg Asn Asp Lys Ser Tyr
65                  70                  75                  80

Trp Leu Ser Thr Thr Ala Pro Leu Pro Met Met Pro Val Ala Glu Asp
                85                  90                  95

Glu Ile Lys Pro Tyr Ile Ser Arg Cys Ser Val Cys Glu Ala Pro Ala
            100                 105                 110

Ile Ala Ile Ala Val His Ser Gln Asp Val Ser Ile Pro His Cys Pro
        115                 120                 125

Ala Gly Trp Arg Ser Leu Trp Ile Gly Tyr Ser Phe Leu Met His Thr
    130                 135                 140

Ala Ala Gly Asp Glu Gly Gly Gly Gln Ser Leu Val Ser Pro Gly Ser
145                 150                 155                 160
```

-continued

```
Cys Leu Glu Asp Phe Arg Ala Thr Pro Phe Ile Glu Cys Asn Gly Gly
            165                 170                 175

Arg Gly Thr Cys His Tyr Tyr Ala Asn Lys Tyr Ser Phe Trp Leu Thr
            180                 185                 190

Thr Ile Pro Glu Gln Ser Phe Gln Gly Ser Pro Ser Ala Asp Thr Leu
            195                 200                 205

Lys Ala Gly Leu Ile Arg Thr His Ile Ser Arg Cys Gln Val Cys Met
    210                 215                 220

Lys Asn Leu
225

<210> SEQ ID NO 7
<211> LENGTH: 27
<212> TYPE: DNA
<213> ORGANISM: Artificial sequence
<220> FEATURE:
<223> OTHER INFORMATION: pET22b(+) forward oligonucleotide primer for
      Canstatin

<400> SEQUENCE: 7
cgggatcctg tcagcatcgg ctacctc                                          27

<210> SEQ ID NO 8
<211> LENGTH: 27
<212> TYPE: DNA
<213> ORGANISM: Artificial sequence
<220> FEATURE:
<223> OTHER INFORMATION: pET22b(+) reverse oligonucleotide primer for
      Canstatin

<400> SEQUENCE: 8
cccaagcttc aggttcttca tgcacac                                          27

<210> SEQ ID NO 9
<211> LENGTH: 735
<212> TYPE: DNA
<213> ORGANISM: Homo sapiens
<220> FEATURE:
<221> NAME/KEY: CDS
<222> LOCATION: (1)..(732)
<223> OTHER INFORMATION:
<220> FEATURE:
<221> NAME/KEY: misc_feature
<222> LOCATION: (160)..(732)
<223> OTHER INFORMATION: Tumstatin N53
<220> FEATURE:
<221> NAME/KEY: misc_feature
<222> LOCATION: (1)..(372)
<223> OTHER INFORMATION: Tumstatin 333
<220> FEATURE:
<221> NAME/KEY: misc_feature
<222> LOCATION: (373)..(732)
<223> OTHER INFORMATION: Tumstatin 334

<400> SEQUENCE: 9 ggt ttg aaa gga aaa cgt gga gac agt gga tca cct gca acc tgg aca       48
Gly Leu Lys Gly Lys Arg Gly Asp Ser Gly Ser Pro Ala Thr Trp Thr
1               5                   10                  15 acg aga ggc ttt gtc ttc acc cga cac agt caa acc aca gca att cct       96
Thr Arg Gly Phe Val Phe Thr Arg His Ser Gln Thr Thr Ala Ile Pro
                20                  25                  30 tca tgt cca gag ggg aca gtg cca ctc tac agt ggg ttt tct ttt ctt      144
Ser Cys Pro Glu Gly Thr Val Pro Leu Tyr Ser Gly Phe Ser Phe Leu
            35                  40                  45
```

```
ttt gta caa gga aat caa cga gcc cac gga caa gac ctt gga act ctt     192
Phe Val Gln Gly Asn Gln Arg Ala His Gly Gln Asp Leu Gly Thr Leu
     50                  55                  60 ggc agc tgc ctg cag cga ttt acc aca atg cca ttc tta ttc tgc aat     240
Gly Ser Cys Leu Gln Arg Phe Thr Thr Met Pro Phe Leu Phe Cys Asn
 65                  70                  75                  80 gtc aat gat gta tgt aat ttt gca tct cga aat gat tat tca tac tgg     288
Val Asn Asp Val Cys Asn Phe Ala Ser Arg Asn Asp Tyr Ser Tyr Trp
                 85                  90                  95 ctg tca aca cca gct ctg atg cca atg aac atg gct ccc att act ggc     336
Leu Ser Thr Pro Ala Leu Met Pro Met Asn Met Ala Pro Ile Thr Gly
             100                 105                 110 aga gcc ctt gag cct tat ata agc aga tgc act gtt tgt gaa ggt cct     384
Arg Ala Leu Glu Pro Tyr Ile Ser Arg Cys Thr Val Cys Glu Gly Pro
         115                 120                 125 gcg atc gcc ata gcc gtt cac agc caa acc act gac att cct cca tgt     432
Ala Ile Ala Ile Ala Val His Ser Gln Thr Thr Asp Ile Pro Pro Cys
 130                 135                 140 cct cac ggc tgg att tct ctc tgg aaa gga ttt tca ttc atc atg ttc     480
Pro His Gly Trp Ile Ser Leu Trp Lys Gly Phe Ser Phe Ile Met Phe
145                 150                 155                 160 aca agt gca ggt tct gag ggc acc ggg caa gca ctg gcc tcc cct ggc     528
Thr Ser Ala Gly Ser Glu Gly Thr Gly Gln Ala Leu Ala Ser Pro Gly
                 165                 170                 175 tcc tgc ctg gaa gaa ttc cga gcc agc cca ttt cta gaa tgt cat gga     576
Ser Cys Leu Glu Glu Phe Arg Ala Ser Pro Phe Leu Glu Cys His Gly
             180                 185                 190 aga gga acg tgc aac tac tat tca aat tcc tac agt ttc tgg ctg gct     624
Arg Gly Thr Cys Asn Tyr Tyr Ser Asn Ser Tyr Ser Phe Trp Leu Ala
         195                 200                 205 tca tta aac cca gaa aga atg ttc aga aag cct att cca tca act gtg     672
Ser Leu Asn Pro Glu Arg Met Phe Arg Lys Pro Ile Pro Ser Thr Val
 210                 215                 220 aaa gct ggg gaa tta gaa aaa ata ata agt cgc tgt cag gtg tgc atg     720
Lys Ala Gly Glu Leu Glu Lys Ile Ile Ser Arg Cys Gln Val Cys Met
225                 230                 235                 240 aag aaa aga cac tga                                                  735
Lys Lys Arg His <210> SEQ ID NO 10
<211> LENGTH: 244
<212> TYPE: PRT
<213> ORGANISM: Homo sapiens
<220> FEATURE:
<221> NAME/KEY: misc_feature
<222> LOCATION: (160)..(732)
<223> OTHER INFORMATION: Tumstatin N53
<220> FEATURE:
<221> NAME/KEY: misc_feature
<222> LOCATION: (1)..(372)
<223> OTHER INFORMATION: Tumstatin 333
<220> FEATURE:
<221> NAME/KEY: misc_feature
<222> LOCATION: (373)..(732)
<223> OTHER INFORMATION: Tumstatin 334

<400> SEQUENCE: 10

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
                 20                  25                  30

Ser Cys Pro Glu Gly Thr Val Pro Leu Tyr Ser Gly Phe Ser Phe Leu
             35                  40                  45
```

-continued

Phe Val Gln Gly Asn Gln Arg Ala His Gly Gln Asp Leu Gly Thr Leu
 50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
             85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175

Ser Cys Leu Glu Glu Phe Arg Ala Ser Pro Phe Leu Glu Cys His Gly
            180                 185                 190

Arg Gly Thr Cys Asn Tyr Tyr Ser Asn Ser Tyr Ser Phe Trp Leu Ala
        195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His

<210> SEQ ID NO 11
<211> LENGTH: 27
<212> TYPE: DNA
<213> ORGANISM: Artificial sequence
<220> FEATURE:
<223> OTHER INFORMATION: pET22b(+) forward oligonucleotide primer for
      Tumstatin

<400> SEQUENCE: 11
cgggatccgg gttttgaaagg aaaacgt                                    27

<210> SEQ ID NO 12
<211> LENGTH: 27
<212> TYPE: DNA
<213> ORGANISM: Artificial sequence
<220> FEATURE:
<223> OTHER INFORMATION: pET22b(+) reverse oligonucleotide primer for
      Tumstatin
<220> FEATURE:
<221> NAME/KEY: misc_feature
<222> LOCATION: (1)..(27)
<223> OTHER INFORMATION: primer

<400> SEQUENCE: 12
cccaagcttt cagtgtctttt tcttcat                                    27

<210> SEQ ID NO 13
<211> LENGTH: 8
<212> TYPE: PRT
<213> ORGANISM: Artificial sequence
<220> FEATURE:
<223> OTHER INFORMATION: Additional vector sequence added to protein

```
<400> SEQUENCE: 13

Met Asp Ile Gly Ile Asn Ser Asp
1               5

<210> SEQ ID NO 14
<211> LENGTH: 7
<212> TYPE: PRT
<213> ORGANISM: Artificial sequence
<220> FEATURE:
<223> OTHER INFORMATION: Additional vector sequence added to protein

<400> SEQUENCE: 14

Lys Leu Ala Ala Ala Leu Glu
1               5

<210> SEQ ID NO 15
<211> LENGTH: 28
<212> TYPE: DNA
<213> ORGANISM: Artificial sequence
<220> FEATURE:
<223> OTHER INFORMATION: pPICZaA forward oligonucleotide primer for
      Arresten

<400> SEQUENCE: 15
ttcggaattc tctgttgatc acggcttc                                         28

<210> SEQ ID NO 16
<211> LENGTH: 35
<212> TYPE: DNA
<213> ORGANISM: Artificial sequence
<220> FEATURE:
<223> OTHER INFORMATION: pPICZaA reverse oligonucleotide primer for
      Arresten

<400> SEQUENCE: 16
tgctctagag gtgttcttct catacagact tggca                                 35

<210> SEQ ID NO 17
<211> LENGTH: 31
<212> TYPE: DNA
<213> ORGANISM: Artificial sequence
<220> FEATURE:
<223> OTHER INFORMATION: pPICZaA forward oligonucleotide primer for
      Canstatin

<400> SEQUENCE: 17
ttcggaattc gtcagcatcg gctacctcct g                                     31

<210> SEQ ID NO 18
<211> LENGTH: 32
<212> TYPE: DNA
<213> ORGANISM: Artificial sequence
<220> FEATURE:
<223> OTHER INFORMATION: pPICZaA reverse oligonucleotide primer for
      Canstatin

<400> SEQUENCE: 18
ggggtacccc caggttcttc atgcacacct gg                                    32
```